US007951958B2

(12) United States Patent
Brodney et al.

(10) Patent No.: US 7,951,958 B2
(45) Date of Patent: *May 31, 2011

(54) IMIDAZOLE COMPOUNDS FOR THE TREATMENT OF NEURODEGENERATIVE DISORDERS

(75) Inventors: Michael A. Brodney, East Lyme, CT (US); Karen J. Coffman, Pawcatuck, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/723,204

(22) Filed: Mar. 12, 2010

(65) Prior Publication Data

US 2010/0168107 A1 Jul. 1, 2010

Related U.S. Application Data

(63) Continuation of application No. 11/971,272, filed on Jan. 9, 2008, now Pat. No. 7,795,447, which is a continuation of application No. 11/078,898, filed on Mar. 11, 2005, now Pat. No. 7,342,118.

(60) Provisional application No. 60/555,623, filed on Mar. 23, 2004.

(51) Int. Cl.
*A61K 31/4164* (2006.01)
*A61K 31/4178* (2006.01)
*C07D 233/88* (2006.01)

(52) U.S. Cl. ............... 548/326.5; 514/397; 514/398

(58) Field of Classification Search ............... 548/326.5
See application file for complete search history.

(56) References Cited

U.S. PATENT DOCUMENTS

| 5,760,246 | A | 6/1998 | Biller et al. |
|---|---|---|---|
| 6,323,315 | B1 | 11/2001 | Pettit et al. |
| 6,329,342 | B1 | 12/2001 | Kauffman et al. |
| 6,639,076 | B1 | 10/2003 | Hauser et al. |
| 6,649,641 | B2 | 11/2003 | Behrens et al. |
| 6,828,331 | B1 | 12/2004 | Dodge et al. |
| 7,112,599 | B2 | 9/2006 | Chen |
| 7,163,942 | B2 | 1/2007 | Brodney et al. |
| 7,220,865 | B2 | 5/2007 | Chen et al. |
| 7,232,820 | B2 | 6/2007 | Chen |
| 7,238,721 | B2 | 7/2007 | Chen et al. |
| 7,241,786 | B2 | 7/2007 | Chen |
| 7,253,195 | B2 | 8/2007 | Chen |
| 7,309,709 | B2 | 12/2007 | Zhang |
| 7,342,118 | B2 | 3/2008 | Brodney et al. |
| 7,345,095 | B2 | 3/2008 | Brodney et al. |
| 7,384,968 | B2 | 6/2008 | Chen |
| 7,408,068 | B2 | 8/2008 | Chen |
| 7,521,464 | B2 | 4/2009 | Chen et al. |
| 7,781,435 | B2 * | 8/2010 | Brodney et al. ............ 514/235.5 |
| 7,795,447 | B2 * | 9/2010 | Brodney et al. ............ 548/326.5 |
| 2002/0004512 | A1 | 1/2002 | Bakshi et al. |
| 2003/0050314 | A1 | 3/2003 | Wehner et al. |
| 2003/0232868 | A1 | 12/2003 | Lehmann et al. |
| 2004/0122234 | A1 | 6/2004 | Hauser et al. |
| 2004/0152747 | A1 | 8/2004 | Chen et al. |
| 2005/0107381 | A1 | 5/2005 | Chen |
| 2005/0215610 | A1 | 9/2005 | Brodney et al. |
| 2005/0222227 | A1 | 10/2005 | Chen |
| 2007/0270426 | A1 | 11/2007 | Chen |
| 2008/0108675 | A1 | 5/2008 | Zhang |
| 2008/0227781 | A1 | 9/2008 | Brodney et al. |

FOREIGN PATENT DOCUMENTS

| EP | 0573271 | 12/1993 |
|---|---|---|
| EP | 0898963 | 3/1999 |
| JP | 07-101958 | 4/1995 |
| WO | WO99/08697 | 2/1999 |
| WO | WO99/08699 | 2/1999 |
| WO | WO00/49037 | 8/2000 |
| WO | WO01/81298 | 11/2001 |
| WO | WO02/10141 | 2/2002 |
| WO | WO03/055447 | 7/2003 |
| WO | WO03/055482 | 7/2003 |
| WO | WO03/104236 | 12/2003 |
| WO | WO2004/089937 | 10/2004 |
| WO | WO2005/058308 | 6/2005 |
| WO | WO2005/092864 | 10/2005 |

OTHER PUBLICATIONS

Brown, P., "Drug Therapy In Human and Experimental Transmissible Spongiform Encephalopathy," *Neurology*, 2002, 1720-1725, vol. 58.
Golub, T., et al., "Molecular Classification Of Cancer: Class Discovery And Class Prediction By Gene Expression Monitoring," *Science*, 1999, 531-537, vol. 286. Li, D., et al., "Synthesis of Ribavirin Analogues Containing Amino-Acid Residues," *Synthetic Communications*, 2005, 1017-1026, vol. 35.
Thompson, A., et al.,"Protein Conformational Misfolding And Amyloid Formation: Characteristics Of A New Class Of Disorders That Include Alzheimer's And Prion Diseases," *Current Medicinal Chemistry*, 2002, 1751-1762, vol. 9.

* cited by examiner

*Primary Examiner* — Laura L. Stockton
(74) *Attorney, Agent, or Firm* — Jeffrey H. Tidwell; Stephen D. Prodnuk; Leslie A. Robinson

(57) ABSTRACT

The present invention relates to compounds of the Formula I

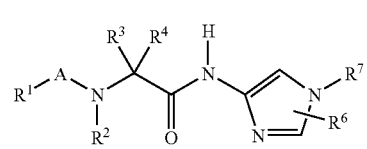

wherein $R^1$, $R^2$, $R^3$, $R^4$, $R^6$, $R^7$ and A are as defined. Compounds of the Formula I have activity inhibiting production of Aβ-peptide. The invention also relates to pharmaceutical compositions and methods for treating diseases and disorders, for example, neurodegenerative and/or neurological disorders, e.g., Alzheimer's disease, in a mammal comprising compounds of the Formula I.

22 Claims, No Drawings

IMIDAZOLE COMPOUNDS FOR THE TREATMENT OF NEURODEGENERATIVE DISORDERS

CROSS REFERENCE TO RELATED APPLICATION

The present application is a continuation of U.S. application Ser. No. 11/971,272 filed on Jan. 9, 2008, now U.S. Pat. No. 7,795,447, which is a continuation of U.S. application Ser. No. 11/078,898 filed on Mar. 11, 2005, now U.S. Pat. No. 7,342,118, which claim the benefit of U.S.S.N. 60/555,623 filed on Mar. 23, 2004, the contents of each of which are incorporated by reference herein in their entirety.

FIELD OF THE INVENTION

The present invention relates to the treatment of neurodegenerative and/or neurological disorders, such as Alzheimer's disease, in mammals, including humans. This invention also relates to inhibiting, in mammals, including humans, the production of Aβ-peptides that can contribute to the formation of neurological deposits of amyloid protein. More particularly, this invention relates to imidazole compounds, pharmaceutical compositions comprising such compounds and methods of using such compounds, i.e., for the treatment of neurodegenerative and/or neurological disorders, such as Alzheimer's disease, related to Aβ-peptide production.

BACKGROUND OF THE INVENTION

Dementia results from a wide variety of distinctive pathological processes. The most common pathological processes causing dementia are Alzheimer's disease (Aβ), cerebral amyloid angiopathy (CAA) and prion-mediated diseases. Aβ affects nearly half of all people past the age of 85, the most rapidly growing portion of the United States population. As such, the number of Aβ patients in the United States is expected to increase from about 4 million to about 14 million by the middle of the next century.

Treatment of Aβ typically is the support provided by a family member in attendance. Stimulated memory exercises on a regular basis have been shown to slow, but not stop, memory loss. A few drugs, for example Aricept™, provide treatment of Aβ.

A hallmark of Aβ is the accumulation in the brain of extracellular insoluble deposits called amyloid plaques and abnormal lesions within neuronal cells called neurofibrillary tangles. Increased plaque formation is associated with an increased risk of Aβ. Indeed, the presence of amyloid plaques, together with neurofibrillary tangles, is the basis for definitive pathological diagnosis of Aβ.

The major components of amyloid plaques are the amyloid Aβ-peptides, also called Aβ-peptides, that consist of several proteins including 38, 40, 42 or 43 amino acids, designated as the $A\beta_{1-38}$, $A\beta_{1-40}$, $A\beta_{1-42}$ and $A\beta_{1-43}$ peptides, respectively. The Aβ-peptides are thought to cause nerve cell destruction, in part, because they are toxic to neurons in vitro and in vivo.

The Aβ peptides are derived from larger amyloid precursor proteins (APP proteins), that consist of four proteins containing 695, 714, 751 or 771 amino acids, designated as the $APP_{695}$, $APP_{714}$, $APP_{751}$ and $APP_{771}$, respectively. Proteases are believed to produce the Aβ peptides by cleaving specific amino acid sequences within the various APP proteins. The proteases are named "secretases" because the Aβ-peptides they produce are secreted by cells into the extracellular environment. These secretases are each named according to the cleavage(s) they make to produce the Aβ-peptides. The secretase that forms the amino terminal end of the Aβ-peptides is called the beta-secretase. The secretase that forms the carboxyl terminal end of the Aβ-peptides is called the gamma-secretase.

This invention relates to novel compounds that inhibit Aβ-peptide production, to pharmaceutical compositions comprising such compounds, and to methods of using such compounds to treat neurodegenerative and/or neurological disorders.

SUMMARY OF THE INVENTION

The present invention relates to compounds of the Formula I

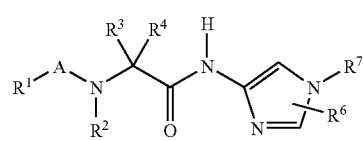

wherein A is absent or is selected from

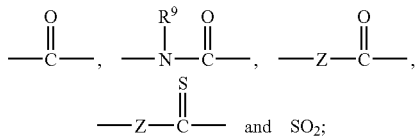

Z is selected from —$CH_2$—, —CH(OH)—, —CH($C_1$-$C_6$ alkyl)—, —CH($C_1$-$C_6$ alkoxy)—, —CH($NR^9R^{10}$)—, —CH($CH_2$(OH))—, —CH(CH($C_1$-$C_4$ alkyl)(OH))— and —CH(C($C_1$-$C_4$ alkyl)($C_1$-$C_4$alkyl)(OH))—, for example —CH(C($CH_3$)($CH_3$)(OH))— or —CH(C($CH_3$)($CH_2CH_3$)(OH))—;

$R^1$ is selected from $C_1$-$C_{20}$ alkyl, $C_2$-$C_{20}$ alkenyl, $C_2$-$C_{20}$ alkynyl, $C_1$-$C_{20}$ alkoxy, $C_2$-$C_{20}$ alkenoxy, $C_1$-$C_{20}$ hydroxyalkyl, $C_3$-$C_8$ cycloalkyl, benzo($C_3$-$C_8$ cycloalkyl), benzo($C_3$-$C_8$ heterocycloalkyl), $C_4$-$C_8$ cycloalkenyl, ($C_5$-$C_{11}$)bi- or tricycloalkyl, benzo($C_5$-$C_{11}$)bi- or tricycloalkyl, ($C_7$-$C_{11}$)bi- or tricycloalkenyl, (3-8 membered) heterocycloalkyl, $C_6$-$C_{14}$ aryl and (5-14 membered) heteroaryl, wherein each hydrogen atom of said alkyl, alkenyl, alkynyl, alkoxy and alkenoxy is optionally independently replaced with halo, and wherein said cycloalkyl, benzo($C_3$-$C_8$ cycloalkyl), cycloalkenyl, (3-8 membered) heterocycloalkyl, $C_6$-$C_{14}$ aryl and (5-14 membered) heteroaryl is optionally independently substituted with from one to four substituents independently selected from $C_1$-$C_{10}$ alkyl optionally substituted with from one to three halo atoms, $C_1$-$C_{10}$ alkoxy optionally substituted with from one to three halo atoms, $C_1$-$C_{10}$ hydroxyalkyl, halo, preferably fluorine, —OH, —CN, —$NR^9R^{10}$, —C(=O)$NR^9R^{10}$, —C(=O)$R^{11}$, $C_3$-$C_8$ cycloalkyl and (3-8 membered) heterocycloalkyl;

$R^2$ is selected from H, $C_1$-$C_6$ alkyl, $C_2$-$C_6$ alkenyl, $C_3$-$C_8$ cycloalkyl and $C_5$-$C_8$ cycloalkenyl, wherein $R^2$ is optionally independently substituted with from one to three substituents independently selected from $C_1$-$C_4$ alkyl optionally substituted with from one to three halo atoms, $C_1$-$C_4$ alkoxy optionally substituted with from one to three halo atoms, halo and —OH;

or $R^1$ and $R^2$ together with the A group when present and the nitrogen atom to which $R^2$ is attached, or $R^1$ and $R^2$ together with the nitrogen atom to which $R^1$ and $R^2$ are attached when A is absent, may optionally form a four to eight membered ring;

$R^3$ is selected from H, $C_1$-$C_6$ alkyl, $C_2$-$C_6$ alkenyl, $C_2$-$C_6$ alkynyl, $C_3$-$C_6$ cycloalkyl, $C_5$-$C_6$ cycloalkenyl and (3-8 membered) heterocycloalkyl, wherein said alkyl, alkenyl, alkynyl, cycloalkyl, cycloalkenyl and heterocycloalkyl are each optionally independently substituted with from one to three substituents independently selected from $C_1$-$C_4$ alkoxy, halo, —OH—S($C_1$-$C_4$)alkyl and (3-8 membered) heterocycloalkyl;

$R^4$ is H, $C_1$-$C_6$ alkyl or halo;

or $R^3$ and $R^4$ may together with the carbon atom to which they are attached optionally form a moiety selected from cyclopropyl, cyclobutyl, cyclopentyl, cyclohexyl, morpholino, piperidino, pyrrolidino, tetrahydrofuranyl and perhydro-2H-pyran, wherein said moiety formed by $R^3$ and $R^4$ is optionally substituted with from one to three substituents independently selected from $C_1$-$C_6$ alkyl optionally substituted with from one to three halo atoms, $C_1$-$C_6$ alkoxy optionally substituted with from one to three halo atoms, halo, —OH, —CN and allyl;

$R^6$ is selected from H, $C_1$-$C_6$ alkyl, $C_2$-$C_6$ alkylene, $C_1$-$C_6$ alkoxy, halo, —CN, $C_3$-$C_{12}$ cycloalkyl, $C_4$-$C_{12}$ cycloalkenyl and $C_6$-$C_{10}$ aryl, (5-10 membered) heteroaryl, wherein said alkyl, alkylene and alkoxy of $R^6$ are each optionally independently substituted with from one to three substituents independently selected from halo and —CN, and wherein said cycloalkyl, cycloalkenyl and aryl and heteroaryl of $R^6$ are each optionally independently substituted with from one to three substituents independently selected from $C_1$-$C_4$ alkyl optionally substituted with from one to three halo atoms, $C_1$-$C_4$ alkoxy optionally substituted with from one to three halo atoms, halo and —CN;

$R^7$ is selected from H, $C_1$-$C_{20}$ alkyl, $C_1$-$C_{20}$ alkoxy, $C_1$-$C_{20}$ hydroxyalkyl, $C_3$-$C_{12}$ cycloalkyl, $C_4$-$C_{12}$ cycloalkenyl, ($C_5$-$C_{20}$) bi- or tricycloalkyl, ($C_7$-$C_{20}$)bi- or tricycloalkenyl, (3-12 membered) heterocycloalkyl, (7-20 membered) heterobi- or heterotricycloalkyl, $C_6$-$C_{14}$ aryl and (5-15 membered) heteroaryl, wherein $R^7$ is optionally independently substituted with from one to four substituents independently selected from $C_1$-$C_{20}$ alkyl optionally substituted with from one to three halo atoms, $C_1$-$C_{20}$ alkoxy, —OH, —CN, —NO$_2$, —NR$^9$R$^{10}$, —C(=O)NR$^9$R$^{10}$, —C(=O)R$^{11}$, —C(=O)OR$^{11}$, —S(O)$_n$NR$^9$R$^{10}$, —S(O)$_n$R$^{11}$, $C_3$-$C_{12}$ cycloalkyl, (4-12 membered) heterocycloalkyl optionally substituted with from one to three OH or halo groups, (4-12 membered) heterocycloalkoxy, $C_6$-$C_{14}$ aryl, (5-15 membered) heteroaryl, $C_6$-$C_{12}$ aryloxy and (5-12 membered) heteroaryloxy;

or $R^6$ and $R^7$ may together with the carbon and nitrogen atoms to which they are respectively attached optionally form a (5-8 membered) heterocycloalkyl ring, a (5-8 membered) heterocycloalkenyl ring or a (6-10 membered) heteroaryl ring, wherein said heterocycloalkyl, heterocycloalkenyl and heteroaryl rings are each optionally independently substituted with from one to three substituents independently selected from halo, $C_1$-$C_6$ alkyl, optionally substituted with from one to three halo atoms, $C_1$-$C_6$ alkoxy optionally substituted with from one to three halo atoms, $C_1$-$C_6$ hydroxyalkyl, —OH, —(CH$_2$)$_{zero-10}$NR$^9$R$^{10}$, —(CH$_2$)$_{zero-10}$C(=O)NR$^9$R$^{10}$, —SO$_2$NR$^9$R$^{10}$ and $C_3$-$C_{12}$ cycloalkyl;

$R^9$ and $R^{10}$ are each independently selected from H, $C_1$-$C_{10}$ alkyl wherein each hydrogen atom of said $C_1$-$C_{10}$ alkyl is optionally independently replaced with a halo atom, preferably a fluorine atom, $C_2$-$C_{10}$ alkenyl, $C_2$-$C_{10}$ alkynyl, $C_1$-$C_6$ alkoxy wherein each hydrogen atom of said $C_1$-$C_6$ alkoxy is optionally independently replaced with a halo atom, $C_2$-$C_6$ alkenoxy, $C_2$-$C_6$ alkynoxy, —C(=O)R$^{11}$, —S(O)$_n$R$^{11}$, $C_3$-$C_8$ cycloalkyl, $C_4$-$C_8$ cycloalkenyl, ($C_5$-$C_{11}$)bi- or tricycloalkyl, ($C_7$-$C_{11}$)bi- or tricycloalkenyl, (3-8 membered) heterocycloalkyl, $C_6$-$C_{14}$ aryl and (5-14 membered) heteroaryl, wherein said alkyl and alkoxy are each optionally independently substituted with from one to three substituents independently selected from halo and —OH, and wherein said cycloalkyl, cycloalkenyl, bi- or tricycloalkyl, bi- or tricycloalkenyl, heterocycloalkyl, aryl and heteroaryl are each optionally independently substituted with from one to three substituents independently selected from halo, —OH, $C_1$-$C_6$ alkyl optionally independently substituted with from one to six halo atoms, $C_2$-$C_6$ alkenyl, $C_2$-$C_6$ alkynyl, $C_1$-$C_6$ alkoxy, $C_2$-$C_6$ alkenoxy, $C_2$-$C_6$ alkynoxy and $C_1$-$C_6$ hydroxyalkyl;

or NR$^9$R$^{10}$ may form a (4-7 membered) heterocycloalkyl, wherein said heterocycloalkyl optionally comprises from one to two further heteroatoms independently selected from N, O and S, and wherein said heterocycloalkyl optionally contains from one to three double bonds, and wherein said heterocycloalkyl is optionally independently substituted with from one to three substituents independently selected from $C_1$-$C_6$ alkyl optionally substituted with from one to six halo atoms, $C_2$-$C_6$ alkenyl, $C_2$-$C_6$ alkynyl, $C_1$-$C_6$ alkoxy, $C_2$-$C_6$ alkenoxy, $C_2$-$C_6$ alkynoxy, $C_1$-$C_6$ hydroxyalkyl, $C_2$-$C_6$ hydroxyalkenyl, $C_2$-$C_6$ hydroxyalkynyl, halo, —OH, —CN, —NO$_2$, —C(=O)R$^{11}$—C(=O)OR$^{11}$, —S(O)$_n$R$^{11}$ and —S(O)$_n$NR$^9$R$^{10}$;

$R^{11}$ is selected from H, $C_1$-$C_8$ alkyl, $C_3$-$C_8$ cycloalkyl, $C_4$-$C_8$ cycloalkenyl, ($C_5$-$C_{11}$)bi- or tricycloalkyl, —($C_7$-$C_{11}$) bi- or tricycloalkenyl, (3-8 membered) heterocycloalkyl, $C_6$-$C_{10}$ aryl and (5-14 membered) heteroaryl, wherein said alkyl of R$^{11}$ is optionally independently substituted with from one to three substituents independently selected from —OH, —CN and $C_3$-$C_8$ cycloalkyl, and wherein each hydrogen atom of said alkyl is optionally independently replaced with a halo atom, preferably a fluorine atom, and wherein said cylcoalkyl, cycloalkenyl, heterocycloalkyl, aryl and hetereoaryl of R$^{11}$ are each optionally independently substituted with from one to three substituents independently selected from halo, $C_1$-$C_8$ alkyl optionally substituted with from one to three halo atoms, —OH, —CN and $C_3$-$C_8$ cycloalkyl;

n is in each instance an integer independently selected from zero, 1, 2 and 3;

and the pharmaceutically acceptable salts of such compounds.

Compounds of the Formula I may have optical centers and therefore may occur in different enantiomeric and diastereomeric configurations. The present invention includes all enantiomers, diastereomers, and other stereoisomers of such compounds of the Formula I, as well as racemic compounds and racemic mixtures and other mixtures of stereoisomers thereof.

Pharmaceutically acceptable salts of the compounds of Formula I include the acid addition and base salts thereof.

Suitable acid addition salts are formed from acids which form non-toxic salts. Examples include, but are not limited to, the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mandelates mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, salicylate, saccharate, stearate, succinate, sulfonate, stannate, tartrate, tosylate, trifluoroacetate and xinofoate salts.

Suitable base salts are formed from bases which form non-toxic salts. Examples include, but are not limited to, the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002). Pharmaceutically acceptable salts of compounds of Formula I may be prepared by one or more of three methods:

(i) by reacting the compound of Formula I with the desired acid or base;

(ii) by removing an acid- or base-labile protecting group from a suitable precursor of the compound of Formula I or by ring-opening a suitable cyclic precursor, for example, a lactone or lactam, using the desired acid or base; or (iii) by converting one salt of the compound of Formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionised to almost non-ionised.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see Polymorphism in Pharmaceutical Solids by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as $-COO^-Na^+$, $-COO^-K^+$, or $-SO_3^-Na^+$) or non-ionic (such as $-N^-N^+(CH_3)_3$) polar head group. For more information, see Crystals and the Polarizing Microscope by N. H. Hartshorne and A. Stuart, $4^{th}$ Edition (Edward Arnold, 1970).

Hereinafter all references to compounds of Formula I include references to salts, solvates, multi-component complexes and liquid crystals thereof and to solvates, multi-component complexes and liquid crystals of salts thereof.

The compounds of the invention include compounds of Formula I as hereinbefore defined, including all polymorphs and crystal habits thereof, prodrugs and isomers thereof (including optical, geometric and tautomeric isomers) as hereinafter defined and isotopically-labeled compounds of Formula I.

Unless otherwise indicated, as used herein, the term "A is absent" means a direct bond between the nitrogen and $R^1$ (i.e., $-N-R^1$).

Unless otherwise indicated, as used herein, the term "alkyl" includes saturated monovalent hydrocarbon radicals having straight or branched moieties. Examples of alkyl groups include, but are not limited to, methyl, ethyl, n-propyl, isopropyl, and t-butyl.

Unless otherwise indicated, as used herein, the term "alkenyl" includes alkyl moieties having at least one carbon-carbon double bond wherein alkyl is as defined above. Examples of alkenyl include, but are not limited to, ethenyl and propenyl.

Unless otherwise indicated, as used herein, the term "alkynyl" includes alkyl moieties having at least one carbon-carbon triple bond wherein alkyl is as defined above. Examples of alkynyl groups include, but are not limited to, ethynyl and 2-propynyl.

Unless otherwise indicated, as used herein, the term "alkoxy", means "alkyl-O—", wherein "alkyl" is as defined above. Examples of "alkoxy" groups include, but are not limited to, methoxy, ethoxy, propoxy, butoxy, pentoxy and allyloxy.

Unless otherwise indicated, as used herein, the term "alkenoxy", means "alkenyl-O—", wherein "alkenyl" is as defined above.

Unless otherwise indicated, as used herein, the term "cycloalkyl" includes non-aromatic saturated cyclic alkyl moieties wherein alkyl is as defined above. Examples of cycloalkyl include, but are not limited to, cyclopropyl, cyclobutyl, cyclopentyl, cyclohexyl and cycloheptyl. "Bicycloalkyl" and "tricycloalkyl" groups are non-aromatic saturated carbocyclic groups consisting of two or three rings respectively, wherein said rings share at least one carbon atom. Unless otherwise indicated, for purposes of the present invention, bicycloalkyl groups include spiro groups and fused ring groups. Examples of bicycloalkyl groups include, but are not limited to, bicyclo-[3.1.0]-hexyl, bicyclo-2.2.1]-hept-1-yl, norbornyl, spiro[4.5]decyl, spiro[4.4]nonyl, spiro[4.3]octyl, and spiro[4.2]heptyl. An example of a tricycloalkyl group is adamantanyl. Other cycloalkyl, bicycloalkyl, and tricycloalkyl groups are known in the art, and such groups are encompassed by the definitions "cycloalkyl", "bicycloalkyl" and "tricycloalkyl" herein.

"Cycloalkenyl", "bicycloalkenyl", and "tricycloalkenyl" refer to non-aromatic carbocyclic cycloalkyl, bicycloalkyl, and tricycloalkyl moieties as defined above, except comprising one or more carbon-carbon double bonds connecting carbon ring members (an "endocyclic" double bond) and/or one or more carbon-carbon double bonds connecting a carbon ring member and an adjacent non-ring carbon (an "exocyclic" double bond). Examples of cycloalkenyl groups include, but are not limited to, cyclopentenyl, cyclobutenyl, and cyclohexenyl, and a non-limiting example of a bicycloalkenyl group is norbornenyl. Other cycloalkenyl, bicycloalkenyl, and tricycloalkenyl groups are known in the art, and such groups are included within the definitions "cycloalkenyl", "bicycloalkenyl" and "tricycloalkenyl" herein.

Cycloalkyl, cycloalkenyl, bicycloalkyl, and bicycloalkenyl groups also include groups that are substituted with one or more oxo moieties. Examples of such groups with oxo moieties are oxocyclopentyl, oxocyclobutyl, oxocyclopentenyl, and norcamphoryl.

As used herein, the term "benzocycloalkyl" includes, without limitation, moieties such as tetrahydronaphthyl, indanyl, 1,2-benzocylcoheptanyl and the like.

Unless otherwise indicated, as used herein, the term "aryl" includes an organic radical derived from an aromatic hydrocarbon by removal of one hydrogen, such as phenyl, naphthyl, indenyl, indanyl, and fluorenyl. "Aryl" encompasses fused ring groups wherein at least one ring is aromatic.

Unless otherwise indicated, as used herein, the terms "heterocyclic" and "heterocycloalkyl" refer to non-aromatic cyclic groups containing one or more heteroatoms, preferably from one to four heteroatoms, each selected from O, S and N. "Heterobicycloalkyl" groups are non-aromatic two-ringed cyclic groups, wherein said rings share one or two atoms, and wherein at least one of the rings contains a heteroatom (O, S, or N). Heterobicycloalkyl groups for purposes of the present invention, and unless otherwise indicated, include spiro groups and fused ring groups. "Heterotricycloalkyl" groups are non-aromatic three-ringed cyclic groups, wherein said rings are fused to one another or form a spiro group (in other words, at least two of said rings share one or two atoms and the third ring shares one or two atoms with at least one of said two rings). The heterotricycloalkyl groups of the compounds of the present invention can include one or more O, S and/or N heteroatoms. In one embodiment, each ring in the heterobicycloalkyl or heterotricycloalkyl contains up to four heteroatoms (i.e. from zero to four heteroatoms, provided that at least one ring contains at least one heteroatom). The heterocycloalkyl, heterobicycloalkyl and heterotricycloalkyl groups of the present invention can also include ring systems substituted with one or more oxo moieties. The heterocyclic groups, including the heterobicyclic and heterotricyclic groups, may comprise double or triple bonds, e.g. heterocycloalkenyl, heterobicycloalkenyl, and heterotricycloalkenyl. Examples of non-aromatic heterocyclic groups are aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, quinolizinyl, quinuclidinyl, 1,4-dioxaspiro[4.5]decyl, 1,4-dioxaspiro[4.4]nonyl, 1,4-dioxaspiro[4.3]octyl, and 1,4-dioxaspiro[4.2]heptyl.

Unless otherwise indicated, as used herein, "heteroaryl" refers to aromatic groups containing one or more heteroatoms (O, S, or N), preferably from one to four heteroatoms. A multicyclic group containing one or more heteroatoms wherein at least one ring of the group is aromatic is a "heteroaryl" group. The heteroaryl groups of this invention can also include ring systems substituted with one or more oxo moieties. Examples of heteroaryl groups are pyridinyl, pyridazinyl, imidazolyl, pyrimidinyl, pyrazolyl, triazolyl, pyrazinyl, quinolyl, isoquinolyl, 1,2,3,4-tetrahydroquinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, 1,2,4-trizainyl, 1,3,5-triazinyl, isoindolyl, 1-oxoisoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

As appreciated by the artisan, the use of Formula I is a convenience, and the invention is understood to envision and embrace each and every species thereunder as though individually identified and set forth herein. Thus, the present invention contemplates each species separately and any and all combinations and permutations of species falling within Formula I.

The foregoing groups, as derived from the compounds listed above, may be C-attached or N-attached where such is possible. For instance, a group derived from pyrrole may be pyrrol-1-yl (N-attached) or pyrrol-3-yl (C-attached). The terms referring to the groups also encompass all possible tautomers.

As indicated, so-called 'prodrugs' of the compounds of Formula I are also within the scope of the invention. Thus certain derivatives of compounds of Formula I which may have little or no pharmacological activity themselves can, when administered into or onto the body, be converted into compounds of Formula I having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of Formula I with certain moieties known to those skilled in the art as 'pro-moieties' as described, for example, in Design of Prodrugs by H. Bundgaard (Elsevier, 1985).

Some examples of prodrugs in accordance with the invention include, but are not limited to, (i) where the compound of Formula I contains a carboxylic acid functionality (—COOH), an ester thereof, for example, a compound wherein the hydrogen of the carboxylic acid functionality of the compound of Formula (I) is replaced by ($C_1$-$C_8$)alkyl;

(ii) where the compound of Formula I contains an alcohol functionality (—OH), an ether thereof, for example, a compound wherein the hydrogen of the alcohol functionality of the compound of Formula I is replaced by ($C_1$-$C_6$)alkanoyloxymethyl; and (iii) where the compound of Formula I contains a primary or secondary amino functionality (—NH$_2$ or —NHR where R≠H), an amide thereof, for example, a compound wherein, as the case may be, one or both hydrogens of the amino functionality of the compound of Formula I is/are replaced by (C$_1$-C$_{10}$)alkanoyl.

Further examples of replacement groups in accordance with the foregoing examples and examples of other prodrug types may be found in the aforementioned references.

Moreover, certain compounds of Formula I may themselves act as prodrugs of other compounds of Formula I.

Also included within the scope of the invention are metabolites of compounds of Formula I, that is, compounds formed in vivo upon administration of the drug. Some examples of metabolites in accordance with the invention include, but are not limited to, (i) where the compound of Formula I contains a methyl group, an hydroxymethyl derivative thereof (—CH$_3$->—CH$_2$OH):

(ii) where the compound of Formula I contains an alkoxy group, an hydroxy derivative thereof (—OR->—OH);

(iii) where the compound of Formula I contains a tertiary amino group, a secondary amino derivative thereof (—NR$^1$R$^2$->—NHR$^1$ or —NHR$^2$);

(iv) where the compound of Formula I contains a secondary amino group, a primary derivative thereof (—NHR$^1$->—NH$_2$);

(v) where the compound of Formula I contains a phenyl moiety, a phenol derivative thereof (-Ph->-PhOH); and (vi) where the compound of Formula I contains an amide group, a carboxylic acid derivative thereof (—CONH$_2$->COOH).

Compounds of Formula I containing one or more asymmetric carbon atoms can exist as two or more stereoisomers. Where a compound of Formula I contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of Formula I containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of Formula I, including compounds exhibiting more than one type of isomerism, and mixtures of one or more thereof. Also included are acid addition or base salts wherein the counterion is optically active, for example, d-lactate or l-lysine, or racemic, for example, dl-tartrate or di-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of Formula I contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, Stereochemistry of Organic Compounds by E. L. Eliel and S. H. Wilen (Wiley, 1994).

The present invention includes all pharmaceutically acceptable isotopically-labelled compounds of Formula I wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^2$H and $^3$H, carbon, such as $^{11}$C, $^{13}$C and $^{14}$C, chlorine, such as $^{36}$C, fluorine, such as $^{13}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of Formula I, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of Formula I can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. D$_2$O, d$_6$-acetone, d$_6$-DMSO.

Also within the scope of the invention are intermediate compounds of Formula II as hereinbefore defined, all salts, solvates and complexes thereof and all solvates and complexes of salts thereof as defined hereinbefore for compounds of Formula I. The invention includes all polymorphs of the aforementioned species and crystal habits thereof.

When preparing compounds of Formula I in accordance with the invention, it is open to a person skilled in the art to routinely select the form of compound of Formula II which provides the best combination of features for this purpose. Such features include, but are not limited to, the melting point, solubility, processability and yield of the intermediate form and the resulting ease with which the product may be purified on isolation.

In one aspect, the present invention relates to compounds of the Formula I wherein A is absent or is

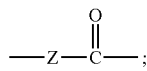

Z is —$CH_2$, —CH(OH) or —CH($C_1$-$C_6$ alkyl); $R^1$ is $C_1$-$C_{10}$ alkyl, $C_6$-$C_{10}$ aryl, (6-10 membered) heteroaryl or benzo($C_5$-$C_6$ cycloalkyl), wherein when $R^1$ is $C_6$-$C_{10}$ aryl, $C_6$-$C_{10}$ heteroaryl or benzo($C_5$-$C_6$ cycloalkyl), $R^1$ is optionally independently substituted with from one to three substituents independently selected from $C_1$-$C_6$ alkyl, halo, preferably fluorine, and OH; $R^2$ is H or $C_1$-$C_6$ alkyl; $R^3$ is H, —$CH_2CH_2SCH_3$, —O($C_1$-$C_4$)alkyl or $C_1$-$C_6$ alkyl; $R^4$ is H or $C_1$-$C_6$ alkyl; $R^6$ is H or $C_1$-$C_6$ alkyl; $R^7$ is $C_1$-$C_{10}$ alkyl, $C_3$-$C_8$ cycloalkyl or (4-10 membered) heterocycloalkyl, wherein $R^7$ is optionally independently substituted with from one to three substituents independently selected from $C_1$-$C_8$ alkyl, $C_1$-$C_8$ alkoxy, OH, —$NR^9R^{10}$, —C(=O)$NR^9R^{10}$, —C(=O)$R^{11}$, —C(=O)$OR^{11}$ and (4-6 membered) heterocycloalkyl optionally substituted with from one to three OH or halo groups; and $R^9$, $R^{10}$ and $R^{11}$ are each independently selected from H and $C_1$-$C_6$ alkyl, wherein each hydrogen atom of said $C_1$-$C_6$ alkyl is optionally independently replaced with a halo atom, preferably a fluorine atom.

In another aspect, A is absent or is

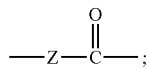

Z is —$CH_2$ or —CH(OH); $R^1$ is $C_1$-$C_{10}$ alkyl, $C_6$-$C_{10}$ aryl or benzo($C_5$-$C_6$ cycloalkyl), wherein when $R^1$ is $C_6$-$C_{10}$ aryl or benzo($C_5$-$C_6$ cycloalkyl), $R^1$ is optionally independently substituted with from one to three independently selected halo substituents, preferably fluorine; $R^2$ is H or $C_1$-$C_6$ alkyl; $R^3$ is H or $C_1$-$C_6$ alkyl; $R^4$ is H or $C_1$-$C_6$ alkyl; $R^6$ is H or $C_1$-$C_6$ alkyl; $R^7$ is $C_1$-$C_{10}$ alkyl or (4-10 membered) heterocycloalkyl, wherein $R^7$ is optionally independently substituted with from one to three substituents independently selected from $C_1$-$C_8$ alkyl, $C_1$-$C_8$ alkoxy, OH, —$NR^9R^{10}$, —C(=O)$R^{11}$, —C(=O)$OR^{11}$ and (4-6 membered) heterocycloalkyl optionally substituted with from one to three OH groups; and $R^9$, $R^{10}$ and $R^{11}$ are each independently selected from H and $C_1$-$C_6$ alkyl, wherein each hydrogen atom of said $C_1$-$C_6$ alkyl is optionally independently replaced with a halo atom, preferably a fluorine atom.

In another aspect, the present invention relates to compounds of the Formula I wherein A is absent; $R^1$ is benzo($C_5$-$C_6$ alkyl) optionally substituted with from one to three substituents independently selected from $C_1$-$C_6$ alkyl, halo, preferably fluorine and OH; $R^2$ is H or $C_1$-$C_6$ alkyl; $R^3$ is H or $C_1$-$C_6$ alkyl; $R^4$ is H or $C_1$-$C_6$ alkyl; $R^6$ is H or $C_1$-$C_6$ alkyl; $R^7$ is $C_1$-$C_{10}$ alkyl, wherein $R^7$ is optionally independently substituted with from one to three substituents independently selected from $C_1$-$C_8$ alkoxy, OH, —$NR^9R^{10}$, —C(=O)$NR^9R^{10}$, —C(=O)$R^{11}$ and —C(=O)$OR^{11}$.

In another aspect, A is absent; $R^1$ is benzo($C_5$-$C_6$ alkyl) optionally substituted with from one to three independently selected halo substituents, preferably fluorine; $R^2$ is H or $C_1$-$C_6$ alkyl; $R^3$ is H, —$CH_2CH_2SCH_3$—O($C_1$-$C_4$)alkyl or $C_1$-$C_6$ alkyl; $R^4$ is H or $C_1$-$C_6$ alkyl; $R^6$ is H or $C_1$-$C_6$ alkyl; $R^7$ is $C_1$-$C_{10}$ alkyl, wherein $R^7$ is optionally independently substituted with from one to three substituents independently selected from $C_1$-$C_8$ alkoxy, OH, —$NR^9R^{10}$, —C(=O)$NR^9R^{10}$, —C(=O)$R^{11}$, —C(=O)$OR^{11}$ and (4-6 membered) heterocycloalkyl.

In another aspect, $R^1$ is 1,2,3,4-tetrahydronaphthalene or indanyl optionally substituted with 1 to 3 fluorine or chlorine atoms.

In another aspect, the present invention relates to compounds of the Formula I wherein A is

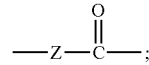

Z is —$CH_2$, —CH(OH) or —CH($C_1$-$C_6$ alkyl); $R^1$ is $C_1$-$C_{10}$ alkyl, $C_6$-$C_{10}$ aryl or (6-10 membered) heteroaryl, wherein said alkyl, aryl and heteroaryl are optionally independently substituted with from one to three substituents independently selected from $C_1$-$C_6$ alkyl, halo, preferably fluorine and OH; $R^2$ is H or $C_1$-$C_6$ alkyl; $R^3$ is H or $C_1$-$C_6$ alkyl; $R^4$ is H or $C_1$-$C_6$ alkyl; $R^6$ is H or $C_1$-$C_6$ alkyl; $R^7$ is $C_1$-$C_{10}$ alkyl, $C_3$-$C_8$ cycloalkyl or (4-10 membered) heterocycloalkyl, wherein $R^7$ is optionally independently substituted with from one to three substituents independently selected from $C_1$-$C_8$ alkyl, $C_1$-$C_8$ alkoxy, OH, —$NR^9R^{10}$, —C(=O)$NR^9R^{10}$, —C(=O)$R^{11}$, —C(=O)$OR^{11}$ and (4-6 membered) heterocycloalkyl optionally substituted with from one to three OH or halo groups.

In another aspect, A is

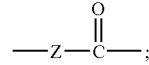

Z is —$CH_2$ or —CH(OH); $R^1$ is $C_1$-$C_{10}$ alkyl or $C_6$-$C_{10}$ aryl, wherein said alkyl and aryl are optionally independently substituted with from one to three independently selected halo substituents, preferably fluorine; $R^2$ is H or $C_1$-$C_6$ alkyl; $R^3$ is H or $C_1$-$C_6$ alkyl; $R^4$ is H or $C_1$-$C_6$ alkyl; $R^6$ is H or $C_1$-$C_6$ alkyl; $R^7$ is $C_1$-$C_{10}$ alkyl or (4-10 membered) heterocycloalkyl, wherein $R^7$ is optionally independently substituted with from one to three substituents independently selected from $C_1$-$C_8$ alkyl, $C_1$-$C_8$ alkoxy, OH, —$NR^9R^{10}$, —C(=O)$R^{11}$, —C(=O)$OR^{11}$ and (4-6 membered) heterocycloalkyl optionally substituted with from one to three OH groups.

In another aspect, the (4-10 membered) heterocycloalkyl group of $R^7$ is azetidinyl, pyrrolidinyl or piperidinyl; and the (4-6 membered) heterocycloalkyl substituent of $R^7$ is morpholino pyrrolidinyl or piperidinyl.

In another aspect, —$R^7$ is a $C_1$-$C_6$ alkyl optionally substituted with —$NR^9R^{10}$, morpholino, pyrrolidinyl or piperidinyl.

In another aspect, R⁴ is H and R³ is methyl, ethyl butyl, isobutyl, propyl, isopropyl, —CH₂CH₂SCH₃, or —CH₂CH₂OCH₃.

In another aspect, wherein R1 is aryl, A is

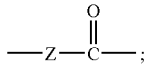

Z is —CH₂, and R⁷ is a C₁-C₆ alkyl optionally substituted with —NR⁹R¹⁰, morpholino, pyrrolidinyl or piperidinyl.

In another aspect, the compound of Formula I has the following structure, where the stereochemistry of the R³ and R⁴ substituents are shown below:

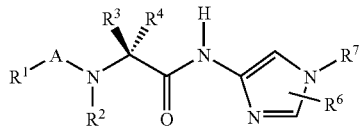

In another aspect, in the stereochemistry structure above, R⁴ and R² are hydrogen.

Specific embodiments of the present invention include the following compounds of Formula I, all pharmaceutically acceptable salts thereof, complexes thereof, and derivatives thereof that convert into a pharmaceutically active compound upon administration:

3-(4-{2-[2-(3,5-Difluoro-phenyl)-acetylamino]-pentanoylamino}-imidazol-1-yl)-butyric acid methyl ester;

3-{4-[2-(2-Hydroxy-3-methyl-butyrylamino)-pentanoylamino]-imidazol-1-yl}-3-methyl-butyric acid methyl ester;

3-(4-{2-[2-(3,5-Difluoro-phenyl)-acetylamino]-pentanoylamino}-imidazol-1-yl)-3-methyl-butyric acid methyl ester;

3-{4-[2-(2-Hydroxy-3,3-dimethyl-butyrylamino)-pentanoylamino]-imidazol-1-yl}-3-methyl-butyric acid methyl ester;

2-(2-Hydroxy-3,3-dimethyl-butyrylamino)-pentanoic acid [1-(1-ethyl-propyl)-1H-imidazol-4-yl]-amide;

2-[2-(3,5-Difluoro-phenyl)-acetylamino]-pentanoic acid [1-(1-ethyl-propyl)-1H-imidazol-4-yl]-amide;

2-[2-(3,5-Difluoro-phenyl)-2-hydroxy-acetylamino]-pentanoic acid [1-(1-ethyl-propyl)-1H-imidazol-amide;

2-(4-{2-[2-(3,5-Difluoro-phenyl)-acetylamino]-pentanoylamino}-imidazol-1-yl)-2-methyl-propionic acid methyl ester;

2-(4-{2-[2-(3,5-Difluoro-phenyl)-2-hydroxy-acetylamino]-pentanoylamino}-imidazol-1-yl)-2-methyl-propionic acid methyl ester;

2-{4-[2-(2-Hydroxy-3,3-dimethyl-butyrylamino)-pentanoylamino]-imidazol-1-yl}-2-methyl-propionic acid methyl ester;

2-{4-[2-(2-Hydroxy-3-methyl-butyrylamino)-pentanoylamino]-imidazol-1-yl}-2-methyl-propionic acid methyl ester;

3-(4-{2-[2-(3,5-Difluoro-phenyl)-acetylamino]-propionylamino}-imidazol-1-yl)-3-methyl-butyric acid methyl ester;

3-{4-[2-(2-Hydroxy-3,3-dimethyl-butyrylamino)-propionylamino]-imidazol-1-yl}-3-methyl-butyric acid methyl ester;

4-(4-{2-[2-(3,5-Difluoro-phenyl)-acetylamino]-pentanoylamino}-imidazo-1-yl)-piperidine-1-carboxylic acid tert-butyl ester;

2-[2-(3,5-Difluoro-phenyl)-acetylamino]-pentanoic acid [1-(1,1-dimethyl-2-pyrrolidin-1-yl-ethyl)-1H-imidazol-4-yl]-amide;

2-[2-(3-Trifluoromethyl-phenyl)-acetylamino]-pentanoic acid [1-(1,1-dimethyl-2-pyrrolidin-1-yl-ethyl)-1H-imidazol-4-yl]-amide;

2-[2-(3-Trifluoromethoxy-phenyl)-acetylamino]-pentanoic acid [1-(1,1-dimethyl-2-pyrrolidin-1-yl-ethyl)-1H-imidazol-4-yl]-amide;

2-[2-(3,5-Difluoro-phenyl)-acetylamino]-pentanoic acid [1-(1,1-dimethyl-2-morpholin-4-yl-ethyl)-1H-imidazol-4-yl]-amide;

2-[2-(3,5-Difluoro-phenyl)-2-hydroxy-acetylamino]-pentanoic acid [1-(1,1-dimethyl-2-pyrrolidin-1-yl-ethyl)-1H-imidazol-4-yl]-amide;

2-[2-(3,5-Difluoro-phenyl)-2-hydroxy-acetylamino]-pentanoic acid [1-(1-ethyl-propyl)-1H-imidazol-4-yl]-amide;

2-[2-(4-Phenyl-thiazol-2-yl)-acetylamino]-pentanoic acid [1-(1,1-dimethyl-2-pyrrolidin-1-yl-ethyl)-1H-imidazol-4-yl]-amide;

2-[2-(3-Trifluoromethyl-phenyl)-acetylamino]-pentanoic acid [1-(1,1-dimethyl-2-morpholin-4-yl-ethyl)-1H-imidazol-4-yl]-amide;

2-(2-Hydroxy-3-methyl-butyrylamino)-pentanoic acid [1-(1,1-dimethyl-2-pyrrolidin-1-yl-ethyl)-1H-imidazol-4-yl]-amide;

2-(2-Hydroxy-3,3-dimethyl-butyrylamino)-pentanoic acid [1-(1,1-dimethyl-2-pyrrolidin-1-yl-ethyl)-1H-imidazol-4-yl]-amide;

2-(2-Hydroxy-3-methyl-butyrylamino)-pentanoic acid [1-(1,1-dimethyl-2-morpholin-4-yl-ethyl)-1H-imidazol-4-yl]-amide;

2-[2-(3,5-Difluoro-phenyl)-2-hydroxy-acetylamino]-pentanoic acid [1-(1,1-dimethyl-2-morpholin-4-yl-ethyl)-1H-imidazol-4-yl]-amide;

2-(2-Hydroxy-3,3-dimethyl-butyrylamino)-pentanoic acid [1-(1,1-dimethyl-2-morpholin-4-yl-ethyl)-1H-imidazol-4-yl]-amide;

2-[2-(3,5-Difluoro-phenyl)-acetylamino]-4-methyl-pentanoic acid [1-(1,1-dimethyl-2-pyrrolidin-1-yl-ethyl)-1H-imidazol-4-yl]-amide;

2-[2-(3,5-Difluoro-phenyl)-acetylamino]-N-[1-(1,1-dimethyl-2-pyrrolidin-1-yl-ethyl)-1H-imidazol-4-yl]-propionamide;

(4-{2-[2-(3,5-Difluoro-phenyl)-acetylamino]-pentanoylamino}-imidazol-1-yl)-acetic acid methyl ester;

2-(4-{2-[2-(3,5-Difluoro-phenyl)-acetylamino]-pentanoylamino}-2-methyl-imidazo-1-yl)-2-methyl-propionic acid methyl ester;

2-[2-(3,5-Difluoro-phenyl)-acetylamino]-pentanoic acid [1-(2-methoxy-1,1-dimethyl-ethyl)-1H-imidazol-4-yl]-amide;

4-(4-{2-[2-(3,5-Difluoro-phenyl)-acetylamino]-pentanoylamino}-imidazol-1-yl)-benzoic acid methyl ester;

2-[2-(3,5-Difluoro-phenyl)-acetylamino]-pentanoic acid {1-[1-(2,2-dimethyl-propyl)-pyrrolidin-3-yl]-1H-imidazol-4-yl}-amide;

3-{4-[2-(6,8-Difluoro-1,2,3,4-tetrahydro-naphthalen-2-ylamino)-pentanoylamino]-imidazol-1-yl}-butyric acid methyl ester;

2-{4-[2-(6,8-Difluoro-1,2,3,4-tetrahydro-naphthalen-2-ylamino)-pentanoylamino]-imidazol-1-yl}-2-methyl-propionic acid methyl ester;

2-(6,8-Difluoro-1,2,3,4-tetrahydro-naphthalen-2-ylamino)-pentanoic acid [1-(1-ethyl-propyl)-1H-imidazol-4-yl]-amide;

3-{4-[2-(6,8-Difluoro-1,2,3,4-tetrahydro-naphthalen-2-ylamino)-pentanoylamino]-imidazol-1-yl}-3-methyl-butyric acid methyl ester;

2-[2-(3,5-Difluoro-phenyl)-acetylamino]-pentanoic acid [1-(2-isopropylamino-1,1-dimethyl-ethyl)-1H-imidazol-4-yl]-amide;

2-[2-(3,5-Difluoro-phenyl)-acetylamino]-pentanoic acid [1-(1,1-dimethyl-2-methylamino-ethyl)-1H-imidazol-4-yl]-amide;

2-[2-(3,5-Difluoro-phenyl)-acetylamino]-pentanoic acid [1-(2-benzylamino-1,1-dimethyl-ethyl)-1H-imidazol-4-yl]-amide;

2-[2-(3,5-Difluoro-phenyl)-acetylamino]-pentanoic acid {1-[2-(2,2-dimethyl-propylamino)-1,1-dimethyl-ethyl]-1H-imidazol-4-yl}-amide;

2-[2-(3,5-Difluoro-phenyl)-acetylamino]-pentanoic acid [1-(2-dimethylamino-1,1-dimethyl-ethyl)-1H-imidazol-4-yl]-amide;

2-[2-(3,5-Difluoro-phenyl)-acetylamino]-pentanoic acid {1-[1,1-dimethyl-2-(1-phenyl-ethylamino)-ethyl]-1H-imidazol-4-yl}-amide;

2-[2-(3,5-Difluoro-phenyl)-acetylamino]-pentanoic acid [1-(1,1-dimethyl-3-morpholin-4-yl-propyl)-1H-imidazol-4-yl]-amide;

2-[2-(3,5-Difluoro-phenyl)-acetylamino]-pentanoic acid [1-(1,1-dimethyl-3-pyrrolidin-1-yl-propyl)-1H-imidazol-4-yl]-amide;

2-(6,8-Difluoro-1,2,3,4-tetrahydro-naphthalen-2-ylamino)-pentanoic acid [1-(1,1-dimethyl-2-pyrrolidin-1-yl-ethyl)-1H-imidazol-4-yl]-amide;

2-(5-Chloro-indan-2-ylamino)-pentanoic acid [1-(1,1-dimethyl-2-pyrrolidin-1-yl-ethyl)-1H-imidazol-4-yl]-amide;

2-(Indan-2-ylamino)-pentanoic acid [1-(1,1-dimethyl-2-pyrrolidin-1-yl-ethyl)-1H-imidazol-4-yl]-amide;

2-(6-Fluoro-1,2,3,4-tetrahydro-naphthalen-2-ylamino)-pentanoic acid [1-(1,1-dimethyl-2-pyrrolidin-1-yl-ethyl)-1H-imidazol-4-yl]-amide;

2-(6-Chloro-1,2,3,4-tetrahydro-naphthalen-2-ylamino)-pentanoic acid [1-(1,1-dimethyl-2-pyrrolidin-1-yl-ethyl)-1H-imidazol-4-yl]-amide;

2-(6,8-Dichloro-1,2,3,4-tetrahydro-naphthalen-2-ylamino)-pentanoic acid [1-(1,1-dimethyl-2-pyrrolidin-1-yl-ethyl)-1H-imidazol-4-yl]-amide;

2-(5,7-Dimethyl-1,2,3,4-tetrahydro-naphthalen-2-ylamino)-pentanoic acid [1-(1,1-dimethyl-2-pyrrolidin-1-yl-ethyl)-1H-imidazol-4-yl]-amide;

2-(1,2,3,4-Tetrahydro-naphthalen-2-ylamino)-pentanoic acid [1-(1,1-dimethyl-2-pyrrolidin-1-yl-ethyl)-1H-imidazol-4-yl]-amide;

2-(6-Isopropyl-1,2,3,4-tetrahydro-naphthalen-2-ylamino)-pentanoic acid [1-(1,1-dimethyl-2-pyrrolidin-1-yl-ethyl)-1H-imidazol-4-yl]-amide;

2-[2-(2-Fluoro-phenyl)-1-methyl-ethylamino]-pentanoic acid [1-(1,1-dimethyl-2-pyrrolidin-1-yl-ethyl)-1H-imidazol-4-yl]-amide;

2-[1-Methyl-2-(3-trifluoromethyl-phenyl)-ethylamino]-pentanoic acid [1-(1,1-dimethyl-2-pyrrolidin-1-yl-ethyl)-1H-imidazol-4-yl]-amide;

2-(5,7-Difluoro-1,2,3,4-tetrahydro-naphthalen-2-ylamino)-pentanoic acid [1-(1,1-dimethyl-2-pyrrolidin-1-yl-ethyl)-1H-imidazol-4-yl]-amide;

2-(6-Bromo-1,2,3,4-tetrahydro-naphthalen-2-ylamino)-pentanoic acid [1-(1,1-dimethyl-2-pyrrolidin-1-yl-ethyl)-1H-imidazol-4-yl]-amide;

2-[2-(3,5-Difluoro-phenyl)-ethylamino]-pentanoic acid [1-(1,1-dimethyl-2-pyrrolidin-1-yl-ethyl)-1H-imidazol-4-yl]-amide;

2-[2-(3,5-Difluoro-phenyl)-1-methyl-ethylamino]-pentanoic acid [1-(1,1-dimethyl-2-pyrrolidin-1-yl-ethyl)-1H-imidazol-4-yl]-amide;

2-(6,8-Difluoro-1,2,3,4-tetrahydro-naphthalen-2-ylamino)-pentanoic acid [1-(1-ethyl-propyl)-1H-imidazol-4-yl]-amide;

2-(6,8-Difluoro-1,2,3,4-tetrahydro-naphthalen-2-ylamino)-pentanoic acid [1-(1,1-dimethyl-3-morpholin-4-yl-propyl)-1H-imidazol-4-yl]-amide;

2-(6,8-Difluoro-1,2,3,4-tetrahydro-naphthalen-2-ylamino)-pentanoic acid [1-(1,1-dimethyl-2-morpholin-4-yl-ethyl)-1H-imidazol-4-yl]-amide;

2-[2-(3,5-Difluoro-phenyl)-acetylamino]-pentanoic acid {1-[1,1-dimethyl-2-(1-phenyl-ethylamino)-ethyl]-1H-imidazol-4-yl}-amide;

2-(6,8-Dichloro-1,2,3,4-tetrahydro-naphthalen-2-ylamino)-pentanoic acid [1-(1,1-dimethyl-2-morpholin-4-yl-ethyl)-1H-imidazol-4-yl]-amide;

2-(6,8-Difluoro-1,2,3,4-tetrahydro-naphthalen-2-ylamino)-4-methyl-pentanoic acid [1-(1,1-dimethyl-2-pyrrolidin-1-yl-ethyl)-1H-imidazol-4-yl]-amide;

2-(6,8-Difluoro-1,2,3,4-tetrahydro-naphthalen-2-ylamino)-N-[1-(1,1-dimethyl-2-pyrrolidin-1-yl-ethyl)-1H-imidazol-4-yl]-propionamide;

2-(6,8-Difluoro-1,2,3,4-tetrahydro-naphthalen-2-ylamino)-pentanoic acid [1-(2-dimethylamino-1,1-dimethyl-ethyl)-1H-imidazol-4-yl]-amide;

4-{4-[2-(6,8-Difluoro-1,2,3,4-tetrahydro-naphthalen-2-ylamino)-pentanoylamino]-imidazol-1-yl}-benzoic acid methyl ester;

2-(6,8-Difluoro-1,1-dimethyl-1,2,3,4-tetrahydro-naphthalen-2-ylamino)-pentanoic acid [1-(1,1-dimethyl-2-pyrrolidin-1-yl-ethyl)-1H-imidazol-4-yl]-amide;

2-(6-Isopropyl-1,2,3,4-tetrahydro-naphthalen-2-ylamino)-pentanoic acid [1-(1,1-dimethyl-2-pyrrolidin-1-yl-ethyl)-1H-imidazol-4-yl]-amide;

2-(6,8-Difluoro-1,2,3,4-tetrahydro-naphthalen-2-ylamino)-pentanoic acid [1-(2-hydroxy-1,1-dimethyl-ethyl)-1H-imidazol-4-yl]-amide;

2-[2-(3,5-Difluoro-phenyl)-acetylamino]-pentanoic acid [1-(2-hydroxy-ethyl)-1H-imidazol-4-yl]-amide;

2-[2-(3,5-Difluoro-phenyl)-acetylamino]-pentanoic acid [1-(2-hydroxy-1,1-dimethyl-ethyl)-1H-imidazol-4-yl]-amide;

2-[2-(3,5-Difluoro-phenyl)-acetylamino]-pentanoic acid [1-(3-hydroxy-1,1-dimethyl-propyl)-1H-imidazol-4-yl]-amide;

2-[2-(3,5-Difluoro-phenyl)-acetylamino]-pentanoic acid (1-piperidin-4-yl-1H-imidazol-4-yl)-amide;

2-[2-(3,5-Difluoro-phenyl)-acetylamino]-pentanoic acid [1-(1-methyl-piperidin-4-yl)-1H-imidazol-4-yl]-amide;

2-[2-(3,5-Difluoro-phenyl)-acetylamino]-pentanoic acid [1-(1-acetyl-piperidin-4-yl)-1H-imidazol-4-yl]-amide;

2-[2-(3,5-Difluoro-phenyl)-acetylamino]-pentanoic acid (1-piperidin-4-yl-1H-imidazol-4-yl)-amide;

2-[2-(3,5-Difluoro-phenyl)-acetylamino]-pentanoic acid {1-[1-(3,3-dimethyl-butyryl)-piperidin-4-yl]-1H-imidazol-4-yl}-amide;

2-[2-(3,5-Difluoro-phenyl)-acetylamino]-pentanoic acid {1-[1-(3,3-dimethyl-butyl)-piperidin-4-yl]-1H-imidazol-4-yl}-amide;

2-[2-(3,5-Difluoro-phenyl)-acetylamino]-pentanoic acid {1-[1-(2,2-dimethyl-propyl)-piperidin-4-yl]-1H-imidazol-4-yl}-amide;

2-[6-(4-Fluoro-phenyl)-1,2,3,4-tetrahydro-naphthalen-2-ylamino]-pentanoic acid [1-(1,1-dimethyl-2-pyrrolidin-1-yl-ethyl)-1H-imidazol-4-yl]-amide;

2-[(6,8-Difluoro-1,2,3,4-tetrahydro-naphthalen-2-yl)-methyl-amino]-pentanoic acid [1-(1,1-dimethyl-2-pyrrolidin-1-yl-ethyl)-1H-imidazol-4-yl]-amide;

2-[2-(3,5-Difluoro-phenyl)-acetylamino]-pentanoic acid [7-(2,2-dimethyl-propyl)-5,5-dimethyl-5,6,7,8-tetrahydro-imidazo[1,5-a]pyrazin-1-yl]-amide;

2-(6,8-Difluoro-1,2,3,4-tetrahydro-naphthalen-2-ylamino)-pentanoic acid {1-[2-(2,2-dimethyl-propylamino)-1,1-dimethyl-ethyl]-1H-imidazol-4-yl}-amide;

2-(6,8-Difluoro-1,2,3,4-tetrahydro-naphthalen-2-ylamino)-pentanoic acid [1-(1,1-dimethyl-2-piperidin-1-yl-ethyl)-1H-imidazol-4-yl]-amide;

2-(6,8-Difluoro-1,2,3,4-tetrahydro-naphthalen-2-ylamino)-pentanoic acid [1-(2-dimethylamino-1,1-dimethyl-ethyl)-1H-imidazol-4-yl]-amide;

2-(6,8-Difluoro-1,2,3,4-tetrahydro-naphthalen-2-ylamino)-pentanoic acid {1-[1,1-dimethyl-2-(2,2,2-trifluoro-ethylamino)-ethyl]-1H-imidazol-4-yl}-amide;

2-(6,8-Difluoro-1,2,3,4-tetrahydro-naphthalen-2-ylamino)-pentanoic acid [1-(1,1-dimethyl-2-pyrrolidin-1-yl-ethyl)-1H-imidazol-4-yl]-amide;

2-(6,8-Difluoro-1,2,3,4-tetrahydro-naphthalen-2-ylamino)-pentanoic acid [1-(1,1-dimethyl-2-pyrrolidin-1-yl-ethyl)-1H-imidazol-4-yl]-amide;

2-(6,8-Difluoro-1,2,3,4-tetrahydro-naphthalen-2-ylamino)-pentanoic acid [1-(3-hydroxy-cyclobutyl)-1H-imidazol-4-yl]-amide;

2-(6,8-Difluoro-1,2,3,4-tetrahydro-naphthalen-2-ylamino)-pentanoic acid {1-[2-(2,6-dimethyl-morpholin-4-yl)-1,1-dimethyl-ethyl]-1H-imidazol-4-yl}-amide;

2-(6,8-Difluoro-1,2,3,4-tetrahydro-naphthalen-2-ylamino)-pentanoic acid (1-{2-[(2,2-dimethyl-propyl)-methyl-amino]-1,1-dimethyl-ethyl}-1H-imidazol-4-yl)-amide;

2-(6,8-Difluoro-1,2,3,4-tetrahydro-naphthalen-2-ylamino)-pentanoic acid {1-[1,1-dimethyl-2-(4-methyl-piperazin-1-yl)-ethyl]-1H-imidazol-4-yl}-amide;

2-[2-(3,5-Difluoro-phenyl)-acetylamino]-pentanoic acid [1-(2-morpholin-4-yl-ethyl)-1H-imidazol-4-yl]-amide;

2-[2-(3,5-Difluoro-phenyl)-acetylamino]-pentanoic acid {1-[2-(2,2-dimethyl-propylamino)-ethyl]-1H-imidazol-4-yl}-amide;

2-[2-(3,5-Difluoro-phenyl)-acetylamino]-pentanoic acid {1-[2-(4-methyl-piperazin-1-yl)-ethyl]-1H-imidazol-4-yl}-amide;

2-[2-(3,5-Difluoro-phenyl)-acetylamino]-pentanoic acid [1-(2-hydroxy-1,1,2-trimethyl-propyl)-1H-imidazol-4-yl]-amide;

2-[2-(3,5-Difluoro-phenyl)-acetylamino]-pentanoic acid [1-(3-hydroxy-1,1,3-trimethyl-butyl)-1H-imidazol-4-yl]-amide;

2-[2-(3,5-Difluoro-phenyl)-acetylamino]-pentanoic acid [1-(2-ethyl-2-hydroxy-1,1-dimethyl-butyl)-1H-imidazol-4-yl]-amide;

2-[2-(3,5-Difluoro-phenyl)-acetylamino]-pentanoic acid [1-(3-ethyl-3-hydroxy-1,1-dimethyl-pentyl)-1H-imidazol-4-yl]-amide;

2-[2-(3,5-Difluoro-phenyl)-acetylamino]-pentanoic acid (1-tert-butyl-1H-imidazol-4-yl)-amide;

2-[2-(3,5-Difluoro-phenyl)-2-hydroxy-acetylamino]-pentanoic acid (1-tert-butyl-1H-imidazol-4-yl)-amide;

2-(2-Hydroxy-3,3-dimethyl-butyrylamino)-pentanoic acid (1-tert-butyl-1H-imidazol-4-yl)-amide;

2-(6,8-Difluoro-1,2,3,4-tetrahydro-naphthalen-2-ylamino)-pentanoic acid (1-tert-butyl-1H-imidazol-4-yl)-amide;

2-[2-(3,5-Difluoro-phenyl)-2-hydroxy-acetylamino]-N-(1-isopropyl-1H-imidazol-4-yl)-propionamide;

2-(2-Hydroxy-3,3-dimethyl-butyrylamino)-pentanoic acid (1-isopropyl-1H-imidazol-4-yl)-amide;

2-[2-(3,5-Difluoro-phenyl)-acetylamino]-pentanoic acid {1-[2-(3-hydroxy-pyrrolidin-1-yl)-1,1-dimethyl-ethyl]-1H-imidazol-4-yl}-amide;

2-[2-(3,5-Difluoro-phenyl)-acetylamino]-pentanoic acid {1-[1-(2,2-dimethyl-propyl)-azetidin-3-yl]-1H-imidazol-4-yl}-amide;

2-[2-(3,5-Difluoro-phenyl)-acetylamino]-pentanoic acid {1-[1-(2,2-dimethyl-propionyl)-azetidin-3-yl]-1H-imidazol-4-yl}-amide;

2-[2-(3,5-Difluoro-phenyl)-acetylamino]-pentanoic acid [1-(2-isopropoxy-1,1-dimethyl-ethyl)-1H-imidazol-4-yl]-amide;

2-(6,8-Difluoro-1,2,3,4-tetrahydro-1,4-methano-naphthalen-2-ylamino)-pentanoic acid [1-(1,1-dimethyl-2-morpholin-4-yl-ethyl)-1H-imidazol-4-yl]-amide;

2-(5,7-Difluoro-chroman-3-ylamino)-pentanoic acid [1-(1,1-dimethyl-2-morpholin-4-yl-ethyl)-1H-imidazol-4-yl]-amide;

2-(4,6-Difluoro-tricyclo[6.2.2]dodeca-2(7),3,5-trien-9-ylamino)-pentanoic acid [1-(1,1-dimethyl-2-morpholin-4-yl-ethyl)-1H-imidazol-4-yl]-amide;

2-(Naphthalen-2-ylamino)-pentanoic acid [1-(1,1-dimethyl-2-morpholin-4-yl-ethyl)-1H-imidazol-4-yl]-amide;

2-(Quinolin-3-ylamino)-pentanoic acid [1-(1,1-dimethyl-2-morpholin-4-yl-ethyl)-1H-imidazol-4-yl]-amide;

2-(1-Methyl-1H-indol-3-ylamino)-pentanoic acid [1-(1,1-dimethyl-2-morpholin-4-yl-ethyl)-1H-imidazol-4-yl]-amide;

2-[2-(3,5-Difluoro-phenyl)-acetylamino]-pentanoic acid [1-(1,1-dimethyl-2-pyrrolidin-1-yl-ethyl)-2-trifluoromethyl-1H-imidazol-4-yl]-amide;

2-[2-(3,5-Difluoro-phenyl)-acetylamino]-pentanoic acid [1-(1,1-dimethyl-2-pyrrolidin-1-yl-ethyl)-2-fluoro-1H-imidazol-4-yl]-amide;

2-[2-(3,5-Difluoro-phenyl)-acetylamino]-pentanoic acid [1-(1,1-dimethyl-2-pyrrolidin-1-yl-ethyl)-2-phenyl-1H-imidazol-4-yl]-amide;

2-[2-(3,5-Difluoro-phenyl)-acetylamino]-pentanoic acid [1-(1,1-dimethyl-2-pyrrolidin-1-yl-ethyl)-5-phenyl-1H-imidazol-4-yl]-amide;

2-[2-(3,5-Difluoro-phenyl)-acetylamino]-pentanoic acid [1-(1,1-dimethyl-2-pyrrolidin-1-yl-ethyl)-5-trifluoromethyl-1H-imidazol-4-yl]-amide;

5-{2-[2-(3,5-Difluoro-phenyl)-acetylamino]-pentanoylamino}-3-(1,1-dimethyl-2-pyrrolidin-1-yl-ethyl)-3H-imidazole-4-carboxylic acid methyl ester;

2-[2-(3,5-Difluoro-phenyl)-acetylamino]-pentanoic acid (6,6-dimethyl-5,6,7,8-tetrahydro-imidazo[1,5-a]pyridin-1-yl)-amide;

2-[2-(3,5-Difluoro-phenyl)-acetylamino]-pentanoic acid (6-methyl-5,6,7,8-tetrahydro-imidazo[1,2-a]pyridin-2-yl)-amide;

2-[2-(3,5-Difluoro-phenyl)-acetylamino]-pentanoic acid (3,4-dihydro-2H-imidazo[5,1-b][1,3]oxazin-8-yl)-amide;

2-[2-(3,5-Difluoro-phenyl)-acetylamino]-pentanoic acid (1H-imidazo[1,2-a]pyridin-3-yl)-amide;

2-[2-(3,5-Difluoro-phenyl)-ethylamino]-pentanoic acid [1-(1,1-dimethyl-2-pyrrolidin-1-yl-ethyl)-1H-imidazol-4-yl]-amide;

2-[2-(3,5-Difluoro-phenyl)-2-hydroxy-ethylamino]-pentanoic acid [1-(1,1-dimethyl-2-pyrrolidin-1-yl-ethyl)-1H-imidazol-4-yl]-amide;

2-[2-(3,5-Difluoro-phenyl)-1-methyl-ethylamino]-pentanoic acid [1-(1,1-dimethyl-2-pyrrolidin-1-yl-ethyl)-1H-imidazol-4-yl]-amide;

2-(3,5-Difluoro-benzylamino)-pentanoic acid [1-(1,1-dimethyl-2-pyrrolidin-1-yl-ethyl)-1H-imidazol-4-yl]-amide;

2-(6,8-Difluoro-1,2,3,4-tetrahydro-naphthalen-2-ylamino)-pentanoic acid [1-(1-dimethylaminomethyl-cyclopentyl)-1H-imidazol-4-yl]-amide; and 2-(6,8-Difluoro-1-hydroxy-1,2,3,4-tetrahydro-naphthalen-2-ylamino)-pentanoic acid [1-(1,1-dimethyl-2-pyrrolidin-1-yl-ethyl)-1H-imidazol-4-yl]-amide.

Compounds of the Formula I of this invention, and their pharmaceutically acceptable salts, have useful pharmaceutical and medicinal properties. The compounds of Formula I, and their pharmaceutically acceptable salts inhibit the production of Aβ-peptide (thus, gamma-secretase activity) in mammals, including humans. Compounds of the Formula I, and their pharmaceutically acceptable salts, are therefore able to function as therapeutic agents in the treatment of the neurodegenerative and/or neurological disorders and diseases representatively enumerated below, for example Alzheimer's disease, in an afflicted mammal, including a human.

The present invention also relates to a pharmaceutical composition for inhibiting Aβ-peptide production in a mammal, including a human, comprising an amount of a compound of the Formula I, or a pharmaceutically acceptable salt thereof, that is effective in inhibiting Aβ-production, and a pharmaceutically acceptable carrier.

The present invention also relates to a pharmaceutical composition for treating a disease or condition selected from the group consisting of Alzheimer's disease, hereditary cerebral hemorrhage with amyloidosis, cerebral amyloid angiopathy, a prion-mediated disease, inclusion body myositis, stroke, multiple sclerosis, head trauma, mild cognitive impairment and Down's Syndrome in a mammal, including a human, comprising an amount of a compound of the Formula I, or a pharmaceutically acceptable salt thereof, that is effective in inhibiting Aβ-peptide production, and a pharmaceutically acceptable carrier.

The present invention also relates to a pharmaceutical composition for treating a disease or condition selected from the group consisting of Alzheimer's disease and Down's Syndrome in a mammal, including a human, comprising an amount of a compound of the Formula I, or a pharmaceutically acceptable salt thereof, that is effective in inhibiting Aβ-peptide production, and a pharmaceutically acceptable carrier.

The present invention also relates to a pharmaceutical composition for treating a disease or a condition selected from the group consisting of Alzheimer's disease, hereditary cerebral hemorrhage with amyloidosis, cerebral amyloid angiopathy, a prion-mediated disease, inclusion body myositis, stroke, multiple sclerosis, head trauma, mild cognitive impairment and Down's Syndrome in a mammal, including a human, comprising an amount of a compound of the Formula I, or a pharmaceutically acceptable salt thereof, that is effective in treating such disease or condition, and a pharmaceutically acceptable carrier.

The present invention also relates to a pharmaceutical composition for treating a disease or a condition selected from the group consisting of Alzheimer's disease and Down's Syndrome in a mammal, including a human, comprising an amount of a compound of the Formula I, or a pharmaceutically acceptable salt thereof, that is effective in treating such disease or condition, and a pharmaceutically acceptable carrier.

The present invention also relates to a method of inhibiting Aβ-peptide production in a mammal, including a human, comprising administering to said mammal an amount of a compound of the Formula I, or a pharmaceutically acceptable salt thereof, that is effective in inhibiting Aβ-production.

The present invention also relates to a method of treating a disease or condition selected from Alzheimer's disease, hereditary cerebral hemorrhage with amyloidosis, cerebral amyloid angiopathy, a prion-mediated disease, inclusion body myositis, stroke, multiple sclerosis, head trauma, mild cognitive impairment and Down's Syndrome in a mammal, including a human, comprising administering to said mammal an amount of a compound of the Formula I, or a pharmaceutically acceptable salt thereof, that is effective in inhibiting Aβ-production.

The present invention also relates to a method of treating a disease or condition selected from Alzheimer's disease and Down's Syndrome in a mammal, including a human, comprising administering to said mammal an amount of a compound of the Formula I, or a pharmaceutically acceptable salt thereof, that is effective in inhibiting Aβ-production.

The present invention also relates to a method of treating a disease or condition selected from Alzheimer's disease, hereditary cerebral hemorrhage with amyloidosis, cerebral amyloid angiopathy, a prion-mediated disease, inclusion body myositis, stroke, multiple sclerosis, head trauma, mild cognitive impairment and Down's Syndrome in a mammal, including a human, comprising administering to said mammal an amount of a compound of the Formula I, or a pharmaceutically acceptable salt thereof, that is effective in treating such condition.

The present invention also relates to a method of treating a disease or condition selected from Alzheimer's disease and Down's Syndrome in a mammal, including a human, comprising administering to said mammal an amount of a compound of the Formula I, or a pharmaceutically acceptable salt thereof, that is effective in treating such condition.

The compounds of Formula I may be used alone or used in combination with any other drug, including, but not limited to, any memory enhancement agent, e.g., Aricept™ and/or Namenda™, antidepressant agent, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, Caduet™, etc., Histamine (H2) antagonist, e.g., Cimetadine™, and anti-hypertension agent, e.g., Norvasc™, Caduet™, etc. Accordingly, the present invention also relates to the following pharmaceutical compositions and methods of treatment comprising a compound of the Formula I in combination with other drugs, such as those of the type described above.

The present invention also relates to a pharmaceutical composition for treating a disease or condition associated with Aβ-peptide production in a mammal, including a human, comprising (a) a compound of the Formula I, or a pharmaceutically acceptable salt thereof; (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, Caduet™, etc., Histamine (H2) antagonist, e.g., Cimetadine™, and anti-hypertensive agent, e.g., Norvasc™, Caduet™, etc.; and (c) a pharmaceutically acceptable carrier; wherein the active agents "a"

and "b" above are present in amounts that render the composition effective in treating such disease or condition.

The present invention also relates to a pharmaceutical composition for treating a disease or condition selected from the group consisting of Alzheimer's disease, hereditary cerebral hemorrhage with amyloidosis, cerebral amyloid angiopathy, a prion-mediated disease, inclusion body myositis, stroke, multiple sclerosis, head trauma, mild cognitive impairment and Down's Syndrome, in a mammal, including a human, comprising (a) a compound of the Formula I, or a pharmaceutically acceptable salt thereof; (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, Caduet™, etc., Histamine (H2) antagonist, e.g., Cimetadine™, and anti-hypertensive agent, e.g., Norvasc™, Caduet™, etc.; and (c) a pharmaceutically acceptable carrier; wherein the active agents "a" and "b" above are present in amounts that render the composition effective in treating such disease or condition.

The present invention also relates to a pharmaceutical composition for treating a disease or condition selected from the group consisting of Alzheimer's disease and Down's Syndrome, in a mammal, including a human, comprising (a) a compound of the Formula I, or a pharmaceutically acceptable salt thereof; (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, Caduet™, etc., Histamine (H2) antagonist, e.g., Cimetadine™, and anti-hypertensive agent, e.g., Norvasc™, Caduet™, etc.; and (c) a pharmaceutically acceptable carrier; wherein the active agents "a" and "b" above are present in amounts that render the composition effective in treating such disease or condition.

The present invention also relates to a method of treating a disease or condition associated with Aβ-peptide production in a mammal, including a human, comprising administering to said mammal (a) a compound of the Formula I, or a pharmaceutically acceptable salt thereof; and (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, Caduet™, etc., Histamine (H2) antagonist, e.g., Cimetadine™, and anti-hypertensive agent, e.g., Norvasc™, Caduet™, etc.; wherein the active agents "a" and "b" above are present in amounts that render the composition effective in treating such disease or condition.

The present invention also relates to a method of treating a disease or condition selected from the group consisting of Alzheimer's disease, hereditary cerebral hemorrhage with amyloidosis, cerebral amyloid angiopathy, a prion-mediated disease, inclusion body myositis, stroke, multiple sclerosis, head trauma, mild cognitive impairment and Down's Syndrome, in a mammal, including a human, comprising administering to said mammal (a) a compound of the Formula I, or a pharmaceutically acceptable salt thereof; and (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, Caduet™, etc., Histamine (H2) antagonist, e.g., Cimetadine™, and anti-hypertensive agent, e.g., Norvasc™, Caduet™, etc.; wherein the active agents "a" and "b" above are present in amounts that render the composition effective in treating such disease or condition.

The present invention also relates to a method of treating a disease or condition selected from the group consisting of Alzheimer's disease and Down's Syndrome, in a mammal, including a human, comprising administering to said mammal (a) a compound of the Formula I, or a pharmaceutically acceptable salt thereof; and (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™, Caduet™, etc., Histamine (H2) antagonist, e.g., Cimetadine™, and anti-hypertensive agent, e.g., Novasc™; Caduet™, etc.; wherein the active agents "a" and "b" above are present in amounts that render the composition effective in treating such disease or condition.

Compounds of the Formula I, or any of the combinations described in the immediately preceding paragraphs, may optionally be used in conjunction with a known P-glycoprotein inhibitor, such as verapamil.

References herein to diseases and conditions "associated with Aβ-peptide production" relate to diseases or conditions that are caused, at least in part, by Aβ-peptide and/or the production thereof. Thus, Aβ-peptide is a contributing factor, but not necessarily the only contributing factor, to "a disease or condition associated with Aβ-peptide production."

The compounds of Formula I, or their pharmaceutically acceptable salts may also be used to modulate or inhibit the Notch signaling pathway in organisms, including humans. The Notch signaling pathway is an evolutionarily conserved mechanism utilized by organisms, ranging from worms through humans, to regulate fate determination of various cell lineages. Notch belongs to the family of epidermal growth factor-like homeotic genes, which encode transmembrane proteins with variable numbers of epidermal growth factor-like repeats in the extracellular domain. There is increasing evidence for a role of the Notch pathway in human disease. All of the components of the pathway have yet to be identified, but among those identified to date, mutations that affect their interaction with each other can lead to a variety of syndromes and pathological conditions.

For example, Notch signaling is typically associated with cell fate decision. The finding that Notch activation stimulates capillary outgrowth suggests that Notch receptors must be activated to allow this process to occur. Therefore, Notch modulation provides a method for regulating angiogenesis. Specifically, modulation of Notch signaling can be used to modulate angiogenesis (e.g., by blocking Notch signaling to block angiogenesis). This inhibition of angiogenesis in vivo can be used as a therapeutic means to treat a variety of diseases, including but not limited to cancer, diabetic retinopathy, rheumatoid arthritis, psoriasis, inflammatory bowel disease and arteriosclerosis.

The Notch pathway is also implicated in the development and maturation of T cells, as described in Radtke, F. et al., Immunity 10:547-558, 1999. The compounds of Formula I, and their pharmaceutically acceptable salts are therefore useful candidates for modulating the immune system, including the treatment of inflammation, asthma, graft rejection, graft versus host disease, autoimmune disease and transplant rejection.

In addition, a number of studies published between 2002 and 2004 have provided convincing evidence that Notch signaling is frequently elevated in a variety of human tumors (including, but not limited to breast, prostate, pancreas and T-cell acute lymphoblastic leukemia). One key study provides a strong genetic link to Notch's role in important tumor types. Specifically, Weijzen et al. demonstrated that Notch signaling maintains the neoplastic phenotype in human Ras-transformed cells. Weijzen et al. (2002) *Nature Med* 8: 979. Because 30% of human malignancies may carry activating mutations in at least one of the three isoforms of Ras, this finding raises the possibility that Notch inhibitors would be a powerful addition to anti-cancer therapy. Another study's findings support a central role for aberrant Notch signaling in the pathogenesis of human T cell acute lymphoblastic leukemia/lymphoma. Pear et al., *Current Opinion in Hematology* (2004), 11(6), 426-433.

Accordingly, the compounds of Formula I, or their pharmaceutically acceptable salts, may be used for treating a disease or condition selected from the group consisting of cancer, arteriosclerosis, diabetic retinopathy, rheumatoid arthritis, psoriasis, inflammatory bowel disease inflammation, asthma, graft rejection, graft versus host disease, autoimmune disease and transplant rejection.

As used herein, the term "treating" refers to reversing, alleviating or inhibiting the progress of a disease, disorder or condition, or one or more symptoms of such disease, disorder or condition, to which such term applies. As used herein, "treating" may also refer to decreasing the probability or incidence of the occurrence of a disease, disorder or condition in a mammal as compared to an untreated control population, or as compared to the same mammal prior to treatment. For example, as used herein, "treating" may refer to preventing a disease, disorder or condition, and may include delaying or preventing the onset of a disease, disorder or condition, or delaying or preventing the symptoms associated with a disease, disorder or condition. As used herein, "treating" may also refer to reducing the severity of a disease, disorder or condition or symptoms associated with such disease, disorder or condition prior to a mammal's affliction with the disease, disorder or condition. Such prevention or reduction of the severity of a disease, disorder or condition prior to affliction relates to the administration of the composition of the present invention, as described herein, to a subject that is not at the time of administration afflicted with the disease, disorder or condition. As used herein "treating" may also refer to preventing the recurrence of a disease, disorder or condition or of one or more symptoms associated with such disease, disorder or condition. The terms "treatment" and "therapeutically," as used herein, refer to the act of treating, as "treating" is defined above.

DETAILED DESCRIPTION OF THE INVENTION

Compounds of the Formula I, and their pharmaceutically acceptable salts, may be prepared as described in the following reaction Schemes and discussion. Unless otherwise indicated, as referred to in the reaction schemes and discussion that follow, $R^1$, $R^2$, $R^3$, $R^4$, $R^6$, $R^7$, $R^8$, $R^9$, $R^{10}$, $R^{11}$, A, Z and n are as defined above.

The compounds of Formula I may have asymmetric carbon atoms and may therefore exist as racemic mixtures, diasteroisomers, or as individual optical isomers.

Separation of a mixture of isomers of compounds of Formula I into single isomers may be accomplished according to conventional methods known in the art.

The compounds of the Formula I may be prepared by the methods described below, together with synthetic methods known in the art of organic chemistry, or modifications and derivatisations that are familiar to those of ordinary skill in the art. Preferred methods include, but are not limited to, those described below.

The reactions described below are performed in solvents that are appropriate to the reagents and materials employed and that are suitable for use in the reactions described. In the description of the synthetic methods described below, it is also to be understood that all reaction conditions, whether actual or proposed, including choice of solvent, reaction temperature, reaction duration time, reaction pressure, and other reaction conditions (such as anhydrous conditions, under argon, under nitrogen, etc.), and work up procedures, are those conditions that are standard for that reaction, as would be readily recognized by one of skill in the art. Alternate methods may also be used.

Compounds of formula II wherein $R^7$ contains an alcohol moiety may be oxidized using standard oxidation method known in art, such as, e.g., Dess-Martin reagents, Swern oxidation, or use of $SO_3$-pyridine, $CrO_3$, to provide compounds of formula II wherein $R^7$ contains a ketone or aldehyde. Compounds of formula II wherein $R^7$ is a ketone or aldehyde may convert to the corresponding compounds of formula II wherein $R^7$ is an imine (by reaction with an amine), olefin (by a Wittig reaction), alcohol (by a Grignard reaction), or other derivative (by standard reactions).

The compounds of formula I of the present invention and their salts can be prepared by a reaction process comprising a compound of formula II

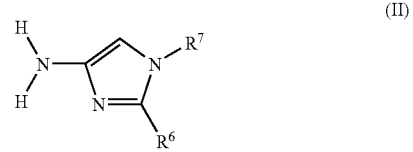

(II)

with a compound of formula III

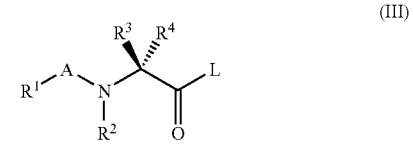

(III)

or reacting a compound of formula IV

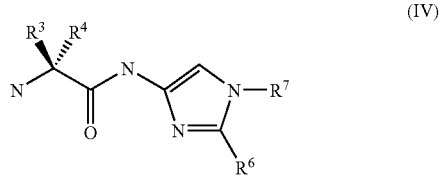

(IV)

with a compound of formula V

(V)

wherein $R^1$, $R^3$, $R^4$, $R^6$, $R^7$, and A are as defined above and L is hydroxy or a suitable leaving group. If desired, the 4-amino-imidazole derivative of formula I or synthetic intermediate of formula IV may be converted into a salt by methods known to those of ordinary skill in the art.

Examples of specific compounds of formula III and V wherein L is hydroxy or a suitable leaving group are those wherein L represents a halogen atom, such as Cl, Br, or I, or A-L is an alkyl or aryl ester.

Compounds in formula I can be prepared by reacting a compound of formula II and a carboxylic acid of formula III, or a compound of formula IV with a compound of formula V. Compounds of formula IV can be prepared by reacting a compound of formula II with a compound of formula VI.

The reaction between compounds of formula II and compounds of formula III, between compounds of formula IV and compounds of formula V, and between compounds of formula II and compounds of formula VI, can be carried out by standard methods. For example, when L is a hydroxy group, these reactions can be carried out in the presence of a coupling agent or a polymer supported coupling agent, such as, for example, carbodiimide, i.e. 1,3-dicyclohexylcarbodiimide (DCC), 1,3-diisopropylcarbodiimide, 1-(3-dimethylamino-propyl)-3-ethylcarbodiimide (EDC), N-cyclohexylcarbodiimide, or N'-methylpolystyrene in the presence or absence of HOBt, in a suitable solvent such as, for instance, a single solvent or a combination of several solvents selected from dichloromethane ($CH_2Cl_2$), chloroform ($CHCl_3$), tetrahydrofuran (THF), diethyl ether ($Et_2O$), 1,4-dioxane, acetonitrile, ($CH_3CN$), toluene, N,N-dimethylformamide (DMF), or dimethylsulfoxide (DMSO), at a suitable temperature such as from about $-10°$ C. to about reflux, for a suitable time monitored by chromatography or LC-MS. An alternative method wherein L is OH is carried out by converting OH to a leaving group by reaction with oxalyl chloride, thionyl chloride or a mixed anhydride method, using an alkyl chloroformate, such as $C_1$-$C_4$ alkyl chloroformate, in the presence of a base such as triethylamine, N,N-diisopropylethylamine, pyridine, or dimethylaminopyridine, in a suitable solvent such as, for example, methylene chloride, chloroform, tetrahydrofuran (THF), toluene, diethyl ether, acetonitrile, 1,4-dioxane, n,N-dimethylformamide, dimethylsulfoxide (DMSO), N-methylpyrrolidinone (NMP), or xylene, at a temperature of from about $-30°$ C. to about room temperature.

Alternatively, aminoimidazole coupling may be achieved as follows. A compound of formula I may be prepared by coupling an amino-imidazole II with III wherein C(=O)L is an ester, in the presence of trialkylaluminium preferably trimethylaluminum in an appropriate solvent such as methylene chloride, THF, dioxane, toluene, etc., at an appropriate temperature, such as from about room temperature to about reflux, or in a sealed reactor (such as sealed tube or inscrewed vials). Similarly, compound IV may be prepared by reacting an amino-imidazole II, triamethylaluminum and N-Boc of an alpha-amino acid ester, followed by removal of the Boc group using standard methods.

The protected amino compounds of formula VI, where $P^1$ is a blocking group such as an N-Boc group, can be prepared by methods well known in the literature, for example the methods described in Theodora W. Greene's book "Protective Groups in Organic Synthesis". Compounds of formula IV can be prepared in an analogous method as above by reacting compound of formula II with a compound of formula VI, followed by deblocking the $P^1$ group. Deprotection can be performed by well-known methods, for example when $P^1$ is N-Boc, removal by any methods well-known in the literature, for example HCl(g) in an appropriate solvent such as 1,4-dioxane, diethylether or trifluoroacetic acid in methylene chloride. Many other amino protecting groups are known and may also be used, such as benzyl or p-methoxy-benzyl, trimethylsilyl, t-butyldimethylsilyl, etc. Methods for deblocking such groups are also well-known in the literature and may be used.

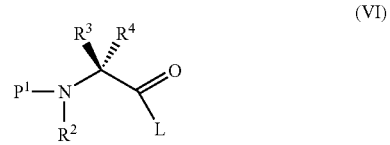
(VI)

The compounds of formula II, III, IV, V and VI, in certain circumstances, are known compounds or can be obtained according to methods well known to one of skill in the art.

Compounds of formula III and V, wherein L is a leaving group as defined above, can be obtained according to conventional methods from the corresponding carboxylic acids of formula III where X is hydroxy.

Compounds of formula IV can be prepared by reacting a compound of formula II with a compound of formula V using known methods.

An ester group of $R^7$ in compounds of formula I or II may be converted to the corresponding amide using a similar method for amide bond formation, preferably employing trimethylaluminum in an appropriate solvent or a mixture of solvents, such as THF/toluene.

A keto group of $R^7$ in compounds of formula I or II may be converted to the corresponding amine using a well-established reductive amination method by reacting such ketone with an appropriate amine, with or without acid catalyst/ammonium acetate/dry agents (such as anhydrous $Na_2SO_4$ or $MgSO_4$), and a reducing agent, such as sodium triacetoxy borohydride, sodium cyanoborohydride, or sodium borohydride, or the corresponding polymer bound-$NaBH_4$, polymer bound-$NaBH_3CN$, or polymer bound-$NaB(OAc)_3H$, or any reducing agent (e.g., hydrogenation) that is known in the literature for reducing an imine bond to an amine, in an appropriate solvent, such as dichloroethane, chloroform, THF, MeOH, ethanol, isopropanol, t-butanol or toluene, at a temperature from about room temperature to about reflux, preferably from about room temperature to about $65°$ C.

Compounds wherein $R^6$ is a halo group may be generated by reacting the starting material wherein $R^6$ is H with NBS (N-bromosuccinamide), NCS(N-chlorosuccinamide), or $SO_2Cl_2$, $I_2$ in an appropriate solvent such as methylene chloride, carbontetrachloride or chloroform. The halo group may then be replaced with another group using methods known in the art, such as halogen-metal exchange, followed by quenching with an electrophile, or using typical Suzuki coupling conditions employing a catalyst such as a palladium complex, e.g., tetrakis(triphenylphosphine)-palladium, with sodium carbonate as a base, in a suitable solvent such as THF, DME, or ethanol, and a boronic acid.

4-amino-imidazole II may be prepared by the following methods known in the chemical literature (e.g., Tetrahedron, 1995, 51, 2875-2894; J. Chem. Soc. Perkin 1, 1987, 2819-2828; Bull. Chem. Soc. Fr. 1994, 131, 200-209; Tetrahedron Lett. 1996, 4423-4426; Tetrahedron 1996, 37, 4423-4426;

Tetrahedron, 1994, 50, 5741-5752; Heterocycles, 1994, 37, 1511-1520; Tetrahedron Lett. 1999, 1623-1626; Organic Lett. 2002, 4, 4133-4134; Organic Lett. 2000, 2, 1233-1236; J. Med. Chem. 1990, 33, 1091-1097; or by the methods described below.

Scheme 1 illustrates methods suitable for preparing aminoimidazole compounds of formula I. Referring to Scheme 1, treatment of a solution of 1,4-dinitroimidazole (*J. Phys. Chem.* (1995) Vol. 99, pp. 5009-5015) in dimethylsulfoxide (DMSO), pyridine-water, water, an alcohol, or an alcohol-water solvent system, but preferably in a lower alcohol such as methanol, from about −20° C. to about 50° C., preferably from about −5° C. to 35° C., with a primary alkyl or aryl amine ($NR^9R^{10}$) affords 1-N-substituted-4-nitroimidazoles of formula 2A. 1,4-dinitroimidazole is a highly energetic, semi-stable substance and should be stored in a freezer at all times it is not in use. Thermodynamic measurements have shown that it can potentially generate enough energy at 35° C. under adiabatic conditions to violently explode. Extreme caution should be exercised at all time using this material. Reduction of the nitro compound of formula 2A to the amine of formula 3A may be accomplished by exposing a mixture of a compound of formula 2A and a noble metal catalyst, in a solvent such as ethyl acetate, tetrahydrofuran, dioxane, or a mixture thereof, to an atmosphere of hydrogen gas at a pressure of about 1 to 100 atmospheres, where a preferred pressure of hydrogen gas is about one to about ten atmospheres. Palladium is the preferred noble metal catalyst. The metal may be conveniently suspended on an inert solid support such as charcoal and filtered to provide the amine of formula 3A. Alternatively, the nitro group of formula 2A to the amine of formula 3A may be accomplished by exposing a mixture of a compound of formula 2A to zinc/HCl or iron/HCl or with $NaBH_4/NiCl_2$ or with $NaBH_2S_3$.

The resulting amine of formula 3A is reacted immediately with an acid chloride, acid anhydride, or an activated carboxylic acid derivative (defined by Formula III), in the presence of a base, such as triethylamine, diisopropylethylamine, pyridine, or 2,6-lutidine, from about −78° C. to 40° C. The reaction between compounds of formula 3A and compounds of formula III can be carried out by standard methods. For example, wherein L of formula III is a hydroxy group, these reactions can be carried out in the presence of a coupling agent or a polymer supported coupling agent, such as, for example, carbodiimide, i.e. 1,3-dicyclohexylcarbodiimide (DCC), 1,3-diisopropylcarbodiimide, 1-(3-dimethylaminopropyl)-3-ethylcarbodiimide (EDC), N-cyclohexylcarbodiimide, or N'-methylpolystyrene in the presence or absence of HOBt, in a suitable solvent such as, for instance, a single solvent or a combination of several solvents selected from dichloromethane ($CH_2Cl_2$), chloroform ($CHCl_3$), tetrahydrofuran (THF), diethyl ether ($Et_2O$), 1,4-dioxane, acetonitrile, ($CH_3CN$), toluene, N,N-dimethylformamide (DMF), or dimethylsulfoxide (DMSO), at a suitable temperature such as from about −10° C. to about reflux, for a suitable time monitored by chromatography or LC-MS. An alternative method wherein L is OH is carried out by converting OH to a leaving group by reaction with oxalyl chloride, thionyl chloride or a mixed anhydride method, using an alkyl chloroformate, such as $C_1$-$C_4$ alkyl chloroformate, in the presence of a base such as triethylamine, N,N-diisopropylethylamine, pyridine, or dimethylaminopyridine, in a suitable solvent such as, for example, methylene chloride, chloroform, tetrahydrofuran (THF), toluene, diethyl ether, acetonitrile, 1,4-dioxane, N,N-dimethylformamide, dimethylsulfoxide (DMSO), N-methylpyrrolidinone (NMP), or xylene, at a temperature of from about −30° C. to about room temperature.

Alternatively, aminoimidazole coupling may be achieved as follows. A compound of formula I may be prepared by coupling an amino-imidazole 3A with a compound of formula III wherein C(=O)L is an ester, in the presence of trialkylaluminium preferably trimethylaluminum in an appropriate solvent such as methylene chloride, THF, dioxane, toluene, etc., at an appropriate temperature, such as from about room temperature to about reflux, or in a sealed reactor (such as sealed tube or inscrewed vials).

Alternatively, the resulting amine of formula 3A is reacted immediately with an acid chloride, acid anhydride, or an activated carboxylic acid derivative (defined by Formula IV), in the presence of a base, such as triethylamine, diisopropylethylamine, pyridine, or 2,6-lutidine, from about −78° C. to 40° C. to form a compound of formula 4A. The reaction between compounds of formula 3A and compounds of formula IV can be carried out by standard methods. For example, wherein L of formula IV is a hydroxy group, these reactions can be carried out in the presence of a coupling agent or a polymer supported coupling agent, such as, for example, carbodiimide, i.e. 1,3-dicyclohexylcarbodiimide (DCC), 1,3-diisopropylcarbodiimide, 1-(3-dimethylaminopropyl)-3-ethylcarbodiimide (EDC), N-cyclohexylcarbodiimide, or N'-methylpolystyrene in the presence or absence of HOBt, in a suitable solvent such as, for instance, a single solvent or a combination of several solvents selected from dichloromethane ($CH_2Cl_2$), chloroform ($CHCl_3$), tetrahydrofuran (THF), diethyl ether ($Et_2O$), 1,4-dioxane, acetonitrile, ($CH_3CN$), toluene, N,N-dimethylformamide (DMF), or dimethylsulfoxide (DMSO), at a suitable temperature such as from about −10° C. to about reflux, for a suitable time monitored by chromatography or LC-MS. An alternative method wherein L is OH is carried out by converting OH to a leaving group by reaction with oxalyl chloride, thionyl chloride or a mixed anhydride method, using an alkyl chloroformate, such as $C_1$-$C_4$ alkyl chloroformate, in the presence of a base such as triethylamine, N,N-diisopropylethylamine, pyridine, or dimethylaminopyridine, in a suitable solvent such as, for example, methylene chloride, chloroform, tetrahydrofuran (THF), toluene, diethyl ether, acetonitrile, 1,4-dioxane, N,N-dimethylformamide, dimethylsulfoxide (DMSO), N-methyl pyrrolidinone (NMP), or xylene, at a temperature of from about −30° C. to about room temperature.

Alternatively, aminoimidazole coupling may be achieved as follows. A compound of formula 4A may be prepared by coupling an amino-imidazole 3A with a compound of formula IV wherein C(=O)L is an ester, in the presence of trialkylaluminium preferably trimethylaluminum in an appropriate solvent such as methylene chloride, THF, dioxane, toluene, etc., at an appropriate temperature, such as from about room temperature to about reflux, or in a sealed reactor (such as sealed tube or inscrewed vials). The protected amino compounds defined as PG, such as a compound with an Boc group, of formula IV can be prepared by methods well known in the literature, for example the methods described in Theodora W. Greene's book "Protective Groups in Organic Synthesis".

Compounds defined as by Formula 5A can be prepared from compounds of formula 4A by deblocking the PG group. Deprotection can be performed by well-known methods, for example when PG is N-Boc, removal by any methods well-known in the literature, for example HCl(g) in an appropriate solvent such as 1,4-dioxane, diethylether or trifluoroacetic acid in methylene chloride. Many other amino protecting groups are known and may also be used, such as benzyl or p-methoxy-benzyl, trimethylsilyl, t-butyldimethylsilyl, etc.

Methods for deblocking such groups are also well-known in the literature and may be used.

Compounds of the Formula I can be formed by reaction between compounds of formula 5A and compounds of formula V can be carried out by standard methods. For example, wherein L is a hydroxy group, these reactions can be carried out in the presence of a coupling agent or a polymer supported coupling agent, such as, for example, carbodiimide, i.e. 1,3-dicyclohexylcarbodiimide (DCC), 1,3-diisopropylcarbodiimide, 1-(3-dimethylaminopropyl)-3-ethylcarbodiimide (EDC), N-cyclohexylcarbodiimide, or N'-methylpolystyrene in the presence or absence of HOBt, in a suitable solvent such as, for instance, a single solvent or a combination of several solvents selected from dichloromethane ($CH_2Cl_2$), chloroform ($CHCl_3$), tetrahydrofuran (THF), diethyl ether ($Et_2O$), 1,4-dioxane, acetonitrile, ($CH_3CN$), toluene, N,N-dimethylformamide (DMF), or dimethylsulfoxide (DMSO), at a suitable temperature such as from about $-10°$ C. to about reflux, for a suitable time monitored by chromatography or LC-MS. An alternative method wherein L is OH is carried out by converting OH to a leaving group by reaction with oxalyl chloride, thionyl chloride or a mixed anhydride method, using an alkyl chloroformate, such as $C_1$-$C_4$ alkyl chloroformate, in the presence of a base such as triethylamine, N,N-diisopropylethylamine, pyridine, or dimethylaminopyridine, in a suitable solvent such as, for example, methylene chloride, chloroform, tetrahydrofuran (THF), toluene, diethyl ether, acetonitrile, 1,4-dioxane, n,N-dimethylformamide, dimethylsulfoxide (DMSO), N-methylpyrrolidinone (NMP), or xylene, at a temperature of from about $-30°$ C. to about room temperature.

Alternatively, aminoimidazole coupling may be achieved as follows. A compound of formula I may be prepared by coupling an amino-imidazole 5A with V wherein L is an ester, in the presence of trialkylaluminium preferably trimethylaluminum in an appropriate solvent such as methylene chloride, THF, dioxane, toluene, etc., at an appropriate temperature, such as from about room temperature to about reflux, or in a sealed reactor (such as sealed tube or inscrewed vials).

Alternatively, compounds of the Formula I can be formed by reaction between compounds of formula 5A and compounds of formula V when L is an aldehyde or ketone by using a well-established reductive amination method by reacting such ketone or aldehyde with an appropriate amine 5A, with or without acid catalyst/ammonium acetate/dry agents (such as anhydrous $Na_2SO_4$ or $MgSO_4$), and a reducing agent, such as sodium triacetoxy borohydride, sodium cyanoborohydride, or sodium borohydride, or the corresponding polymer bound-$NaBH_4$, polymer bound-$NaBH_3CN$, or polymer bound-$NaB(OAc)_3H$, or any reducing agent (e.g., hydrogenation) that is known in the literature for reducing an imine bond to an amine, in an appropriate solvent, such as dichloroethane, chloroform, THF, MeOH, ethanol, isopropanol, t-butanol or toluene, at a temperature from about room temperature to about reflux, preferably from about room temperature to about $65°$ C.

Scheme 1

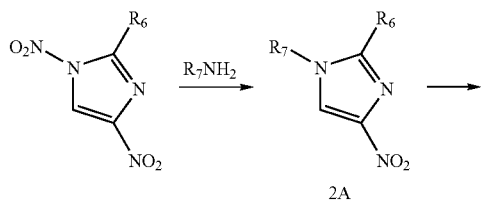

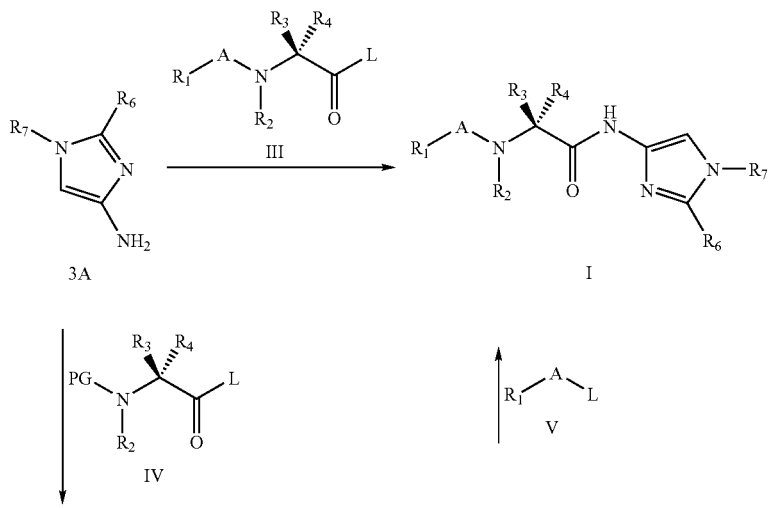

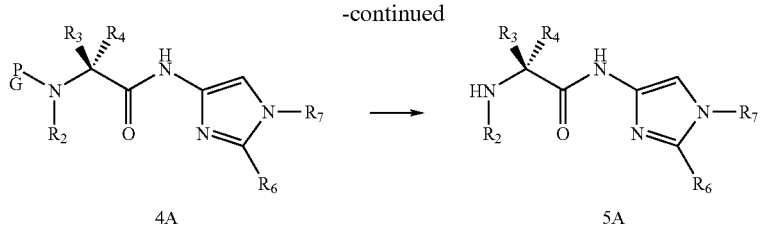

4A → 5A

Scheme 2 illustrates additional methods for the synthesis of imidazole compounds defined as Formula 2A. Treatment of nitroimidazole 6A with a base such as sodium hydride, potassium hydride, alkyl lithium, alkoxides, in a solvent such as tetrahydrofuran, dimethylformamide, methylene chloride, ether, preferably dimethylformamide, from about −60° C. to 40° C., where from −10° C. to 20° C. is preferred, followed by addition of R7-X wherein X is defined as Cl, Br, I, F, alkylsulfonate, or arylsulfonate followed by warming the reaction from 23° C. to 150° C. where 30-80° C. is preferrable, affords imidazoles of formula 2A. Reduction of the nitro compound and coupling reaction is carried out in a similar manner described above and is useful for preparing compounds of the Formula I.

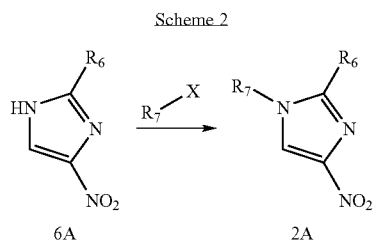

Scheme 2

6A → 2A

Scheme 3 illustrates additional methods for the synthesis of nitro-imidazole compounds defined as Formula 2A. A key starting material for the synthesis is the double-bond compound (a compound of Formula 16 or 17) substituted with the group ER8 and one to three groups selected from $R^8$, where ER8 is defined as an electron-withdrawing group chosen from $C(=O)R^9$, $C(=O)OR^9$, $C9=O)NR^9R^{10}$, $S(=O)_2R^9$, $S(=O)_2 NR^9R^{10}$, $S(=O)_2OR^9$, cyano, and heteroaryl. Additionally, compounds of formula 16 or 17 may be defined wherein ER8 is connected to one of the groups $R^8$ or directly to the carbon-carbon double bond to form a ring and thus includes compounds such as 2-cyclopentene-1-one and 2-cyclohexene-1-one. Alternatively, compounds of formula 17 where L is defined as Cl, Br, I, $OC(=O)R^9$, or $OS(=O)_2R^9$ may be used as starting materials; examples of such compounds are 3-chloro-1-cyclopentanone, 3-acetoxy-1-cyclobutanone. Thus, referring to Scheme 3, treatment of −=4-nitroimidazole 6A, with a base such as sodium hydride, potassium hydride, cesium carbonate, 1,8-diazabicyclo[5.4.0]undec-7-ene (DBU) or tetraalkylammonium chloride, where DBU is the preferred base, with intermediates 16 or 17 in a solvent such as acetonitrile, methylene chloride, 1,2-dichloroethane, or chloroform, where acetonitrile is the preferred solvent, at a temperature from about −60° C. to about 50° C., where −20° C. to 23° C. is the preferred range, affords addition products of formula 2A. Reduction of the nitro compound and coupling to give compounds of formula I is carried out in a similar manner described above.

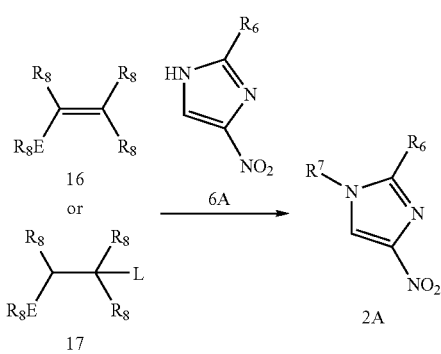

Scheme 3

16 or 17 → 6A → 2A

Scheme 4 below illustrates additional methods for the synthesis of amino-imidazole compounds defined as Formula 2A. Treatment of ethyl-2-isocyano-3-N,N-dimethylamino acrylate or benzyl-2-isocyano-3-N,N-dimethylamino acrylate with a primary amine, R7-NH2, in a solvent such as n-butanol, n-propanol, l-propanol, or ethanol, or in the absence of solvent, where n-propanol or no solvent are preferred, from about 23° C. to about 200° C., where from about 60° C. to 150° C. is preferred, affords imidazoles of formula 18. Treatment of ester 18 with a base such as potassium hydroxide, lithium hydroxide, or sodium hydroxide in a—solvent such as tetrahydrofuran, water, methanol, ethanol, propanol, wherein methanol is preferred provides the acid 19. The acid is converted to the acylazide 20 using methods known to one skilled in the art such as treatment of acid 19 with thionyl chloride or oxalyl chloride from −20 to 50° C. followed by removal of the residual solvent and quenching with sodium or potassium azide in a solvent such as toluene, tetrahydrofuran, methylene chloride, dioxane. The azide 20 undergoes Curtius rearrangement to the Boc 21 by heating from 5° C.-200° C. in a solvent such as t-butanol, benzyl alcohol, and ethanol. If t-butanol is used, deprotection of the N-Boc protecting group can be accomplished with HCl or trifluoroacetic acid in a solvent such as ether, tetrahydrofuran, where HCl in methanol is preferred affords the desired aminoimidazole compounds of formula 2A. If benzyl alcohol is used, deprotection can be accomplished by the use of a noble metal catalyst, in a solvent such as ethyl acetate, tetrahydrofuran, dioxane, or a mixture thereof, to an atmosphere of hydrogen gas at a pressure of about 1 to 100 atmospheres, where a preferred pressure of hydrogen gas is about one to about ten atmospheres. Palladium is the preferred noble metal catalyst which affords the desired aminoimidazole compounds of formula 2A. Alternatively, ester 18 can be treated with hydrazine in a solvent such as water from a temperature from 50° C. to 200° C. where 80° C. to 120° C. is preferred provides the hydrazide 22. The hydrazide 22 can be converted to the acylazide 20 using t-butylnitrite in a solvent or combination of solvent such as ether, methylene chloride, dichloroethane, chloroform, where in ether/methylene chloride is preferred at a temperature from −50° C. to 23° C. wherein −30° C. to 10° C. is preferred. The acylazide is then converted onto aminoimidazole compounds of formula 2A as described above. Made a change to scheme 4

Scheme 4

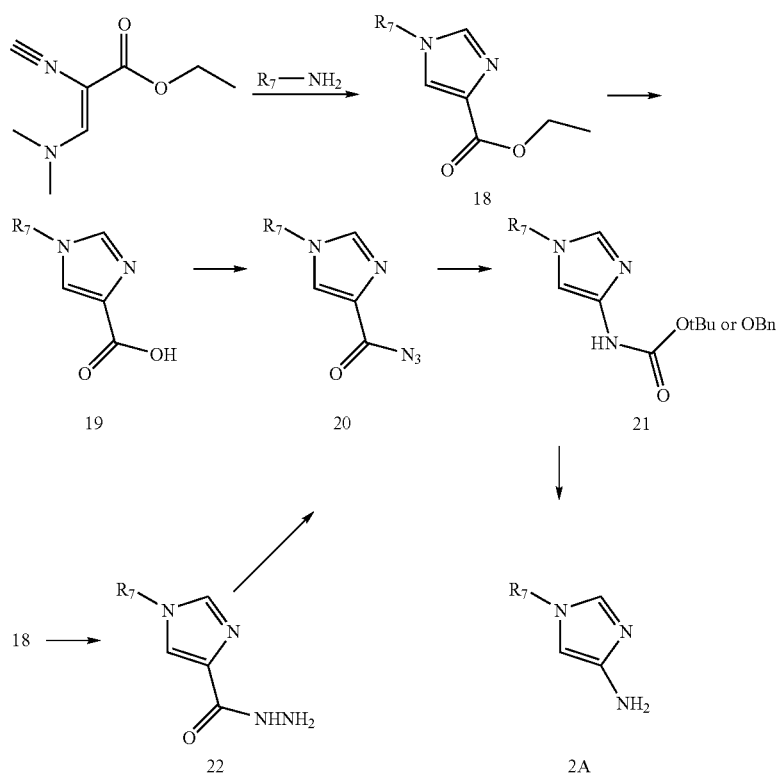

Scheme 5 below illustrates additional methods for the synthesis of amino-imidazole compounds defined as Formula I. Treatment of N—O-dimethyl hydroxylamine hydrochloride with trimethylaluminum in 1,2-dichloroethane followed by the addition of ester 18, prepared as described above and heating at about 30° C. to about 80° C., where a temperature of about 50° C. is preferred, affords imidazole 23. Addition of an organometallic reagent 24 wherein Z is defined as lithium halide, magnesium halide, potassium halide, where lithium halide is preferred, to a solution of amide 23 in a solvent such as tetrahydrofuran, methylene chloride, or diethyl ether, from a temperature about −78° C. to about 30° C., where a range of about −20° C. to about 0° C. is preferred affords 25. Addition of 25 to a mixture of hydroxylamine hydrochloride and potassium acetate in a lower alcoholic solvent, where in ethanol is preferred, at about 23° C., yields oxime 26 as a mixture of isomers. Treatment of an acetone solution of oxime 26 at about 0° C. with aqueous hydroxide followed by paratoluenesulfonyl chloride yields a mixture of O-sulfonyl compound following extractive workup. Dissolution of the crude material in a non-polar solvent such as benzene, hexanes, or toluene, wherein benzene is preferred, and application to a column of alumina followed by elution with chloroform-methanol (about 10:1) after approximately five minutes provides a compound of Formula I.

Scheme 5

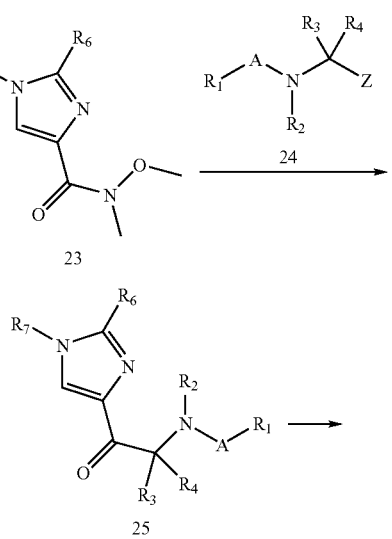

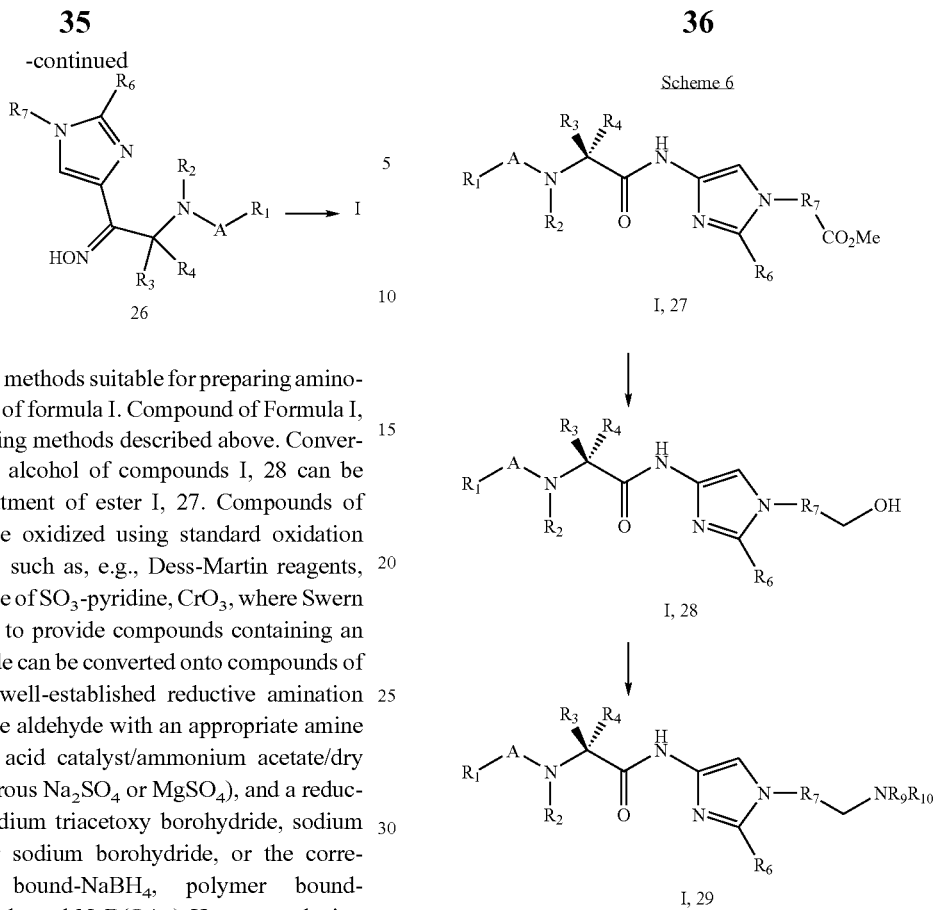

Scheme 6 illustrates methods suitable for preparing aminoimidazole compounds of formula I. Compound of Formula I, 27 can be prepared using methods described above. Conversion of ester I, 27 to alcohol of compounds I, 28 can be accomplished by treatment of ester I, 27. Compounds of formula I, 28 may be oxidized using standard oxidation method known in art, such as, e.g., Dess-Martin reagents, Swern oxidation, or use of $SO_3$-pyridine, $CrO_3$, where Swern oxidation is preferred to provide compounds containing an aldehyde. The aldehyde can be converted onto compounds of formula I, 29 using well-established reductive amination method by reacting the aldehyde with an appropriate amine 5A, with or without acid catalyst/ammonium acetate/dry agents (such as anhydrous $Na_2SO_4$ or $MgSO_4$), and a reducing agent, such as sodium triacetoxy borohydride, sodium cyanoborohydride, or sodium borohydride, or the corresponding polymer bound-$NaBH_4$, polymer bound-$NaBH_3CN$, or polymer bound-$NaB(OAc)_3H$, or any reducing agent (e.g., hydrogenation) that is known in the literature for reducing an imine bond to an amine, in an appropriate solvent, such as dichloroethane, chloroform, THF, MeOH, ethanol, isopropanol, t-butanol or toluene, at a temperature from about room temperature to about reflux, preferably from about room temperature to about 65° C. Alternatively, the alcohol of I, 28 can be converted to the corresponding alkyl or aryl sulfonate by treatment of the alcohol with alkyl or aryl sulfonyl chloride (where in mesyl chloride is preferred) in a solvent such as methylene chloride, tetrahydrofuran, toluene wherein methylene chloride in the presence of an amide such as triethylamine, diisopropyamine, pyridine, 2,6-lutidine, where in triethylamine is preferred at a temperature from −50° C. to 23° C. wherein −0° C. to 30° C. is preferred. The aryl or alkyl sulfonate is then reacted with an alkali metal azide (wherein sodium azide is preferred), in a polar solvent such as dimethylformamide, dimethylsulfoxide, alcohol, wherein ethanol is preferred produces a compound containing an azide. This intermediate azide may be reduced by exposing the azide to a noble metal catalyst, in a solvent such as ethyl acetate, tetrahydrofuran, dioxane, or a mixture thereof, to an atmosphere of hydrogen gas at a pressure of about 1 to 100 atmospheres, where a preferred pressure of hydrogen gas is about one to about ten atmospheres. Palladium is the preferred noble metal catalyst and the reaction affords the amine group. The amine group can then be converted to compounds of Formula 1, 29 using the reductive amination conditions described above.

Referring to Scheme 7, treatment of a solution of bromoimidazole 30 with a base, such as sodium hydride, potassium hydride, lithium hydride, cesium carbonate, sodium hydroxide, potassium hydroxide, cesium hydroxide, lithium diisopropyl amide, sodium amide, potassium hexamethyldisilazide, sodium hexamethyldisilazide, sodium tert-butoxide, or potassium tert-butoxide, in a reaction inert solvent such as tetrahydrofuran, 1,4-dioxane, N,N-dimethylformamide, dimethylsulfoxide, or toluene, from about −20° C. to 150° C., where 20° C. to 100° C. is preferred, in the absence or presence of a phase transfer catalyst, such as tetra-n-butylammonium chloride, tetra-n-butylammonium bromide, tetra-n-butylammonium iodide, benzyltrimethyl ammonium chloride, benzyltrimethyl ammonium bromide, or benzyltrimethyl ammonium fluoride, followed by the addition of an alkyl, allylic, or benzylic chloride, bromide, iodide, alkyl sulfonate, aryl sulfonate, or triflate, affords imidazoles 31.

Treatment of 1-substituted-4-bromoimidazole (31) with an intermediate of the formula 32 or PG-NH2 (where PG is defined as (C=O)alkyl or benzoyl) and a palladium catalyst such as palladium (II) acetate, allyl palladium chloride dimer, tris(dibenzylideneacetone)dipalladium (0), tris(dibenzylideneacetone)dipalladium (0) chloroform adduct, or palladium (II) chloride, where palladium (II) acetate, tris(dibenzylideneacetone)dipalladium (0), and tris(dibenzylideneacetone) dipalladium (0) chloroform adduct are preferred, and a phosphine ligand, preferably 9,9-dimethyl-4,5-bis (diphenylphosphino)xanthene (XANTPHOS) is preferred, and a base, such as cesium carbonate, or potassium phosphate ($K_3PO_4$), where potassium phosphate is preferred, in a reaction inert solvent, such as toluene, 1,4-dioxane, or tetrahydrofuran, from about 0° C. to 150° C., where 20° C. to 110° C. is preferred, affords the coupled product 1. Alternatively, treatment of 1-substituted-4-bromoimidazole (31) with an intermediate of the formula 32 or PG-NH2 (where PG is defined as (C=O)alkyl or benzoyl) and a diamine, such as 1,2-ethylenediamine, N,N'-dimethylethylenediamine, or cis-1,2-diaminocyclohexane, preferably N,N'-dimethylethylenediamine, and cuprous chloride, bromide or iodide, preferably cuprous iodide, in the presence of a small amount of water, preferably about 1% to about 4% water, in a reaction inert solvent such as 1,2-dimethoxyethane, diglyme, t-butyl methyl ether, tetrahydrofuran, benzene or toluene, preferably toluene, at a temperature of about 40° C. to about 150° C., preferably about 80° C. to about 120° C. to yield the compound of formula I or compounds of formula 33. In the case of compound 33, this can be converted to compounds of formula 2A using standard methods described above.

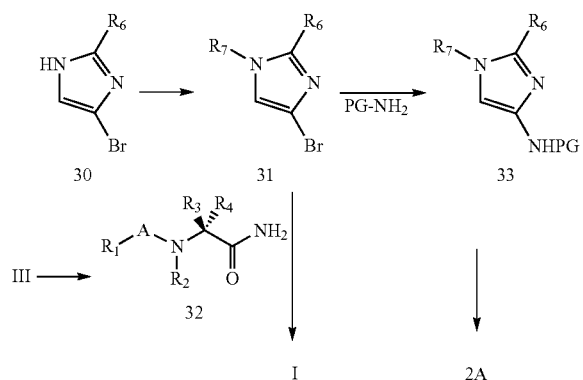

The starting materials used in the procedures of the above Schemes, the syntheses of which are not described above, are either commercially available, known in the art or readily obtainable from known compounds using methods that will be apparent to those skilled in the art.

The compounds of Formula I, and the intermediates shown in the above reaction schemes, may be isolated and purified by conventional procedures, such as recrystallization or chromatographic separation, such as on silica gel, either with an ethyl acetate/hexane elution gradient, a methylene chloride/methanol elution gradient, or a chloroform/methanol elution gradient. Alternatively, a reverse phase preparative HPLC or chiral HPLC separation technique may be used.

In each of the reactions discussed or illustrated above, pressure is not critical unless otherwise indicated. Pressures from about 0.5 atmospheres to about 5 atmospheres are generally acceptable, and ambient pressure, i.e., about 1 atmosphere, is preferred as a matter of convenience.

A compound of the Formula I of the present invention, or pharmaceutically acceptable salt thereof, may be administered to mammals via either the oral, parenteral (such as subcutaneous, intravenous, intramuscular, intrasternal and infusion techniques), rectal, intranasal, topical or transdermal (e.g., through the use of a patch) routes. In general, these compounds are most desirably administered in doses ranging from about 0.1 mg to about 1000 mg per day, in single or divided doses (i.e., from 1 to 4 doses per day), although variations will necessarily occur depending upon the species, weight, age and condition of the subject being treated, as well as the particular route of administration chosen. However, a dosage level that is in the range of about 0.1 mg/kg to about 5 gm/kg body weight per day, preferably from about 0.1 mg/kg to about 100 mg/kg body weight per day, is most desirably employed. Nevertheless, variations may occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such higher dosage levels are first divided into several small doses for administration throughout the day. Variations based on the aforementioned dosage range may be made by a physician of ordinary skill.

A compound of the Formula I of the present invention may be administered alone or in combination with pharmaceutically acceptable carriers or diluents by either of the routes previously indicated, and such administration may be carried out in single or multiple doses. Suitable pharmaceutical carriers include solid diluents or fillers, sterile aqueous media and various non-toxic organic solvents, etc. The pharmaceutical compositions formed by combining a compound of the Formula I, or a pharmaceutically acceptable salt thereof, with a pharmaceutically acceptable inert carrier, can then be readily administered in a variety of dosage forms such as tablets, capsules, lozenges, troches, hard candies, powders, sprays, creams, salves, suppositories, jellies, gels, pastes, lotions, ointments, aqueous suspensions, injectable solutions, elixirs, syrups, and the like. Moreover, oral pharmaceutical compositions may be suitably sweetened and/or flavored.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), methylcellulose, alginic acid and certain complex silicates, together with granulation binders such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in gelatin capsules. Preferred materials in this connection include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions containing a compound of the Formula I of the present invention or a pharmaceutically acceptable salt thereof in either sesame or peanut oil, in aqueous propylene glycol or in sterile aqueous solutions may be employed. The aqueous solutions should be suitably buffered (preferably pH greater than 8) if necessary and the liquid diluent first rendered isotonic with sufficient saline or glucose. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

The compounds of Formula I of the present invention are useful in inhibiting Aβ-peptide production (thus, gamma-secretase activity) in mammals, and therefore they are able to function as therapeutic agents in the treatment of the aforementioned disorders and diseases in an afflicted mammal.

A specific compound of the Formula I can be determined to inhibit Aβ-peptide production using biological assays known to those of ordinary skill in the art, for example the assays described below.

The activity of compounds of the Formula I of the present invention in inhibiting gamma-secretase activity was determined in a solubilized membrane preparation generally according to the description provided in McLendon et al. *Cell-free assays for γ-secretase activity, The FASEB Journal* (Vol. 14, December 2000, pp. 2383-2386). Using such assay, compounds of the present invention were determined to have an $IC_{50}$ activity for inhibiting gamma-secretase activity of less than about 100 micromolar. Preferred compounds of the invention are compounds that were determined to have an $IC_{50}$ activity for inhibiting gamma-secretase activity of less than about 1 micromolar.

The following Examples illustrate the present invention. It is to be understood, however, that the invention, as fully described herein and as recited in the claims, is not intended to be limited by the details of the following Examples.

EXAMPLES

General Procedure A

Coupling Method for Amide Formation a) EDC/HOBt/trialkylamine Coupling Procedure A mixture of a carboxylic acid (1.0 e.q.), amine (1.0 e.q.), HOBt (1.1-1.5 eq.), EDC (1.2-1.8 eq.) and a trialkylamine (triethylamine or diisopropylethylamine) (3-6 eq.) in an appropriate solvent or a mixture of solvents, for example methylene chloride, dichloroethane, THF, or DMF, was stirred at room temperature until product formation or disappearance of starting material. The solvent was removed under reduced pressure, the residue taken up in ethyl acetate (or similar selected solvent such as methylene chloride or chloroform) and water. The organic layer was separated, washed with dilute HCl (if the desired product contains a basic functional group, washing with dilute HCl may be omitted), brine, and dried over sodium sulfate. The solvent was then removed at reduced pressure to provide product.

b) HATU/Trialkylamine Coupling Procedure

A mixture of a carboxylic acid (1.0 e.q.), amine (1.0 e.q.), HATU (1.1-1.5 eq.) and a trialkylamine (triethylamine or diisopropylethylamine) (3-6 eq.) in an appropriate solvent or a mixture of solvents, for example methylene chloride, dichloroethane, THF, or DMF, was stirred at room temperature until product formation or disappearance of starting material. The solvent was removed under reduced pressure, the residue taken up in ethyl acetate (or similar selected solvent such as methylene chloride or chloroform) and water. The organic layer was separated, washed with dilute HCl (if the desired product contains a basic functional group, washing with dilute HCl may be omitted), brine, and dried over sodium sulfate. The solvent was then removed at reduced pressure to provide product.

c) PyBOP/Trialkylamine Coupling Procedure

A mixture of a carboxylic acid (1.0 e.q.), amine (1.0 e.q.), PyBOP (1.1-1.5 eq.) and a trialkylamine (triethylamine or diisopropylethylamine) (3-6 eq.) in an appropriate solvent or a mixture of solvents, for example methylene chloride, dichloroethane, THF, or DMF, was stirred at room temperature until product formation or disappearance of starting material. The solvent was removed under reduced pressure, the residue taken up in ethyl acetate (or similar selected solvent such as methylene chloride or chloroform) and water. The organic layer was separated, washed with dilute HCl (if the desired product contains a basic functional group, washing with dilute HCl may be omitted), brine, and dried over sodium sulfate. The solvent was removed at reduced pressure to provide product.

d) HBTU/Trialkylamine Coupling Procedure

A mixture of a carboxylic acid (1.0 e.q.), amine (1.0 e.q.), HBTU (1.1-1.5 eq.), and a trialkylamine (triethylamine or diisopropylethylamine) (3-6 eq.) in an appropriate solvent or a mixture of solvents, for example methylene chloride, dichloroethane, THF, or DMF, was stirred at room temperature until product formation or disappearance of starting material. The solvent was removed under reduced pressure, the residue taken up in ethyl acetate (or similar selected solvent such as methylene chloride or chloroform) and water. The organic layer was separated, washed with dilute HCl (if the desired product contains a basic functional group, washing with dilute HCl may be omitted), brine, and dried over sodium sulfate. The solvent was removed at reduced pressure to provide product.

e) Chloro-alkylformate Coupling Procedure

A mixture of a carboxylic acid (1 eq.) and triethylamine (eq.) was dissolved in an appropriate solvent, such as DMF and cooled to −23° C./iso-butyl formate (1 eq.) was added dropwise with stirring. After stirring for a period of time (form 15 min to 2 hr), a 2-amino-thiazole or an amine (1 eq.) was added and stirring continued for an additional 30 min at −23° C. The mixture was then warmed to room temperature until amide formation (typically overnight). The mixture was quenched with water and brine and extracted with an appropriate solvent such as ethyl acetate, methylene chloride or chloroform. The organic layer was washed with dilute $NaHSO_4$, $NaHCO_3$ and brine and the solvent was removed under reduced pressure to provide product. Purification may be necessary.

f) Trimethylaluminum Coupling Procedure

A mixture of an amine or an amino-thiazole (1-2 eq.), 2M trimethylaluminum was made in an appropriate solvent, such as THF, toluene, xylene, methylene chloride, or dichloroethane, or a mixture of solvents such as THF/toluene. The mixture was stirred at room temperature for 15 min to 2 hr, then an ester (1 eq.) was added. The resulting mixture was stirred at temperature between room temperature to reflux until product formation. The mixture was carefully quenched with Rochelle salt and extracted with an appropriate solvent such as ethyl acetate or methylene chloride, filtered through celite. The organic layer was washed with dilute HCl, neutralized with saturated sodium bicarbonate, and washed with brine. The organic layer was separated, dried and concentrated to give the desired amide. Purification may be necessary.

General Procedure B

Method for Reductive Amination a) Sodium Triacetoxyborohydride

An amine (1-4 eq.) in dichloroethane or THF was added to a solution of a ketone (1 eq.), $NaBH(Oac)_3$ (1-3 eq.) and acetic acid (1-3 eq.) in dichloroethane or THF. The mixture was stirred at room temperature until product formation or disappearance of starting material. The mixture was quenched with diluted base, extracted with methylene chloride or other appropriate solvent such as chloroform or ethyl acetate. The organic layer was separated, dried and concentrated to give the desired amide. Purification may be necessary.

b) Sodium Cyanoborohydride

A mixture of a ketone or aldehyde (1 eq.), an amine (1-20 eq.), sodium cyanoborohydride (1-5 eq.), acetic acid (1-3 eq.), sodium acetate (1-3 eq.), anhydrous sodium sulfate in dichloroethane or THF was stirred at room temperature to 60°

C., preferably heated at 35-50° C. until product formation. The mixture was quenched with diluted base, extracted with methylene chloride or other appropriate solvent such as chloroform or ethyl acetate. The organic layer was separated, dried and concentrated to give the desired amide. Purification may be necessary.

c) Potassium Formate and Palladium Acetate

A solution of an aldehyde or a ketone (1 eq.) and an amine (1 eq.) in dry DMF was stirred at room temperature for 4 hr, in the presence of molecular sieves. To the resulting reaction mixture were added potassium formate (2 eq.) and palladium acetate (catalytic amount, 0.02 eq.). The mixture was heated at 40-60° C. to complete reaction (TLC) and after cooling it was diluted with ice-water. The mixture was extracted with an appropriate solvent (such as methylene chloride, ethyl acetate, or chloroform). The organic layer was separated, dried and concentrated to give the desired amide. Purification may be necessary.

General Procedure C

Sodium Borohydride Reduction of Ketone or Aldehyde

A mixture of an aldehyde or a ketone (1 eq.) and sodium borohydride (1-10 eq.) in an appropriate solvent (methanol or ethanol) was stirred at 0° C. to room temperature for 10 minutes to complete reaction (TLC). The mixture was concentrated to a small volume, quenched with water, extracted with an appropriate solvent (such as methylene chloride, ethyl acetate, or chloroform). The organic layer was separated, dried and concentrated to give the desired amide. Purification may be necessary.

General Procedure D

N-tBOC Deprotecting Procedure

To a solution of N-tBOC compound in 1,4-dioxane (0.03-0.09 M) was added 4 N HCl in 1,4-dioxane or anhydrous HCl gas under nitrogen. The reaction mixture was stirred at room temperature for 1-24 hrs until all the starting material consumed (TLC). The solution was concentrated and pumped in vacuo. The final HCl salt of the corresponding amine was typically used without further purification.

General Procedure E

Conjugate Addition to Nitroimidazole

To a suspension of 4-nitroimidazole (2.0 equiv.) in acetonitrile is added DBU (1.0 equiv) followed by enone (1.0 equiv.). The reaction is heated for 12-24 hrs and the solvent removed in vacuo. The resultant solids are removed by filtration with methylene chloride and the resultant oil concentrated and purified by silica gel chromatography to provide the desired nitroimidazole.

General Procedure F

Alkylation of Nitroimidazole

To a suspension of 4-nitroimidazole (1.0 equiv.) in dimethylformamide at rt under a nitrogen atmosphere is added sodium hydride (1.2 equiv.) portionwise. The reaction is stirred for 15-30 min. And then the appropriate alkylhalide or alkyl mesylate is added. The mixture is stirred for 12-24 h at 50° C., cooled to 0° C., and quenched with water. The aqueous layer is extrated with methylene chloride, dried, and purified by silica gel chromatography to provide the desired nitroimidazole.

General Procedure G

Reduction of Nitroimidazole

To a solution of the nitroimidazole (1.0 equiv.) in ethylacetate is added palladium on carbon (0.25 w/w %). The reaction is hydrogenated @ 40-60 psi for 2-6 hrs and filtered over a pad of celite using ethyl acetate. The majority of the ethylacetate is removed in vacuo and the solution of the amine in the remaining ethylacetate is used without further purification.

General Procedure H

Reduction of Nitroimidazole-Ester Followed by Reductive Amination

To a solution of 3-Methyl-3-(4-nitro-imidazol-1-yl)-butyric acid methyl ester (1.0 equiv.) in methylene chloride at −78° C. is added DIBAL (2 equiv.) dropwise. The reaction is stirred for 1 h, quenched with ethylacetate, removed from cooling bath, and stirred for 10 min. To the reaction is added water and allowed to warm to rt and stir for 1 h. The reaction is diluted with methylene chloride, $Na_2SO_4$ is added and the reaction filtered through celite. The solvent is removed to afford 2-Methyl-2-(4-nitro-imidazol-1-yl)-propionaldehyde which is used in the next step without further purification.

To a solution of 2-Methyl-2-(4-nitro-imidazol-1-yl)-propionaldehyde (1 equiv.) in methylene chloride is added an appropriate amine (2 equiv.) and 4A molecular sieves. The reaction is stirred for 4-6 hours and an appropriate hydride reducing agent such as sodium triacetoxyborohydride (2 equiv.) is added. The reaction is stirred for 6-24 h, quenched with sodium bicarbonate, and the aqueous layer extracted with methylene chloride. The solvent is removed and residue purified by silica gel chromatography to provide the desired nitroimidazole.

The following compounds were prepared by methods analogous to those described above for General Procedure E:

3-(4-Nitro-imidazol-1-yl)-butyric acid methyl ester 4-nitroimidazole was reacted with methyl-3-methylacrylate to provide the title compound: 1H NMR (400 MHz, CDCl3) 1.62 (d, 3H, J=7.0 Hz), 2.81 (d, 2H, J=7.0 Hz), 3.66 (s, 3H), 4.78 (m, 1H), 7.53 (d, 1H, J=1.6 Hz), 7.82 (d, 1H, J=1.6 Hz); MS m/z 214.1 (M+1).

3-Methyl-3-(4-nitro-imidazol-1-yl)-butyric acid methyl ester 4-nitroimidazole was reacted with methyl-3,3-dimethylacrylate to provide the title compound: 1H NMR (400 MHz, CDCl3) 1.74 (s, 6H), 2.81 (s, 2H), 3.57 (s, 3H), 7.57 (d, 1H, J=1.3 Hz), 7.90 (d, 1H, J=1.6 Hz); MS m/z 228.2 (M+1).

The following compounds were prepared by methods analogous to that described above for General Procedure F:

2-Methyl-2-(4-nitro-imidazol-1-yl)-propionic acid methyl ester 4-nitroimidazole was alkylated with 2-Bromo-2-methylpropionic acid methyl ester to provide the title compound: 1H NMR (400 MHz, CDCl3) 1.89 (s, 6H), 3.78 (s, 3H), 7.59 (d, 1H, J=1.7 Hz), 7.89 (s, 1H, J=1.7 Hz); MS 214.1 m/z (M+1).

1-(1-Ethyl-propyl)-4-nitro-1H-imidazole 4-nitroimidazole was alkylated with 3-bromopentane to provide the title compound: 1H NMR (400 MHz, CDCl3) 0.84-0.90 (m, 6H), 1.71-1.82 (m, 2H), 1.86-1.96 (m, 2H), 3.79 (p, 1H, J=4.8 Hz), 7.41 (d, 1H, J=1.6 Hz), 7.73 (d, 1H, J=1.3 Hz); MS 184.2 m/z (M+1)

4-(4-Nitro-imidazol-1-yl)-Piperidine-1-carboxylic acid tert-butyl ester 4-nitroimidazole was alkylated with 4-methanesulfonyloxy-piperidine-1-carboxylic acid tert-butyl ester to provide the title compound: C13 NMR (100 MHz, CDCl₃) 28.5, 33.2, 42.7, 56.8, 80.7, 117.5, 134.4, 154.5; MS 297.1 m/z (M+1).

(4-Nitro-imidazol-1-yl)-acetic acid methyl ester 4-nitroimidazole was alkylated with bromo-acetic acid methyl ester to provide the title compound: 1H NMR (400 MHz) 3.82 (s, 1H), 4.80, (s, 2H), 7.47 (d, 1H, J=1.7 Hz), 7.84 (d, 1H, J=1.7 Hz); gc/ms m/z 185 (M).

2-Methyl-2-(2-methyl-4-nitro-imidazol-1-yl)-propionic acid methyl ester 2-methyl-4-nitro-imidazole was alkylated with bromo-acetic acid methyl ester to provide the title compound: MS m/z 228.2 (M+1).

1-(2-Methoxy-1,1-dimethyl-ethyl)-4-nitro-1H-imidazole

2-Methyl-2-(4-nitro-imidazol-1-yl)-propionic acid methyl ester was reduced using sodium borohydride in methanol and the resultant alcohol was alkylated with methyl iodide using sodium hydride as base to provide the title compound: H1 NMR (400 MHz, CDCl3) 1.53 (s, 6H), 3.25 (s, 3H), 3.38 (s, 2H), 7.53 (s, 1H), 7.88 (s, 1H).

4-(4-Nitro-imidazol-1-yl)-benzoic acid methyl ester 4-nitroimidazole (1 equiv) was combined with 4-iodo-methylbenzoate (1.2 equiv), cesium carbonate (1.0 equiv), copper (I) triflate (0.05 equiv), in DMF and heated overnight at 100° C. The solid was filtered and washed with methylene chloride, the resultant solvent was concentrated, and residue purified by silica gel chromatography to provide the title compound: MS m/z 248.2 (M+1).

(2,2-Dimethyl-propyl)-methyl-[2-methyl-2-(4-nitro-imidazol-1-yl)-propyl]-amine (2,2-Dimethyl-propyl)-[2-methyl-2-(4-nitro-imidazol-1-yl)-propyl]-amine was treated with formalin and formic acid at 85° C. for 5 h, quenched with aqueous sodium bicarbonate, extracted with methylene chloride, dried, concentrated, and the resultant residue purified by chromatography to afford the title compound: H1 NMR (400 MHz, CDCl₃) 0.74 (s, 9H), 1.52 (s, 6H), 2.2 (s, 2H), 2.8 (s, 2H), 7.6 (s, 1H), 7.9 (s, 1H); MS m/z 255.3 (M+1).

The following compounds were prepared by methods analogous to that described above for General Procedure H:

4-[2-Methyl-2-(4-nitro-imidazol-1-yl)-propyl]-morpholine

2-Methyl-2-(4-nitro-imidazol-1-yl)-propionaldehyde was reacted with morpholine to provide the title compound: MS m/z 255.1 (M+1)

1-(1,1-Dimethyl-2-pyrrolidin-1-yl-ethyl)-4-nitro-1H-imidazole

2-Methyl-2-(4-nitro-imidazol-1-yl)-propionaldehyde was reacted with pyrrolidine to provide the title compound: H1 NMR (400 MHz, CDCl3) 1.56 (s, 6H), 1.61 (m, 4H), 2.35 (m, 4H), 2.70 (m, 4H), 7.60 (s, 1H), 7.92 (s, 1H); MS m/z 239.2 (M+1).

(2,2-Dimethyl-propyl)-[2-methyl-2-(4-nitro-imidazol-1-yl)-propyl]-amine

2-Methyl-2-(4-nitro-imidazol-1-yl)-propionaldehyde was reacted with 2,2-dimethyl-propyl amine to provide the title compound: H1 NMR (400 MHz, CDCl3) 0.74 (s, 9H), 1.52 (s, 6H), 2.2 (s, 2H), 2.8 (s, 2H), 7.6 (s, 1H), 7.9 (s, 1H); MS m/z 255.3 (M+1).

[2-Methyl-2-(4-nitro-imidazol-1-yl)-propyl]-(2,2,2-trifluoro-ethyl)-amine

2-Methyl-2-(4-nitro-imidazol-1-yl)-propionaldehyde was reacted with 2,2,2-trifluoro-ethyl amine to provide the title compound: H1 NMR (400 MHz, CDCl3) 1.59 (s, 6H), 2.98 (s, 2H), 3.10 (m, 2H), 7.56 (s, 1H), 7.90 (s, 1H) MS m/z 267.3 (M+1).

1-[2-Methyl-2-(4-nitro-imidazol-1-yl)-propyl]-piperidine

2-Methyl-2-(4-nitro-imidazol-1-yl)-propionaldehyde was reacted with piperidine to provide the title compound: C13 NMR (100 MHz, CDCl3) 23.8, 25.6, 26.6, 57.0, 60.9, 69.2, 118.3, 134.4; MS m/z 253.3 (M+1).

2,6-Dimethyl-4-[2-methyl-2-(4-nitro-imidazol-1-yl)-propyl]-morpholine

2-Methyl-2-(4-nitro-imidazol-1-yl)-propionaldehyde was reacted with cis-2,6-dimethyl morpholine to provide the title compound: C13 NMR (100 MHz, CDCl3) 19.0, 25.7, 60.8, 61.5, 68.5, 72.0, 118.0, 134.5; MS m/z 283.2 (M+1).

Dimethyl-[2-methyl-2-(4-nitro-imidazol-1-yl)-propyl]-amine

2-Methyl-2-(4-nitro-imidazol-1-yl)-propionaldehyde was reacted with dimethyl amine to provide the title compound: H1 NMR (400 MHz, CDCl3) 1.50 (s, 6H), 2.00 (s, 6H), 2.40 (s, 2H), 7.55 (s, 1H), 7.89 (s, 1H).

1-Methyl-4-[2-methyl-2-(4-nitro-imidazol-1-yl)-propyl]-piperazine

2-Methyl-2-(4-nitro-imidazol-1-yl)-propionaldehyde was reacted with N-methyl piperazine to provide the title compound: MS m/z 268.2 (M+1).

The following compounds were prepared by methods analogous to that described above for General Procedure G:

2-(4-Amino-imidazol-1-yl)-2-methyl-propionic acid methyl ester

2-Methyl-2-(4-nitro-imidazol-1-yl)-propionic acid methyl ester was hydrogenated to provide the title compound: MS m/z 184.1 (M+1)

1-(1-Ethyl-propyl)-1H-imidazol-4-ylamine 1-(1-Ethyl-propyl)-4-nitro-1H-imidazole was hydrogenated to provide the title compound: MS m/z 154.1 (M+1)

3-(4-Amino-imidazol-1-yl)-butyric acid methyl ester 3-(4-Nitro-imidazol-1-yl)-butyric acid methyl ester was hydrogenated to provide the title compound: MS m/z 184.2 (M+1)

3-(4-Amino-imidazol-1-yl)-3-methyl-butyric acid methyl ester

3-Methyl-3-(4-nitro-imidazol-1-yl)-butyric acid methyl ester was hydrogenated to provide the title compound: MS m/z 198.1 (M+1)

4-(4-Amino-imidazol-1-yl)-piperidine-1-carboxylic acid tert-butyl ester 4-(4-Nitro-imidazol-1-yl)-piperidine-1-carboxylic acid tert-butyl ester was hydrogenated to provide the title compound.

1-(1,1-Dimethyl-2-morpholin-4-yl-ethyl)-1H-imidazol-4-ylamine

4-[2-Methyl-2-(4-nitro-imidazol-1-yl)-propyl]-morpholine was hydrogenated to provide the title compound; MS m/z 225.3 (M+1).

1-(1,1-Dimethyl-2-pyrrolidin-1-yl-ethyl)-1H-imidazol-4-ylamine 1-(1,1-Dimethyl-2-pyrrolidin-1-yl-ethyl)-4-nitro-1H-imidazole was hydrogenated to provide the title compound; MS m/z 209.1 (M+1).

1-[2-(2,2-Dimethyl-propylamino)-1,1-dimethyl-ethyl]-1H-imidazol-4-ylamine (2,2-Dimethyl-propyl)-[2-methyl-2-(4-nitro-imidazol-1-yl)-propyl]-amine was hydrogenated to provide the title compound; MS m/z 253.3 (M+1).

1-[1,1-Dimethyl-2-(2,2,2-trifluoro-ethylamino)-ethyl]-1H-imidazol-4-ylamine

[2-Methyl-2-(4-nitro-imidazol-1-yl)-propyl]-(2,2,2-trifluoro-ethyl)-amine was hydrogenated to provide the title compound; MS m/z 237.2 (M+1).

1-(1,1-Dimethyl-2-piperidin-1-yl-ethyl)-1H-imidazol-4-ylamine

1-[2-Methyl-2-(4-nitro-imidazol-1-yl)-propyl]-piperidine amine was hydrogenated to provide the title compound; MS m/z 223.2 (M+1).

1-[2-(2,6-Dimethyl-morpholin-4-yl)-1,1-dimethyl-ethyl]-1H-imidazol-4-ylamine 2,6-Dimethyl-4-[2-methyl-2-(4-nitro-imidazol-1-yl)-propyl]-morpholine was hydrogenated to provide the title compound; MS m/z 253.2 (M+1).

1-(2-Dimethylamino-1,1-dimethyl-ethyl)-1H-imidazol-4-ylamine

Dimethyl-[2-methyl-2-(4-nitro-imidazol-1-yl)-propyl]-amine was hydrogenated to provide the title compound; MS m/z 183.3 (M+1).

(4-Amino-imidazol-1-yl)-acetic acid methyl ester (4-Nitro-imidazol-1-yl)-acetic acid methyl ester was hydrogenated to provide the title compound: Gc/MS m/z=185 (RT=3.49 min.).

2-(4-Amino-2-methyl-imidazol-1-yl)-2-methyl-propionic acid methyl ester

2-Methyl-2-(2-methyl-4-nitro-imidazol-1-yl)-propionic acid methyl ester was hydrogenated to provide the title compound.

1-(2-Methoxy-1,1-dimethyl-ethyl)-1H-imidazol-4-ylamine 1-(2-Methoxy-1,1-dimethyl-ethyl)-4-nitro-1H-imidazole was hydrogenated to provide the title compound: MS m/z 170.2 (M+1).

4-(4-Amino-imidazol-1-yl)-benzoic acid methyl ester 4-(4-Nitro-imidazol-1-yl)-benzoic acid methyl ester was hydrogenated to provide the title compound: MS m/z 218.2 (M+1).

1-[2-[(2,2-Dimethyl-propyl)-methyl-amino]-1,1-dimethyl-ethyl]-1H-imidazol-4-ylamine (2,2-Dimethyl-propyl)-methyl-[2-methyl-2-(4-nitro-imidazol-1-yl)-propyl]-amine was hydrogenated to provide the title compound: MS m/z 239.2 (M+1).

1-[1,1-Dimethyl-2-(4-methyl-piperazin-1-yl)-ethyl]-1H-imidazol-4-ylamine

1-Methyl-4-[2-methyl-2-(4-nitro-imidazol-1-yl)-propyl]-piperazine was hydrogenated to provide the title compound.

The following compounds were prepared by methods analogous to those described above for General Procedure A, general coupling procedure (e):

2-[4-(2-tert-Butoxycarbonylamino-pentanoylamino)-imidazol-1-yl]-2-methyl-propionic acid methyl ester 2-(4-Amino-imidazol-1-yl)-2-methyl-propionic acid methyl ester was coupled with (L)-N-Boc norvaline to provide the title compound: MS m/z 353.3 (M+1).

{1-[1-(1-Ethyl-propyl)-1H-imidazol-4-ylcarbamoyl]-butyl}-carbamic acid tert-butyl ester 1-(1-Ethyl-propyl)-1H-imidazol-4-ylamine was coupled with (L)-N-Boc norvaline to provide the title compound: MS m/z 383.1 (M+1).

3-[4-(2-tert-Butoxycarbonylamino-pentanoylamino)-imidazol-1-yl]-butyric acid methyl ester 3-(4-Amino-imidazol-1-yl)-butyric acid methyl ester was coupled with (L)-N-Boc norvaline to provide the title compound: MS m/z 383.3 (M+1).

3-[4-(2-tert-Butoxycarbonylamino-pentanoylamino)-imidazol-1-yl]-3-methyl-butyric acid methyl ester 3-(4-Amino-imidazol-1-yl)-3-methyl-butyric acid methyl ester was coupled with (L)-N-Boc norvaline to provide the title compound: C13 NMR (100 MHz, CDCl3) 13.9, 19.0, 28.1, 28.5, 36.1, 47.2, 51.9, 54.4, 56.3, 79.7, 104.8, 131.3, 138.0, 155.6, 169.8, 170.0; MS m/z 397.3 (M+1)

3-[4-(2-tert-Butoxycarbonylamino-propionylamino)-imidazol-1-yl]-3-methyl-butyric acid methyl ester 4-(4-Amino-imidazol-1-yl)-piperidine-1-carboxylic acid tert-butyl ester was coupled with (L)-N-Boc alanine to provide the title compound: C13 NMR (100 MHz, CDCl3) 19.9, 28.1, 28.2, 28.5, 47.1, 50.1, 51.9, 56.3, 79.7, 104.8, 131.1, 138.1, 155.4, 170.0, 170.2; MS m/z 369.1 (M+1)

2-[4-(2-tert-Butoxycarbonylamino-4-methyl-pentanoylamino)-imidazol-1-yl]-2-methyl-propionic acid methyl ester 2-(4-Amino-imidazol-1-yl)-2-methyl-propionic acid methyl ester was coupled with (L)-N-Boc isoleucine to provide the title compound:

2-[4-(2-tert-Butoxycarbonylamino-propionylamino)-imidazol-1-yl]-2-methyl-propionic acid methyl ester 2-(4-Amino-imidazol-1-yl)-2-methyl-propionic acid methyl ester was coupled with (L)-N-Boc alanine to provide the title compound.

{1-[1-(2-Methoxy-1,1-dimethyl-ethyl)-1H-imidazol-4-ylcarbamoyl]-butyl}-carbamic acid tert-butyl ester 1-(2-Methoxy-1,1-dimethyl-ethyl)-1H-imidazol-4-ylamine was coupled with (L)-N-Boc alanine to provide the title compound: MS m/z 369.3 (M+1).

General Procedure I

Ester Reduction

{1-[1-(2-Hydroxy-1,1-dimethyl-ethyl)-1H-imidazol-4-ylcarbamoyl]-butyl}-carbamic acid tert-butyl ester To a solution of 2-[4-(2-tert-Butoxycarbonylamino-pentanoylamino)-imidazol-1-yl]-2-methyl-propionic acid methyl ester (9.6 g, 25.2 mmol) in 100 mL of diethyl ether at 0° C. is added 1.0 M lithium aluminum hydride (37.9 mL, 37.9 mmol) in diethylether dropwise over 1 h. The reaction is stirred at 0° C. for 15 min and warmed to rt for 1 h. The reaction is slowly quenched with 200 mL of water and ethyl acetate (200 mL). The reaction is filtered and the aqueous is extracted with ethylacetate, dried, and concentrated. The resultant residue is purified by silica gel chromatography to provide the title compound (5.8 g); MS m/z 355.3 (M+1).

The following compounds were prepared by methods analogous to those described above for General Procedure I:

{1-[1-(3-Hydroxy-1,1-dimethyl-propyl)-1H-imidazol-4-ylcarbamoyl]-butyl}-carbamic acid tert-butyl ester 3-[4-(2-tert-Butoxycarbonylamino-pentanoylamino)-imidazol-1-yl]-3-methyl-butyric acid methyl ester was reduced to provide the title compound: C13 NMR (100 MHz, CDCl3) 14.0, 18.9, 28.6, 28.9, 29.2, 36.5, 44.9, 54.1, 57.4, 58.3, 79.9, 105.0, 131.4, 138.0, 155.7, 169.6; MS m/z 369.2 (M+1).

2-[2-(3,5-Difluoro-phenyl)-acetylamino]-pentanoic acid [1-(1,1-dimethyl-2-oxo-ethyl)-1H-imidazol-4-yl]-amide 2-[2-(3,5-Difluoro-phenyl)-acetylamino]-pentanoic acid [1-(2-hydroxy-1,1-dimethyl-ethyl)-1H-imidazol-4-yl]-amide was reduced to provide the title compound: MS m/z 353.3 (M+1).

{1-[1-(2-Hydroxy-1,1-dimethyl-ethyl)-1H-imidazol-4-ylcarbamoyl]-3-methyl-butyl}-carbamic acid tert-butyl ester 2-[4-(2-tert-Butoxycarbonylamino-4-methyl-pentanoylamino)-imidazol-1-yl]-2-methyl-propionic acid methyl ester was reduced to provide the title compound.

{1-[1-(2-Hydroxy-1,1-dimethyl-ethyl)-1H-imidazol-4-ylcarbamoyl]-ethyl}-carbamic acid tert-butyl ester 2-[4-(2-tert-Butoxycarbonylamino-propionylamino)-imidazol-1-yl]-2-methyl-propionic acid methyl ester was reduced to provide the title compound.

General Procedure J

Swern Oxidation

{1-[1-(1,1-Dimethyl-2-oxo-ethyl)-1H-imidazol-4-ylcarbamoyl]-butyl}-carbamic acid tert-butyl ester To a solution of oxalyl chloride (1.2 mL, 14.1 mmol) in 110 mL of methylene chloride at −78° C. is added DMSO (2.2 mL, 30.6 mmol) dropwise. The reaction is stirred for 20 min. and {1-[1-(2-Hydroxy-1,1-dimethyl-ethyl)-1H-imidazol-4-ylcarbamoyl]-butyl}-carbamic acid tert-butyl ester (4.2 g, 11.8 mmol) is added in 10 mL of methylene chloride. The reaction is stirred for 1 h, triethylamine (8.2 mL, 58.9 mmol) is added, and the reaction warmed to 0° C. for 20 min. The reaction is quenched with 100 mL of sodium bicarbonate, extracted with methylene chloride, dried, and concentrated to afford the title compound (4.5 g): MS m/z 353.2 (M+1).

The following compounds were prepared by methods analogous to those described above for General Procedure J:

{1-[1-(1,1-Dimethyl-3-oxo-propyl)-1H-imidazol-4-ylcarbamoyl]-butyl}-carbamic acid tert-butyl ester Oxidation of {1-[1-(3-Hydroxy-1,1-dimethyl-propyl)-1H-imidazol-4-ylcarbamoyl]-butyl}-carbamic acid tert-butyl ester afforded the title compound: C13 NMR (100 MHz, CDCl3) 13.9, 19.0, 28.5, 28.6, 35.9, 54.5, 55.0, 56.1, 79.8, 104.6, 126.1, 131.1, 131.2, 135.4, 155.6, 170.0, 199.0; MS m/z 367.2 (M+1).

{1-[1-(1,1-Dimethyl-2-oxo-ethyl)-1H-imidazol-4-ylcarbamoyl]-3-methyl-butyl}-carbamic acid tert-butyl ester Oxidation of {1-[1-(2-Hydroxy-1,1-dimethyl-ethyl)-1H-imidazol-4-ylcarbamoyl]-3-methyl-butyl}-carbamic acid tert-butyl ester afforded the title compound.

{1-[1-(1,1-Dimethyl-2-oxo-ethyl)-1H-imidazol-4-ylcarbamoyl]-ethyl}-carbamic acid tert-butyl ester Oxidation of {1-[1-(2-Hydroxy-1,1-dimethyl-ethyl)-1H-imidazol-4-ylcarbamoyl]-ethyl}-carbamic acid tert-butyl ester afforded the title compound.

2-[2-(3,5-Difluoro-phenyl)-acetylamino]-pentanoic acid [1-(1,1-dimethyl-3-oxo-propyl)-1H-imidazol-4-yl]-amide Oxidation of 2-[2-(3,5-Difluoro-phenyl)-acetylamino]-pentanoic acid [1-(3-hydroxy-1,1-dimethyl-propyl)-1H-imidazol-4-yl]-amide afforded the title compound.
2-(6,8-Difluoro-1,2,3,4-tetrahydro-naphthalen-2-ylamino)-pentanoic acid [1-(1,1-dimethyl-2-oxo-ethyl)-1H-imidazol-4-yl]-amide afforded the title compound: MS m/z 419.4 (M+1).
Oxidation of 2-{4-[2-(6,8-Difluoro-1,2,3,4-tetrahydro-naphthalen-2-ylamino)-pentanoylamino]-imidazol-1-yl}-2-methyl-propionic acid methyl ester.
The following compounds were prepared by methods analogous to those described above for General Procedure B:

{1-[1-(1,1-Dimethyl-2-pyrrolidin-1-yl-ethyl)-1H-imidazol-4-ylcarbamoyl]-butyl}-carbamic acid tert-butyl ester Reductive amination of {1-[1-(1,1-Dimethyl-2-oxo-ethyl)-1H-imidazol-4-ylcarbamoyl]-butyl}-carbamic acid tert-butyl ester with pyrrolidine afforded the title compound: MS m/z 408.3 (M+1).

{1-[1-(1,1-Dimethyl-2-morpholin-4-yl-ethyl)-1H-imidazol-4-ylcarbamoyl]-butyl}-carbamic acid tert-butyl ester Reductive amination of {1-[1-(1,1-Dimethyl-2-oxo-ethyl)-1H-imidazol-4-ylcarbamoyl]-butyl}-carbamic acid tert-butyl ester with morpholine afforded the title compound: MS m/z 424.3 (M+1).

{1-[1-(1,1-Dimethyl-3-pyrrolidin-1-yl-propyl)-1H-imidazol-4-ylcarbamoyl]-butyl}-carbamic acid tert-butyl ester Reductive amination of {1-[1-(1,1-Dimethyl-3-oxo-propyl)-1H-imidazol-4-ylcarbamoyl]-butyl}-carbamic acid tert-butyl ester with pyrrolidine afforded the title compound: C13 NMR (100 MHz, CDCl3) 13.9, 19.0, 28.5, 28.6, 35.9, 54.5, 55.0, 56.1, 79.8, 104.6, 126.1, 131.1, 131.2, 135.4, 155.6, 170.0, 199.0; MS m/z 367.2 (M+1).

{1-[1-(1,1-Dimethyl-3-morpholin-4-yl-propyl)-1H-imidazol-4-ylcarbamoyl]-butyl}-carbamic acid tert-butyl ester Reductive amination of {1-[1-(1,1-Dimethyl-3-oxo-propyl)-1H-imidazol-4-ylcarbamoyl]-butyl}-carbamic acid tert-butyl ester with morpholine afforded the title compound: C13 NMR (100 MHz, CDCl3) 14.0, 19.0, 28.3, 28.5, 28.7, 36.3, 39.7, 53.9, 54.3, 57.3, 67.1, 79.5, 105.0, 131.3, 138.0, 155.6, 169.8; MS m/z 438.2 (M+1).

{1-[1-(1,1-Dimethyl-2-pyrrolidin-1-yl-ethyl)-1H-imidazol-4-ylcarbamoyl]-ethyl}-carbamic acid tert-butyl ester Reductive amination of {1-[1-(1,1-Dimethyl-2-oxo-ethyl)-1H-imidazol-4-ylcarbamoyl]-ethyl}-carbamic acid tert-butyl ester with pyrrolidine afforded the title compound.

{1-[1-(1,1-Dimethyl-2-pyrrolidin-1-yl-ethyl)-1H-imidazol-4-ylcarbamoyl]-3-methyl-butyl}-carbamic acid tert-butyl ester Reductive amination of {1-[1-(1,1-Dimethyl-2-oxo-ethyl)-1H-imidazol-4-ylcarbamoyl]-3-methyl-butyl}-carbamic acid tert-butyl ester with pyrrolidine afforded the title compound.

{1-[7-(2,2-Dimethyl-propyl)-5,5-dimethyl-5,6,7,8-tetrahydro-imidazo[1,5-a]pyrazin-1-ylcarbamoyl]-butyl}-carbamic acid tert-butyl ester Reductive amination of {1-[1-(1,1-Dimethyl-2-oxo-ethyl)-1H-imidazol-4-ylcarbamoyl]-butyl}-carbamic acid tert-butyl ester with 2,2-dimethyl propyl amine afforded (1-{1-[2-(2,2-Dimethyl-propylamino)-1,1-dimethyl-ethyl]-1H-imidazol-4-ylcarbamoyl}-butyl)-carbamic acid tert-butyl ester: MS m/z 424.5 (M+1). Treatment of the above amine with formalin and formic acid at 85° C. followed by purification afforded the title compound:
The following compounds were prepared by methods analogous to those described above for General Procedure D:

2-[4-(2-Amino-pentanoylamino)-imidazol-1-yl]-2-methyl-propionic acid methyl ester 2-[4-(2-tert-Butoxycarbonylamino-pentanoylamino)-imidazol-1-yl]-2-methyl-propionic acid methyl ester was deprotected to afford the title compound: MS m/z 283.1 (M+1).

2-Amino-pentanoic acid [1-(1-ethyl-propyl)-1H-imidazol-4-yl]-amide

{1-[1-(1-Ethyl-propyl)-1H-imidazol-4-ylcarbamoyl]-butyl}-carbamic acid tert-butyl ester was deprotected to afford the title compound: MS m/z 253.1 (M+1).

3-[4-(2-Amino-pentanoylamino)-imidazol-1-yl]-butyric acid methyl ester

3-[4-(2-tert-Butoxycarbonylamino-pentanoylamino)-imidazol-1-yl]-butyric acid methyl ester was deprotected to afford the title compound: MS m/z 283.2 (M+1).

3-[4-(2-Amino-pentanoylamino)-imidazol-1-yl]-3-methyl-butyric acid methyl ester 3-[4-(2-tert-Butoxycarbonylamino-pentanoylamino)-imidazol-1-yl]-3-methyl-butyric acid methyl ester was deprotected to afford the title compound: MS m/z 297.2 (M+1).

3-[4-(2-Amino-propionylamino)-imidazol-1-yl]-3-methyl-butyric acid methyl ester 3-[4-(2-tert-Butoxycarbonylamino-propionylamino)-imidazol-1-yl]-3-methyl-butyric acid methyl ester was deprotected to afford the title compound: MS m/z 269.2 (M+1).

2-Amino-pentanoic acid [1-(1,1-dimethyl-2-pyrrolidin-1-yl-ethyl)-1H-imidazol-4-yl]-amide {1-[1-(1,1-Dimethyl-2-pyrrolidin-1-yl-ethyl)-1H-imidazol-4-ylcarbamoyl]-butyl}-carbamic acid tert-butyl ester was deprotected to afford the title compound: MS m/z 308.3 (M+1).

2-Amino-pentanoic acid [1-(1,1-dimethyl-2-morpholin-4-yl-ethyl)-1H-imidazol-4-yl]-amide {1-[1-(1,1-Dimethyl-2-morpholin-4-yl-ethyl)-1H-imidazol-4-ylcarbamoyl]-butyl}-carbamic acid tert-butyl ester was deprotected to afford the title compound: MS m/z 324.3 (M+1).

2-Amino-pentanoic acid [1-(1,1-dimethyl-3-pyrrolidin-1-yl-propyl)-1H-imidazol-4-yl]-amide {1-[1-(1,1-Dimethyl-3-pyrrolidin-1-yl-propyl)-1H-imidazol-4-ylcarbamoyl]-butyl}-carbamic acid tert-butyl ester was deprotected to afford the title compound: MS m/z 322.2 (M+1).

2-Amino-pentanoic acid [1-(1,1-dimethyl-3-morpholin-4-yl-propyl)-1H-imidazol-4-yl]-amide {1-[1-(1,1-Dimethyl-3-morpholin-4-yl-propyl)-1H-imidazol-4-ylcarbamoyl]-butyl}-carbamic acid tert-butyl ester was deprotected to afford the title compound: C13 NMR (100 MHz, CDCl3) 13.9, 19.0, 28.4, 28.5, 31.4, 36.8, 39.6, 53.9, 54.9, 57.4, 66.9, 104.9, 130.8, 137.6, 172.1; MS m/z 338.2 (M+1).

2-Amino-4-methyl-pentanoic acid [1-(1,1-dimethyl-2-pyrrolidin-1-yl-ethyl)-1H-imidazol-4-yl]-amide {1-[1-(1,1-Dimethyl-2-pyrrolidin-1-yl-ethyl)-1H-imidazol-4-ylcarbamoyl]-3-methyl-butyl}-carbamic acid tert-butyl ester was deprotected to afford the title compound.

2-Amino-N-[1-(1,1-dimethyl-2-pyrrolidin-1-yl-ethyl)-1H-imidazol-4-yl]-propionamide {1-[1-(1,1-Dimethyl-2-pyrrolidin-1-yl-ethyl)-1H-imidazol-4-ylcarbamoyl]-ethyl}-carbamic acid tert-butyl ester was deprotected to afford the title compound.

2-Amino-pentanoic acid [1-(2-methoxy-1,1-dimethyl-ethyl)-1H-imidazol-4-yl]-amide {1-[1-(2-Methoxy-1,1-dimethyl-ethyl)-1H-imidazol-4-ylcarbamoyl]-butyl}-carbamic acid tert-butyl ester was deprotected to afford the title compound: MS m/z 269.3 (M+1).

2-Amino-pentanoic acid [7-(2,2-dimethyl-propyl)-5,5-dimethyl-5,6,7,8-tetrahydro-imidazo[1,5-a]pyrazin-1-yl]-amide {1-[7-(2,2-Dimethyl-propyl)-5,5-dimethyl-5,6,7,8-tetrahydro-imidazo[1,5-a]pyrazin-1-ylcarbamoyl]-butyl}-carbamic acid tert-butyl ester was deprotected to provide the title compound: MS m/z 336.4 (M+1).

The following Examples were prepared by methods analogous to those described above for General Procedure A, coupling procedure (a):

Example 1

3-(4-{2-[2-(3,5-Difluoro-phenyl)-acetylamino]-pentanoylamino}-imidazol-1-yl)-butyric acid methyl ester 3-[4-(2-Amino-pentanoylamino)-imidazol-1-yl]-butyric acid methyl ester was coupled with (3,5-Difluoro-phenyl)-acetic acid to provide the title compound: Mixture of Diastereomers, MS m/z 437.2 (M+1). The diastereomers were separated using ChiralOD column, elute 85:15 heptane:ethanol; Flow Rate 85 mL/min. Diastereomer #1 (RT=9.39 min.) C13 NMR (100 MHz, CDCl3) 13.9, 18.9, 19.2, 21.5, 21.6, 28.3, 30.5, 35.9, 41.9, 42.2, 43.0, 50.6, 50.7, 52.1, 53.1, 102.7, 104.9, 112.3, 112.5, 132.2, 138.0, 169.2, 169.6, 170.7; MS m/z 437.2 (M+1) Diastereomer #2 (RT=13.6 min.) C13 NMR (100 MHz, CDCl3) 13.9, 18.9, 21.6, 35.8, 42.0, 43.1, 50.8, 52.1, 53.1, 102.9, 104.8, 112.3, 112.6, 132.4, 137.9, 169.3, 170.6; MS m/z 437.2 (M+1).

Example 2

3-{4-[2-(2-Hydroxy-3-methyl-butyrylamino)-pentanoylamino]-imidazol-1-yl}-3-methyl-butyric acid methyl ester 3-[4-(2-Amino-pentanoylamino)-imidazol-1-yl]-3-methyl-butyric acid methyl ester was coupled with (S)-2-hydroxy-3-methyl-butyric acid to provide the title compound: C13 NMR (100 MHz, CDCl3) 13.9, 16.0, 19.1, 19.4, 28.1, 32.2, 35.5, 47.1, 51.9, 52.7, 56.4, 105.1, 131.1, 137.6, 169.6, 170.0, 174.0.

Example 3

3-(4-{2-[2-(3,5-Difluoro-phenyl)-acetylamino]-pentanoylamino}-imidazol-1-yl)-3-methyl-butyric acid methyl ester 3-[4-(2-Amino-pentanoylamino)-imidazol-1-yl]-3-methyl-butyric acid methyl ester was coupled with (3,5-Difluoro-phenyl)-acetic acid to provide the title compound: C13 NMR (100 MHz, CDCl3) 13.9, 19.0, 27.9, 28.1, 35.9, 42.7, 46.8, 51.8, 53.1, 56.3, 102.2, 102.5, 102.7, 105.1, 112.2, 112.3, 112.4, 112.5, 131.3, 137.9, 139.2, 161.8, 164.2, 164.3, 169.4, 169.9, 170.0; MS 451.2 m/z (M+1).

Example 4

3-{4-[2-(2-Hydroxy-3,3-dimethyl-butyrylamino)-pentanoylamino]-imidazol-1-yl}-3-methyl-butyric acid methyl ester 3-[4-(2-Amino-pentanoylamino)-imidazol-1-yl]-3-methyl-butyric acid methyl ester was coupled with (S)-2-hydroxy-3,3-dimethyl-butyric acid to provide the title compound: C13 NMR (100 MHz, CDCl3) 13.9, 19.1, 26.3, 28.1, 35.2, 35.3, 47.1, 51.9, 52.7, 56.4, 79.9, 105.0, 131.0, 137.6, 169.3, 170.1, 173.1; MS m/z 411.1 (M+1).

Example 5

2-(2-Hydroxy-3,3-dimethyl-butyrylamino)-pentanoic acid [1-(1-ethyl-propyl)-1H-imidazol-4-yl]-amide 2-Amino-pentanoic acid [1-(1-ethyl-propyl)-1H-imidazol-4-yl]-amide was coupled with (S)-2-hydroxy-3,3-dimethyl-butyric acid to provide the title compound: C13 NMR (100 MHz, CDCl3) 10.8, 13.9, 19.0, 26.3, 28.8, 35.3, 35.6, 52.7, 62.9, 79.8, 104.8, 132.7, 137.9, 169.2, 172.9; MS 367.1 m/z (M+1).

Example 6

2-[2-(3,5-Difluoro-phenyl)-acetylamino]-pentanoic acid [1-(1-ethyl-propyl)-1H-imidazol-4-yl]-amide 2-Amino-pentanoic acid [1-(1-ethyl-propyl)-1H-imidazol-4-yl]-amide was coupled with (3,5-Difluoro-phenyl)-acetic acid to provide the title compound: C13 NMR (100 MHz, CDCl3) 10.7, 10.8, 13.9, 18.9, 28.8, 36.1, 43.0, 53.0, 62.9, 102.5, 102.7, 103.3, 104.5, 112.3, 112.4, 112.5, 112.6, 132.9, 138.0, 138.9, 161.9, 164.3, 164.5, 169.2, 169.5; MS 407.23 m/z (M+1).

Example 7

2-[2-(3,5-Difluoro-phenyl)-2-hydroxy-acetylamino]-pentanoic acid [1-(1-ethyl-propyl)-1H-imidazol-4-yl]-amide 2-Amino-pentanoic acid [1-(1-ethyl-propyl)-1H-imidazol-4-yl]-amide was coupled with (3,5-Difluoro-phenyl)-hydroxy-acetic acid to provide the title compound: C13 NMR (100 MHz, CDCl3) 10.7, 13.7, 13.7, 19.0, 19.1, 35.5, 35.7, 52.9, 53.2, 62.9, 73.4, 73.5, 103.4, 103.7, 105.0, 105.2, 109.6, 109.8, 109.9, 110.1, 132.5, 132.6, 137.4, 137.5, 144.1, 161.7, 161.9, 164.3, 169.2, 169.6, 171.8, 172.0; MS 423.21 m/z (M+1).

Example 8

2-(4-{2-[2-(3,5-Difluoro-phenyl)-acetylamino]-pentanoylamino}-imidazol-1-yl)-2-methyl-propionic acid methyl ester 2-[4-(2-Amino-pentanoylamino)-imidazol-1-yl]-2-methyl-propionic acid methyl ester was coupled with (3,5-Difluoro-phenyl)-acetic acid to provide the title compound: C13 NMR (100 MHz, CDCl3) 13.9, 18.9, 26.1, 26.2, 35.9, 43.0, 53.1, 53.3, 61.2, 102.5, 102.8, 103.0, 106.1, 112.3, 112.4, 112.5, 112.6, 132.0, 137.6, 138.8, 161.8, 162.0, 164.3, 164.4, 169.3, 169.4, 172.6; MS 437.20 m/z (M+1).

Example 9

2-(4-{2-[2-(3,5-Difluoro-phenyl)-2-hydroxy-acetylamino]-pentanoylamino}-imidazol-1-yl)-2-methyl-propionic acid methyl ester 2-[4-(2-Amino-pentanoylamino)-imidazol-1-yl]-2-methyl-propionic acid methyl ester was coupled with (3,5-Difluoro-phenyl)-hydroxy-acetic acid to provide the title compound: C13 NMR (100 MHz, CDCl3) 13.7, 13.8, 19.0, 19.1, 26.0, 35.3, 35.7, 53.0, 53.2, 53.3, 61.2, 61.3, 73.3, 73.4, 103.5, 103.7, 106.1, 106.3, 109.6, 109.8, 110.1, 131.6, 131.8, 137.0, 137.1, 144.0, 161.9, 164.3, 169.3, 169.6, 171.9, 172.0, 172.5; MS 453.20 m/z (M+1).

Example 10

2-{4-[2-(2-Hydroxy-3,3-dimethyl-butyrylamino)-pentanoylamino]-imidazol-1-yl}-2-methyl-propionic acid methyl ester 2-[4-(2-Amino-pentanoylamino)-imidazol-1-yl]-2-methyl-propionic acid methyl ester was coupled with (S)-2-hydroxy-3,3-dimethyl-butyric acid to provide the title compound: C13 NMR (100 MHz, CDCl$_3$) 13.9, 19.1, 26.1, 26.2, 26.3, 35.3, 35.5, 52.6, 53.3, 61.1, 79.6, 106.1, 131.9, 137.5, 169.6, 172.7, 173.1; MS 397.23 m/z (M+1).

Example 11

2-{4-[2-(2-Hydroxy-3-methyl-butyrylamino)-pentanoylamino]-imidazol-1-yl}-2-methyl-propionic acid methyl ester 2-[4-(2-Amino-pentanoylamino)-imidazol-1-yl]-2-methyl-propionic acid methyl ester was coupled with (S)-2-hydroxy-3-methyl-butyric acid to provide the title compound: C13 NMR (100 MHz, CDCl3) 13.8, 15.9, 19.1, 19.4, 26.1, 26.2, 32.1, 35.5, 52.6, 53.3, 61.2, 76.4, 106.1, 131.9, 137.5, 169.6, 172.6, 173.9; MS 383.2 m/z (M+1).

Example 12

3-(4-{2-[2-(3,5-Difluoro-phenyl)-acetylamino]-propionylamino}-imidazol-1-yl)-3-methyl-butyric acid methyl ester 3-[4-(2-Amino-propionylamino)-imidazol-1-yl]-3-methyl-butyric acid methyl ester was coupled with (3,5-Difluoro-phenyl)-acetic acid to provide the title compound: C13 NMR (100 MHz, CDCl3) 19.6, 28.1, 28.2, 3.0, 46.9, 49.1, 51.9, 56.4, 102.5, 102.8, 103.0, 105.1, 112.3, 112.5, 112.6, 131.0, 137.9, 138.7, 164.3, 169.1, 170.0; MS 423.2 m/z (M+1).

Example 13

3-{4-[2-(2-Hydroxy-3,3-dimethyl-butyrylamino)-propionylamino]-imidazol-1-yl}-3-methyl-butyric acid methyl ester 3-[4-(2-Amino-propionylamino)-imidazol-1-yl]-3-methyl-butyric acid methyl ester was coupled with (S)-2-hydroxy-3,3-dimethyl-butyric acid to provide the title compound: C13 NMR (100 MHz, CDCl3) 19.2, 26.2, 28.1, 28.2, 35.2, 47.1, 48.6, 51.9, 56.4, 79.7, 105.1, 112.4, 131.0, 137.7, 169.7, 170.0, 173.0; MS 383.3 m/z (M+1).

Example 14

4-(4-{2-[2-(3,5-Difluoro-phenyl)-acetylamino]-pentanoylamino}-imidazol-1-yl)-piperidine-1-carboxylic acid tert-butyl ester 4-(4-Amino-imidazol-1-yl)-piperidine-1-carboxylic acid tert-butyl ester was coupled with (L)-2-[2-(3,5-difluoro-phenyl)-acetylamino]-pentanoic acid to afford the title compound: C13 NMR (100 MHz, CDCl3) 13.9, 18.9, 28.6, 33.1, 36.0, 43.1, 53.0, 55.8, 80.2, 102.6, 102.9, 105.7, 112.3, 112.5, 112.6, 131.4, 137.8, 154.6, 169.1, 169.4; MS 520.2 m/z (M+1).

Example 15

2-[2-(3,5-Difluoro-phenyl)-acetylamino]-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide ester was coupled with (3,5-Difluoro-phenyl)-acetic acid to provide the title compound: C13 NMR (100 MHz, CDCl3) 14.0, 18.9, 24.3, 24.8, 25.2, 26.6, 35.8, 35.9, 43.2, 53.2, 56.0, 59.4, 67.2, 102.6, 102.9, 103.1, 105.5, 112.4, 112.4, 112.5, 112.6, 131.6, 137.4, 138.7, 138.8, 161.9, 162.1, 164.4, 164.5, 169.2, 169.2; MS m/z 462.2 (M+1).

Example 16

2-[2-(3-Trifluoromethyl-phenyl)-acetylamino]-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide ester was coupled with (3-trifluoromethylphenyl)-acetic acid to provide the title compound: C13 NMR (100 MHz, CDCl3) 13.9, 18.9, 24.2, 26.5, 35.9, 43.2, 53.1, 55.9, 59.3, 67.1, 105.4, 124.1, 126.2, 129.2, 131.5, 132.9, 136.2, 137.4, 169.3, 169.7; MS m/z 494.38 (M+1).

Example 17

2-[2-(3-Trifluoromethoxy-phenyl)-acetylamino]-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide ester was coupled with (3-trifluoromethoxyphenyl)-acetic acid to provide the title compound: C13 NMR (100 MHz, CDCl3) 13.8, 18.8, 24.2, 26.5, 35.7, 43.2, 53.1, 55.9, 59.3, 67.1, 105.4, 119.7, 122.0, 127.9, 130.2, 131.3, 137.3, 137.4, 169.2, 169.7; MS m/z 510.3 (M+1).

Example 18

2-[2-(3,5-Difluoro-phenyl)-acetylamino]-pentanoic acid [1-(1,1-dimethyl-2-morpholin-4-yl-ethyl)-1H-imidazol-4-yl]-amide 2-Amino-pentanoic acid [1-(1,1-dimethyl-2-morpholin-4-yl-ethyl)-1H-imidazol-4-yl]-amide was coupled with (3,5-Difluoro-phenyl)-acetic acid to provide the title compound: C13 NMR (100 MHz, CDCl3) 14.0, 19.0, 25.8, 35.7, 43.1, 53.3, 55.5, 59.7, 67.4, 68.6, 102.9, 105.4, 112.4, 112.6, 130.9, 136.7, 169.4, 169.5; MS m/z 478.2 (M+1).

Example 19

2-[2-(3,5-Difluoro-phenyl)-2-hydroxy-acetylamino]-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide was coupled with (3,5-Difluoro-phenyl)-hydroxy-acetic acid to afford the title compound: MS m/z 478.3 (M+1); Diastereomers were separated using a S,S-Whelk-O1 column (5 cm×25 cm), eluting with 70:30 heptane:iPrOH at a flow rate of 110 mL/min.

Example 20

2-[2-(3,5-Difluoro-phenyl)-2-hydroxy-acetylamino]-pentanoic acid [1-(1-ethyl-propyl)-1H-imidazol-4-yl]-amide 2-Amino-pentanoic acid [1-(1-ethyl-propyl)-1H-imidazol-4-yl]-amide was coupled with (3,5-Difluoro-phenyl)-hydroxy-acetic acid to afford the title compound: C13 NMR (100 MHz, CDCl3) 10.7, 13.7, 13.7, 19.0, 19.1, 35.5, 35.7, 52.9, 53.2, 62.9, 73.4, 73.5, 103.4, 103.7, 105.0, 105.2, 109.6, 109.8, 109.9, 110.1, 132.5, 132.6, 137.4, 137.5, 144.1, 161.7, 161.9, 164.3, 169.2, 169.6, 171.8, 172.0; MS 423.21 m/z (M+1); Diastereomers separated using Chiralpak AD column, elute 50:50 heptane:ethanol; Flow Rate 275 mL/min.

Example 21

2-[2-(4-Phenyl-thiazol-2-yl)-acetylamino]-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide was coupled with (4-phenyl-thiazol-2-yl)-acetic acid to afford the title compound: C13 NMR (100 MHz, CDCl3) 13.9, 19.0, 24.2, 25.6, 26.6, 26.7, 35.2, 40.3, 53.6, 55.9, 59.1, 67.2, 105.3, 113.2, 126.5, 128.4, 129.0, 131.4, 134.2, 137.4, 155.5, 163.4, 167.3, 168.6; MS m/z 509.4 (M+1).

Example 22

2-[2-(3-Trifluoromethyl-phenyl)-acetylamino]-pentanoic acid [1-(1,1-dimethyl-2-morpholin-4-yl-ethyl)-1H-imidazol-4-yl]-amide 2-Amino-pentanoic acid [1-(1,1-dimethyl-2-morpholin-4-yl-ethyl)-1H-imidazol-4-yl]-amide was coupled with (3-trifluoromethylphenyl)-acetic acid to afford the title compound: C13 NMR (100 MHz, CDCl3) 13.9, 18.9, 25.9, 35.9, 43.2, 53.1, 55.5, 59.2, 67.4, 68.8, 105.3, 112.5, 124.1, 124.2, 126.2, 126.3, 129.3, 131.7, 132.9, 136.1, 137.5, 169.3, 169.7; MS m/z 510.4 (M+1).

Example 23

2-(2-Hydroxy-3-methyl-butyrylamino)-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide was coupled with (S)-2-hydroxy-3-methyl-butyric acid to afford the title compound:
C13 NMR (100 MHz, CDCl3) 12.7, 15.2, 18.4, 18.9, 22.8, 25.3, 31.8, 33.9, 53.0, 56.8, 60.7, 63.3, 75.8, 107.5, 130.8, 131.1, 171.7, 175.7; MS m/z 408.5 (M+1).

Example 24

2-(2-Hydroxy-3,3-dimethyl-butyrylamino)-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide was coupled with (S)-2- hydroxy-3,3-dimethyl-butyric acid to afford the title compound: C13 NMR (100 MHz, CDCl3) 12.7, 18.9, 22.8, 25.2, 25.4, 33.9, 34.8, 53.0, 56.8, 60.5, 63.3, 79.0, 107.5, 131.2, 171.8, 174.8; MS m/z 422.4 (M+1).

Example 25

2-(2-Hydroxy-3-methyl-butyrylamino)-pentanoic acid [1-(1,1-dimethyl-2-morpholin-4-yl-ethyl)-1H-imidazol-4-yl]-amide 2-Amino-pentanoic acid [1-(1,1-dimethyl-2-morpholin-4-yl-ethyl)-1H-imidazol-4-yl]-amide was coupled with (S)-2-hydroxy-3-methyl-butyric acid to afford the title compound: 13C NMR (100 MHz, CDCl3) 13.9, 16.1, 19.1, 19.4, 25.9, 32.3, 35.4, 52.8, 55.5, 59.2, 67.4, 68.8, 105.3, 131.3, 137.2, 169.4, 174.1; MS m/z 424.4 (M+1).

Example 26

2-[2-(3,5-Difluoro-phenyl)-2-hydroxy-acetylamino]-pentanoic acid [1-(1,1-dimethyl-2-morpholin-4-yl-ethyl)-1H-imidazol-4-yl]-amide 2-Amino-pentanoic acid [1-(1,1-dimethyl-2-morpholin-4-yl-ethyl)-1H-imidazol-4-yl]-amide was coupled with (3,5-Difluoro-phenyl)-hydroxy-acetic acid to afford the title compound: H1 NMR (400 MHz, CDCl3) 0.8 (m, 3H), 1.40 (m, 2H), 1.48 (s, 2H), 1.70, (m, 2H), 2.20 (m, 4H), 2.42, (m, 2H), 3.58 (m, 4H), 4.80 (m, 0.5H), 4.90 (m, 0.5H), 5.12 (m, 0.5H), 5.20 (m, 0.5H), 6.72 (m, 1H) 7.08 (m, 2H), 7.39 (s, 0.5H) 7.40 (s, 0.5H), 7.46 (s, 0.5H), 7.47 (s, 0.5H); MS m/z 494.4 (M+1).

Example 27

2-(2-Hydroxy-3,3-dimethyl-butyrylamino)-pentanoic acid [1-(1,1-dimethyl-2-morpholin-4-yl-ethyl)-1H-imidazol-4-yl]-amide 2-Amino-pentanoic acid [1-(1,1-dimethyl-2-morpholin-4-yl-ethyl)-1H-imidazol-4-yl]-amide was coupled with (S)-2-hydroxy-3,3-dimethyl-butyric acid to afford the title compound: C13 NMR (100 MHz, CDCl3) 13.9, 19.2, 25.9, 26.4, 35.2, 35.3, 52.8, 55.5, 59.1, 67.5, 68.9, 80.0, 105.2, 131.3, 137.2, 169.1, 173.3; MS m/z 438.2 (M+1).

Example 28

2-[2-(3,5-Difluoro-phenyl)-acetylamino]-4-methyl-pentanoic acid [1-(1,1-dimethyl-2-pyrrolidin-1-yl-ethyl)-1H-imidazol-4-yl]-amide 2-Amino-4-methyl-pentanoic acid [1-(1,1-dimethyl-2-pyrrolidin-1-yl-ethyl)-1H-imidazol-4-yl]-amide was coupled with (3,5-Difluoro-phenyl)-acetic acid to provide the title compound: C13 NMR (100 MHz, CDCl3) 22.5, 22.9, 24.2, 25.0, 26.6, 26.7, 42.9, 43.1, 51.9, 56.0, 59.3, 67.3, 102.9, 105.5, 112.3, 112.6, 131.9, 137.4, 169.1, 169.4; MS m/z 476.3 (M+1).

Example 29

2-[2-(3,5-Difluoro-phenyl)-acetylamino]-N-[1-(1,1-dimethyl-2-pyrrolidin-1-yl-ethyl)-1H-imidazol-4-yl]-propionamide 2-Amino-N-[1-(1,1-dimethyl-2-pyrrolidin-1-yl-ethyl)-1H-imidazol-4-yl]-propionamide was coupled with (3,5-Difluoro-phenyl)-acetic acid to provide the title compound: $^1$H NMR (400 MHz) 1.41 (d, 3H), 1.51 (s, 6H), 1.48 (s, 4H), 2.32 (s, 4H), 2.7 (s, 2H), 3.5 (s, 2H), 4.88-4.83 (m, 1H), 7.44 (d, 1H, J=1.4 Hz), 6.63-6.68 (m, 1H), 6.71-6.90 (M, 2 h), 7.58 (d, 1H, J=1.7 Hz), 11.8 (brs, 1H) MS m/z 434.2 (M+1).

Example 30

(4-{2-[2-(3,5-Difluoro-phenyl)-acetylamino]-pentanoylamino}-imidazol-1-yl)-acetic acid methyl ester (4-Amino-imidazol-1-yl)-acetic acid methyl ester was coupled with 2-[2-(3,5-Difluoro-phenyl)-acetylamino]-pentanoic acid to afford the title compound: C13 NMR (100 MHz, CDCl3) 13.5, 19.1, 33.8, 42.3, 50.3, 53.6, 54.5, 102.2, 102.5, 102.7, 109.9, 112.4, 112.6, 130.0, 131.4, 139.0, 161.9, 164.2, 166.5, 171.4; MS m/z 409.1 (M+1).

Example 31

2-(4-{2-[2-(3,5-Difluoro-phenyl)-acetylamino]-pentanoylamino}-2-methyl-imidazol-1-yl)-2-methyl-propionic acid methyl ester 2-(4-Amino-2-methyl-imidazol-1-yl)-2-methyl-propionic acid methyl ester was coupled with 2-[2-(3,5-Difluoro-phenyl)-acetylamino]-pentanoic acid to afford the title compound: C13 NMR (100 MHz, CDCl3) 13.8, 14.7, 18.9, 26.1, 26.7, 35.5, 42.9, 53.3, 61.1, 102.7, 105.3, 112.3, 112.5, 134.9, 138.9, 140.9, 169.5, 169.7, 173.4; MS m/z 451.2 (M+1).

Example 32

2-[2-(3,5-Difluoro-phenyl)-acetylamino]-pentanoic acid [1-(2-methoxy-1,1-dimethyl-ethyl)-1H-imidazol-4-yl]-amide 2-Amino-pentanoic acid [1-(2-methoxy-1,1-dimethyl-ethyl)-1H-imidazol-4-yl]-amide was coupled with (3,5-Difluoro-phenyl)-acetic acid to provide the title compound: H1NMR (400 MHz, CDCl3) 0.85 (t, 3H, J=7), 1.3 (m, 2H), 1.54 (s, 6H), 1.65 (m, 1H), 1.80 (m, 1H), 3.29 (s, 3H), 3.43 (s, 2H), 3.53 (s, 3H), 4.76, (m, 1H), 6.56 (m, 1H), 6.71 (m, 1H), 6.81 (m, 2H), 7.44 (s, 1H), 7.65 (s, 1H); MS m/z 423.3 (M+1).

Example 33

4-(4-{2-[2-(3,5-Difluoro-phenyl)-acetylamino]-pentanoylamino}-imidazol-1-yl)-benzoic acid methyl ester 4-(4-Amino-imidazol-1-yl)-benzoic acid methyl ester was coupled with 2-[2-(3,5-Difluoro-phenyl)-acetylamino]-pentanoic acid to afford the title compound: C13 NMR (100 MHz, CDCl3) 14.0, 19.0, 35.8, 43.1, 52.6, 53.3, 102.7, 103.0, 103.2, 106.1, 112.4, 112.6, 120.4, 129.2, 131.7, 132.1, 138.6, 139.0, 140.6, 161.9, 162.1, 164.4, 166.2, 169.6, 169.8; MS m/z 471.2 (M+1).

Example 34

2-[2-(3,5-Difluoro-phenyl)-acetylamino]-pentanoic acid {1-[1-(2,2-dimethyl-propyl)-pyrrolidin-3-yl]-1H-imidazol-4-yl}-amide 1-[1-(2,2-Dimethyl-propyl)-pyrrolidin-3-yl]-1H-imidazol-4-ylamine was coupled with 2-[2-(3,5-Difluoro-phenyl)- acetylamino]-pentanoic acid to afford the title compound: C13 NMR (100 MHz, CDCl3) 14.0, 18.9, 28.6, 33.0, 33.4, 35.9, 43.1, 53.1, 55.7, 57.3, 63.5, 68.3, 102.6, 102.8, 103.1, 106.6, 112.3, 112.5, 112.6, 132.1, 137.7, 138.8, 161.9, 164.5, 169.1; MS m/z 476.2 (M+1).

The following Examples were prepared by methods analogous to that described above for General Procedure B, reductive amination procedure (a):

Example 35

3-{4-[2-(6,8-Difluoro-1,2,3,4-tetrahydro-naphthalen-2-ylamino)-pentanoylamino]-imidazol-1-yl}-butyric acid methyl ester 3-[4-(2-Amino-pentanoylamino)-imidazol-1-yl]-butyric acid methyl ester was reacted with 6,8-Difluoro-3,4-dihydro-1H-naphthalen-2-one to provide the title compound: MS m/z 449.3 (M+1).

Example 36

2-{4-[2-(6,8-Difluoro-1,2,3,4-tetrahydro-naphthalen-2-ylamino)-pentanoylamino]-imidazol-1-yl}-2-methyl-propionic acid methyl ester 2-[4-(2-Amino-pentanoylamino)-imidazol-1-yl]-2-methyl-propionic acid methyl ester was reacted with 6,8-Difluoro-3,4-dihydro-1H-naphthalen-2-one to provide the title compound: C13 NMR (100 MHz, CD3OH) 13.0, 18.1, 24.5, 25.4, 25.8, 27.5, 32.8, 53.1, 53.2, 57.9, 64.7, 100.8, 101.1, 109.9, 110.4, 110.8, 115.8, 128.4, 131.6, 132.3, 139.1, 139.3, 159.5, 160.2, 166.8, 171.2; MS 449.3 m/z (M+1).

Example 37

2-(6,8-Difluoro-1,2,3,4-tetrahydro-naphthalen-2-ylamino)-pentanoic acid [1-(1-ethyl-propyl)-1H-imidazol-4-yl]-amide 2-Amino-pentanoic acid [1-(1-ethyl-propyl)-1H-imidazol-4-yl]-amide was reacted with 6,8-Difluoro-3,4-dihydro-1H-naphthalen-2-one to provide the title compound: C13 NMR (100 MHz, CDCl3) 10.9, 14.1, 14.2, 19.5, 19.6, 28.2, 28.6, 28.7, 28.9, 29.6, 29.9, 36.5, 36.6, 51.9, 52.3, 60.1, 60.6, 62.9, 100.7, 100.9, 101.2, 104.2, 110.5, 110.6, 110.8, 118.2, 118.5, 132.4, 137.9, 138.0, 139.6, 139.9, 159.8, 162.1, 162.2, 172.2, 172.4; MS 419.2 m/z (M+1).

Example 38

3-{4-[2-(6,8-Difluoro-1,2,3,4-tetrahydro-naphthalen-2-ylamino)-pentanoylamino]-imidazol-1-yl}-3-methyl-butyric acid methyl ester 3-[4-(2-Amino-pentanoylamino)-imidazol-1-yl]-3-methyl-butyric acid methyl ester was reacted with 6,8-Difluoro-3,4-dihydro-1H-naphthalen-2-one to provide the title compound: C13 NMR (100 MHz, CDCl3) 14.1, 16.7, 19.5, 19.6, 28.2, 28.7, 29.6, 29.8, 36.5, 47.2, 51.9, 52.1, 52.7, 56.3, 60.2, 60.9, 101.1, 104.4, 110.6, 130.5, 137.7, 170.0; MS 463.3 m/z (M+1).

Example 39

2-[2-(3,5-Difluoro-phenyl)-acetylamino]-pentanoic acid [1-(2-isopropylamino-1,1-dimethyl-ethyl)-1H-imidazol-4-yl]-amide 2-[2-(3,5-Difluoro-phenyl)-acetylamino]-pentanoic acid [1-(1,1-dimethyl-2-oxo-ethyl)-1H-imidazol-4-yl]-amide was reacted with isopropylamine to afford the title compound: C13 NMR (100 MHz, CDCl3) 14.0, 18.9, 23.3, 26.5, 35.9, 43.2, 49.3, 53.2, 57.7, 59.0, 102.6, 102.9, 103.1, 105.1, 112.4, 112.4, 112.5, 112.6, 131.7, 137.7, 138.7, 161.9, 162.1, 164.4, 164.5, 169.1; MS m/z 450.2 (M+1).

Example 40

2-[2-(3,5-Difluoro-phenyl)-acetylamino]-pentanoic acid [1-(1,1-dimethyl-2-methylamino-ethyl)-1H-imidazol-4-yl]-amide 2-[2-(3,5-Difluoro-phenyl)-acetylamino]-pentanoic acid [1-(1,1-dimethyl-2-oxo-ethyl)-1H-imidazol-4-yl]-amide was reacted with methylamine to afford the title compound: C13 NMR (100 MHz, CDCl3) 13.9, 19.0, 26.5, 26.6, 36.0, 37.2, 43.1, 46.0, 53.2, 58.8, 62.6, 102.6, 102.8, 103.1, 105.1, 112.3, 112.6, 131.6, 137.8, 138.8, 162.0, 164.5, 169.2, 169.3; MS m/z 422.2 (M+1).

Example 41

2-[2-(3,5-Difluoro-phenyl)-acetylamino]-pentanoic acid [1-(2-benzylamino-1,1-dimethyl-ethyl)-1H-imidazol-4-yl]-amide 2-[2-(3,5-Difluoro-phenyl)-acetylamino]-pentanoic acid [1-(1,1-dimethyl-2-oxo-ethyl)-1H-imidazol-4-yl]-amide was reacted with benzylamine to afford the title compound: C13 NMR (100 MHz, CDCl3) 14.0, 18.9, 26.4, 26.5, 36.0, 43.1, 53.2, 54.1, 59.0, 59.3, 102.6, 102.9, 103.1, 105.2, 112.4, 112.6, 127.2, 128.2, 128.6, 131.7, 137.8, 138.8, 140.3, 161.9, 164.4, 164.5, 169.2; MS m/z 498.1 (M+1).

Example 42

2-[2-(3,5-Difluoro-phenyl)-acetylamino]-pentanoic acid {1-[2-(2,2-dimethyl-propylamino)-1,1-dimethyl-ethyl]-1H-imidazol-4-yl}-amide 2-[2-(3,5-Difluoro-phenyl)-acetylamino]-pentanoic acid [1-(1,1-dimethyl-2-oxo-ethyl)-1H-imidazol-4-yl]-amide was reacted with 2,2-dimethyl-propylamine to afford the title compound: C13 NMR (100 MHz, CDCl3) 14.0, 18.9, 26.3, 26.4, 27.8, 32.1, 35.9, 43.1, 53.2, 59.3, 61.2, 63.0, 102.6, 102.8, 103.1, 105.2, 112.3, 112.6, 131.7, 137.6, 138.8, 162.0, 164.4, 164.5, 169.2, 169.3; MS m/z 478.2 (M+1).

Example 43

2-[2-(3,5-Difluoro-phenyl)-acetylamino]-pentanoic acid [1-(2-dimethylamino-1,1-dimethyl-ethyl)-1H-imidazol-4-yl]-amide 2-[2-(3,5-Difluoro-phenyl)-acetylamino]-pentanoic acid [1-(1,1-dimethyl-2-oxo-ethyl)-1H-imidazol-4-yl]-amide was reacted with dimethylamine to afford the title compound: C13 NMR (100 MHz, CDCl3) 14.0, 18.9, 26.1, 26.2, 35.9, 43.2, 47.9, 53.1, 59.3, 69.9, 102.9, 105.4, 112.4, 112.6, 131.7, 137.5, 169.2; MS m/z 436.2 (M+1),

Example 44

2-[2-(3,5-Difluoro-phenyl)-acetylamino]-pentanoic acid {1-[1,1-dimethyl-2-(1-phenyl-ethylamino)-ethyl]-1H-imidazol-4-yl}-amide 2-[2-(3,5-Difluoro-phenyl)-acetylamino]-pentanoic acid [1-(1,1-dimethyl-2-oxo-ethyl)-1H-imidazol-4-yl]-amide was reacted with 1-phenyl-ethylamine to afford the title compound: C13 NMR (100 MHz, CDCl3) 14.0, 19.0, 24.9, 26.0, 27.0, 36.0, 43.2, 53.2, 57.9, 58.6, 58.9, 102.6, 102.9, 103.1, 105.2, 112.4, 112.6, 112.6, 126.8, 127.1, 128.6, 131.7, 137.8, 138.8, 145.7, 161.9, 164.4, 164.5, 169.3; MS m/z 512.3 (M+1).

Example 45

2-[2-(3,5-Difluoro-phenyl)-acetylamino]-pentanoic acid [1-(1,1-dimethyl-3-morpholin-4-yl-propyl)-1H-imidazol-4-yl]-amide 2-[2-(3,5-Difluoro-phenyl)-acetylamino]-pentanoic acid [1-(1,1-dimethyl-3-oxo-propyl)-1H-imidazol-4-yl]-amide was reacted with morpholine to afford the title compound: MS m/z 492.2 (M+1).

Example 46

2-[2-(3,5-Difluoro-phenyl)-acetylamino]-pentanoic acid [1-(1,1-dimethyl-3-pyrrolidin-1-yl-propyl)-1H-imidazol-4-yl]-amide 2-[2-(3,5-Difluoro-phenyl)-acetylamino]-pentanoic acid [1-(1,1-dimethyl-3-oxo-propyl)-1H-imidazol-4-yl]-amide was reacted with pyrrolidine to afford the title compound: C13 NMR (100 MHz, CDCl3) 14.0, 18.9, 23.6, 28.4, 28.7, 36.0, 42.1, 43.2, 51.3, 53.1, 54.4, 57.5, 103.0, 105.3, 112.4, 112.6, 131.2, 137.8, 169.0, 169.2. MS m/z 476.2 (M+1).

Example 47

2-(6,8-Difluoro-1,2,3,4-tetrahydro-naphthalen-2-ylamino)-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide was reacted with 6,8-Difluoro-3,4-dihydro-1H-naphthalen-2-one to provide the title compound: C13 NMR (100 MHz, CDCl3) 14.2, 19.5, 19.6, 24.3, 26.6, 26.7, 28.2, 28.3, 28.8, 28.9, 29.7, 29.8, 36.6, 36.6, 52.1, 52.6, 56.0, 59.1, 59.1, 60.2, 60.8, 67.3, 100.8, 101.1, 101.3, 104.8, 110.5, 110.7, 131.1, 137.4, 172.2, 172.4; MS m/z 474.3 (M+1).

Example 48

2-(5-Chloro-indan-2-ylamino)-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide was reacted with 5-Chloro-indan-2-one to provide the title compound: C13 NMR (100 MHz, CDCl3) 14.2, 19.5, 24.3, 26.6, 26.7, 36.4, 39.3, 39.8, 40.0, 40.4, 56.0, 59.1, 59.2, 61.4, 67.3, 104.8, 125.1, 125.2, 125.9, 126.0, 126.9, 126.9, 131.2, 137.3, 140.1, 143.2, 143.6, 172.0; MS m/z 458.4 (M+1).

Example 49

2-(Indan-2-ylamino)-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide was reacted with 2-indanone to provide the title compound: C13 NMR (100 MHz, CDCl3) 14.2, 19.5, 24.3, 26.6, 26.7, 36.4, 39.9, 40.6, 56.0, 59.0, 61.4, 67.3, 104.8, 124.9, 125.0, 126.7, 126.8, 131.2, 137.4, 141.2, 141.7, 172.2; MS m/z 424.4 (M+1).

Example 50

2-(6-Fluoro-1,2,3,4-tetrahydro-naphthalen-2-ylamino)-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide was reacted with 6-Fluoro-3,4-dihydro-1H-naphthalen-2-one to provide the title compound: C13 NMR (100 MHz, CDCl3) 14.2, 19.6, 19.6, 24.3, 26.6, 28.1, 28.3, 29.2, 30.1, 35.9, 36.5, 36.6, 36.7, 53.2, 53.4, 56.0, 59.1, 60.4, 60.7, 67.3, 104.7, 104.8, 112.9, 113.1, 114.8, 114.9, 115.0, 115.1, 130.2, 130.7, 130.8, 130.8, 131.1, 137.3, 137.8, 138.1, 160.1, 162.5, 172.5; MS m/z 456.4 (M+1).

Example 51

2-(6-Chloro-1,2,3,4-tetrahydro-naphthalen-2-ylamino)-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide was reacted with 6-chloro-3,4-dihydro-1H-naphthalen-2-one to provide the title compound: C13 NMR (100 MHz, CDCl3) 14.2, 19.6, 19.6, 24.3, 26.6, 27.9, 28.0, 29.2, 30.0, 36.0, 36.5, 36.6, 36.9, 53.1, 53.3, 56.0, 59.1, 60.5, 60.8, 67.3, 104.7, 126.1, 128.5, 128.7, 130.7, 130.8, 131.2, 131.5, 131.6, 133.6, 137.3, 137.7, 138.0, 172.4; MS m/z 472.4 (M+1).

Example 52

2-(6,8-Dichloro-1,2,3,4-tetrahydro-naphthalen-2-ylamino)-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide was reacted with 6,8-dichloro-3,4-dihydro-1H-naphthalen-2-one to provide the title compound: C13 NMR (100 MHz, CDCl3) 14.2, 19.5, 19.6, 24.3, 26.6, 26.6, 26.7, 28.5, 29.5, 34.0, 34.7, 36.6, 52.5, 53.2, 56.0, 59.1, 59.2, 60.1, 60.8, 67.3, 104.8, 126.7, 127.2, 127.3, 131.1, 131.5, 131.7, 131.8, 131.9, 135.3, 137.3, 139.7, 140.0, 172.2, 172.4; MS m/z 506.4, 508.4 (M+1).

Example 53

2-(5,7-Dimethyl-1,2,3,4-tetrahydro-naphthalen-2-ylamino)-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide was reacted with 5,7-dimethyl-3,4-dihydro-1H-naphthalen-2-one to provide the title compound: C13 NMR (100 MHz, CDCl3) 14.2, 19.5, 19.6, 21.0, 24.3, 25.3, 25.6, 26.6, 29.7, 30.7, 36.6, 37.1, 38.0, 53.0, 53.3, 56.0, 59.1, 60.4, 60.8, 67.3, 104.7, 127.9, 28.0, 128.6, 128.7, 131.1, 131.3, 131.6, 134.6, 135.1, 135.2, 136.4, 137.3, 172.5, 172.6; MS m/z 466.5 (M+1).

Example 54

2-(1,2,3,4-Tetrahydro-naphthalen-2-ylamino)-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide was reacted with 3,4-Dihydro-1H-naphthalen-2-one to provide the title compound: C13 NMR (100 MHz, CDCl3) 14.2, 19.5, 19.6, 24.3, 26.6, 28.0, 28.3, 29.5, 30.5, 36.5, 36.6, 36.7, 37.5, 53.3, 53.6, 56.0, 59.1, 60.4, 60.8, 67.3, 104.7, 126.0, 126.1, 126.2, 128.8, 128.9, 129.5, 129.6, 131.1, 134.8, 135.3, 135.9, 136.3, 137.3, 172.6; MS m/z 438.5 (M+1).

Example 55

2-(6-Isopropyl-1,2,3,4-tetrahydro-naphthalen-2-ylamino)-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide was reacted with 6-Isopropyl-3,4-dihydro-1H-naphthalen-2-one to provide the title compound: C13 NMR (100 MHz, CDCl3) 14.2, 19.5, 19.6, 24.3, 26.6, 26.7, 28.2, 28.5, 29.6, 30.6, 33.9, 36.4, 36.5, 37.3, 53.4, 53.8, 56.0, 59.1, 60.4, 60.8, 67.3, 104.7, 124.2, 126.7, 126.8, 129.5, 129.6, 131.1, 132.2, 132.7, 135.7, 136.0, 137.3, 146.7, 146.8, 172.5, 172.6; MS m/z 480.5 (M+1).

Example 56

2-[2-(2-Fluoro-phenyl)-1-methyl-ethylamino]-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide was reacted with 1-(2-Fluoro-phenyl)-propan-2-one to provide the title compound: C13 NMR (100 MHz, CDCl3) 14.2, 19.0, 19.4, 20.2, 21.2, 24.3, 26.6, 36.1, 36.5, 37.1, 37.3, 53.8, 54.3, 56.0, 59.0, 60.6, 61.2, 67.3, 104.7, 115.4, 115.6, 124.1, 124.2, 126.1, 128.2, 128.2, 131.1, 131.8, 131.9, 137.3, 162.7, 172.5; MS m/z 444.4 (M+1).

Example 57

2-[1-Methyl-2-(3-trifluoromethyl-phenyl)-ethylamino]-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide was reacted with 1-(3-trifluoromethyl-phenyl)-propan-2-one to provide the title compound: C13 NMR (100 MHz, CDCl3) 14.0, 14.2, 19.1, 19.5, 20.0, 21.1, 24.3, 26.6, 26.6, 36.1, 36.5, 43.5, 44.1, 54.6, 55.2, 56.0, 59.1, 60.8, 61.1, 67.3, 104.6, 104.7, 123.4, 126.2, 129.0, 129.2, 131.1, 133.0, 137.2, 140.1, 172.3; MS m/z 494.3 (M+1).

Example 58

2-(5,7-Difluoro-1,2,3,4-tetrahydro-naphthalen-2-ylamino)-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide was reacted with 5,7-Difluoro-3,4-dihydro-1H-naphthalen-2-one to provide the title compound: C13 NMR (100 MHz, CDCl3) 14.2, 19.6, 19.6, 20.6, 24.3, 26.6, 28.4, 29.3, 36.5, 36.6, 37.1, 52.6, 56.0, 59.1, 60.6, 67.2, 101.3, 104.7, 111.2, 131.1, 172.3; MS m/z 474.4 (M+1).

Example 59

2-(6-Bromo-1,2,3,4-tetrahydro-naphthalen-2-ylamino)-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide was reacted with 6-bromo-3,4-dihydro-1H-naphthalen-2-one to provide the title compound: C13 NMR (100 MHz, CDCl3) 14.2, 19.6, 19.6, 24.3, 26.6, 27.8, 28.0, 29.1, 30.0, 36.0, 36.5, 36.6, 36.9, 53.0, 53.1, 56.0, 59.1, 59.1, 60.5, 60.7, 67.3, 104.7, 104.8, 119.6, 119.7, 129.0, 131.1, 131.1, 131.5, 131.6, 133.7, 134.2, 127.3, 137.3, 138.2, 138.5, 172.4, 172.4; MS m/z 516.3, 518.3 (M+1).

Example 60

2-[2-(3,5-Difluoro-phenyl)-ethylamino]-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide was reacted with (3,5-Difluoro-phenyl)-acetaldehyde to provide the title compound: C13 NMR (100 MHz, CDCl3) 14.1, 19.4, 24.3, 26.7, 36.0, 36.4, 50.0, 56.0, 59.1, 63.1, 67.2, 101.8, 102.1, 102.3, 104.8, 111.5, 111.8, 131.2, 137.3, 143.5, 162.0, 162.1, 164.5, 164.6, 171.7; MS m/z 448.4 (M+1).

Example 61

2-[2-(3,5-Difluoro-phenyl)-1-methyl-ethylamino]-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide was reacted with 1-(3,5-difluoro-phenyl)-propan-2-one to provide the title compound: C13 NMR (100 MHz, CDCl3) 14.0, 14.1, 19.2, 19.5, 20.1, 21.1, 24.3, 26.6, 36.1, 36.6, 43.6, 44.1, 54.4, 54.9, 56.0, 59.1, 59.1, 60.9, 61.1, 67.3, 101.8, 101.9, 102.0, 102.2, 102.3, 102.4, 104.7, 104.7, 112.0, 112.1, 112.2, 112.3, 112.4, 112.5, 131.1, 137.2, 137.3, 143.1, 143.1, 161.8, 162.0, 164.3, 164.4, 172.1, 172.4; MS m/z 462.4 (M+1).

Example 62

2-(6,8-Difluoro-1,2,3,4-tetrahydro-naphthalen-2-ylamino)-pentanoic acid [1-(1-ethyl-propyl)-1H-imidazol-4-yl]-amide 2-Amino-pentanoic acid [1-(1-ethyl-propyl)-1H-imidazol-4-yl]-amide was reacted with 6,8-Difluoro-3,4-dihydro-1H-naphthalen-2-one to provide the title compound: C13 NMR (100 MHz, CDCl3) 10.9, 14.1, 14.2, 19.5, 19.6, 28.2, 28.6, 28.7, 28.9, 29.6, 29.9, 36.5, 36.6, 51.9, 52.3, 60.1, 60.6, 62.9, 100.7, 100.9, 101.2, 104.2, 110.5, 110.6, 110.8, 118.2, 118.5, 132.4, 137.9, 138.0, 139.6, 139.9, 159.8, 162.1, 162.2, 172.2, 172.4; MS 419.2 m/z (M+1); Chiral Separation using Chiralpak AD column, elute 85:15 heptane:ethanol; Flow Rate 275 mL/min.

Example 63

2-(6,8-Difluoro-1,2,3,4-tetrahydro-naphthalen-2-ylamino)-pentanoic acid [1-(1,1-dimethyl-3-morpholin-4-yl-propyl)-1H-imidazol-4-yl]-amide 2-Amino-pentanoic acid [1-(1,1-dimethyl-3-morpholin-4-yl-propyl)-1H-imidazol-4-yl]-amide was reacted with 6,8-Difluoro-3,4-dihydro-1H-naphthalen-2-one to provide the title compound: $^{13}$C NMR 14.2, 19.5, 19.6, 28.2, 28.3, 28.5, 28.6, 28.6, 28.7, 28.8, 29.7, 29.8, 30.8, 36.5, 36.6, 39.8, 52.3, 52.7, 54.0, 57.2, 57.3, 60.3, 60.8, 67.1, 100.8, 101.1, 101.3, 104.6, 104.7, 110.5, 110.6, 110.8, 110.9, 130.5, 137.6, 137.7, 139.9, 159.7, 162.3, 172.3, 172.5; MS m/z 504.2 (M+1).

Example 64

2-(6,8-Difluoro-1,2,3,4-tetrahydro-naphthalen-2-ylamino)-pentanoic acid [1-(1,1-dimethyl-2-morpholin-4-yl-ethyl)-1H-imidazol-4-yl]-amide 2-Amino-pentanoic acid [1-(1,1-dimethyl-2-morpholin-4-yl-ethyl)-1H-imidazol-4-yl]-amide was reacted with 6,8-Difluoro-3,4-dihydro-1H-naphthalen-2-one to provide the title compound: Diast #1 (RT 12 min) 14.2, 19.5, 2.9, 26.0, 28.2, 28.9, 29.7, 36.5, 52.9, 55.5, 58.9, 60.9, 67.5, 68.9, 101.1, 104.5, 110.7, 131.2, 137.4, 172.4; MS m/z 490.3 (M+1). Diast #2 (RT 18 min) 14.2, 19.6, 25.9, 26.0, 28.3, 28.9, 29.6, 36.5, 52.5, 55.5, 58.8, 60.4, 67.5, 68.9, 101.1, 104.5, 110.6, 131.2, 137.3, 172.2; MS m/z 490.3 (M+1). Chiral sep using a Kromasil TBB column, elute 95/5, heptane/IPA, flow rate 85 ml/min.

Example 65

2-[2-(3,5-Difluoro-phenyl)-acetylamino]-pentanoic acid {1-[1,1-dimethyl-2-(1-phenyl-ethylamino)-ethyl]-1H-imidazol-4-yl}-amide 2-[2-(3,5-Difluoro-phenyl)-acetylamino]-pentanoic acid [1-(1,1-dimethyl-2-oxo-ethyl)-1H-imidazol-4-yl]-amide was reacted with 1-phenyl-ethylamine to afford the title compound: C13 NMR (100 MHz, CDCl3) 13.9, 18.9, 24.9, 25.9, 26.9, 36.0, 43.1, 53.1, 57.9, 58.5, 58.9, 102.6, 102.9, 103.1, 105.2, 112.3, 112.5, 112.6, 126.7, 127.1, 128.6, 131.7, 137.7, 138.7, 145.7, 161.9, 164.4, 164.5, 169.2; MS m/z 512.3 (M+1).

Example 66

2-(6,8-Dichloro-1,2,3,4-tetrahydro-naphthalen-2-ylamino)-pentanoic acid [1-(1,1-dimethyl-2-morpholin-4-yl-ethyl)-1H-imidazol-4-yl]-amide 2-Amino-pentanoic acid [1-(1,1-dimethyl-2-morpholin-4-yl-ethyl)-1H-imidazol-4-yl]-amide was reacted with 6,8-Dichloro-3,4-dihydro-1H-naphthalen-2-one to provide the title compound: C13 NMR (100 MHz, CDCl3) 14.2, 19.5, 25.9, 26.0, 28.5, 29.4, 34.0, 34.6, 36.5, 52.7, 53.4, 55.5, 58.9, 60.9, 67.5, 68.9, 104.6, 126.7, 127.2, 127.3, 131.2, 131.4, 131.8, 137.4, 139.9.

Example 67

2-(6,8-Difluoro-1,2,3,4-tetrahydro-naphthalen-2-ylamino)-4-methyl-pentanoic acid [1-(1,1-dimethyl-2-pyrrolidin-1-yl-ethyl)-1H-imidazol-4-yl]-amide 2-Amino-4-methyl-pentanoic acid [1-(1,1-dimethyl-2-pyrrolidin-1-yl-ethyl)-1H-imidazol-4-yl]-amide was reacted with 6,8-Dichloro-3,4-dihydro-1H-naphthalen-2-one to provide the title compound: MS m/z 448.4 (M+1).

Example 68

2-(6,8-Difluoro-1,2,3,4-tetrahydro-naphthalen-2-ylamino)-N-[1-(1,1-dimethyl-2-pyrrolidin-1-yl-ethyl)-1H-imidazol-4-yl]-propionamide 2-Amino-N-[1-(1,1-dimethyl-2-pyrrolidin-1-yl-ethyl)-1H-imidazol-4-yl]-propionamide was reacted with 6,8-Dichloro-3,4-dihydro-1H-naphthalen-2-one to provide the title compound: C13 NMR (100 MHz, CDCl3) 20.5, 24.2, 26.6, 28.2, 28.9, 29.0, 29.5, 29.7, 51.9, 52.3, 55.5, 56.0, 56.0, 59.1, 59.1, 67.2, 100.7, 101.0, 101.2, 104.8, 110.6, 110.8, 118.1, 131.1, 137.3, 139.9, 159.8, 162.3, 172.5, 172.6; MS m/z 446.2 (M+1).

Example 69

2-(6,8-Difluoro-1,2,3,4-tetrahydro-naphthalen-2-ylamino)-pentanoic acid [1-(2-dimethylamino-1,1-dimethyl-ethyl)-1H-imidazol-4-yl]-amide 2-(6,8-Difluoro-1,2,3,4-tetrahydro-naphthalen-2-ylamino)-pentanoic acid [1-(1,1-dimethyl-2-oxo-ethyl)-1H-imidazol-4-yl]-amide was reacted with dimethyl amine to afford the title compound: C13 NMR (100 MHz, CDCl3) 14.2, 19.5, 19.6, 26.2, 26.2, 26.3, 28.2, 28.3, 28.8, 29.6, 29.8, 36.6, 48.0, 52.3, 52.8, 58.9, 59.0, 60.3, 60.8, 70.0, 101.0, 104.6, 110.7, 131.2, 137.3, 159.8, 162.2, 172.4, 183.1, 183.9; MS m/z 448.4 (M+1).

Example 70

4-{4-[2-(6,8-Difluoro-1,2,3,4-tetrahydro-naphthalen-2-ylamino)-pentanoylamino]-imidazol-1-yl}-benzoic acid methyl ester 4-[4-(2-Amino-pentanoylamino)-imidazol-1-yl]-benzoic acid methyl ester was reacted with 6,8-Difluoro-3,4-dihydro-1H-naphthalen-2-one to provide the title compound: MS m/z 483.2 (M+1).

Example 71

2-(6,8-Difluoro-1,1-dimethyl-1,2,3,4-tetrahydro-naphthalen-2-ylamino)-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide was reacted with 6,8-Difluoro-1,1-dimethyl-3,4-dihydro-1H-naphthalen-2-one to afford the title compound: C13 NMR (100 MHz, CDCl3) 14.3, 19.4, 19.7, 22.5, 23.0, 24.3, 24.8, 26.3, 26.6, 27.4, 27.5, 29.7, 36.4, 37.1, 38.0, 45.8, 47.6, 56.0, 59.2, 60.7, 62.5, 63.0, 65.5, 67.3, 104.7, 104.8, 111.0, 110.2, 112.5, 131.1, 131.2, 137.2, 172.2; MS m/z 502.3. (M+1).

Example 72

2-(6-Isopropyl-1,2,3,4-tetrahydro-naphthalen-2-ylamino)-pentanoic acid [1-(1,1-dimethyl-2-pyrrolidin-1-yl-ethyl)-1H-imidazol-4-yl]-amide 2-Amino-pentanoic acid [1-(1,1-dimethyl-2-pyrrolidin-1-yl-ethyl)-1H-imidazol-4-yl]-amide was reacted with 6-Isopropyl-3,4-dihydro-1H-naphthalen-2-one to afford the title compound: C13 NMR (100 MHz, CDCl3) 14.1, 19.5, 19.6, 24.2, 26.6, 26.7, 28.2, 28.4, 29.6, 30.6, 33.9, 36.3, 36.5, 37.2, 53.4, 53.7, 56.0, 59.1, 60.3, 60.8, 67.3, 104.6, 124.1, 126.7, 126.8, 129.5, 129.6, 131.1, 132.1, 135.7, 136.0, 137.3, 146.7, 146.8, 172.4, 172.6; MS m/z 480.5 (M+1).

The following examples were prepared using General procedure I:

Example 73

2-(6,8-Difluoro-1,2,3,4-tetrahydro-naphthalen-2-ylamino)-pentanoic acid [1-(2-hydroxy-1,1-dimethyl-ethyl)-1H-imidazol-4-yl]-amide 2-{4-[2-(6,8-Difluoro-1,2,3,4-tetrahydro-naphthalen-2-ylamino)-pentanoylamino]-imidazol-1-yl}-2-methyl-propionic acid methyl ester was reduced using LAH to afford the title compound: mixture of diasteromers C13 NMR (100 MHz, CDCl3) 14.1, 14.2, 14.4, 19.4, 19.5, 21.2, 22.7, 24.7, 24.8, 24.9, 28.1, 28.3, 28.8, 28.9, 29.6, 29.7, 36.4, 52.1, 52.7, 59.3, 60.0, 60.6, 60.7, 70.5, 100.8, 101.0, 101.3, 104.6, 110.5, 110.6, 110.7, 110.8, 117.9, 118.1, 118.4, 118.6, 131.2, 131.3, 137.3, 137.4, 139.5, 139.6, 139.7, 139.8, 139.9, 139.9, 159.7, 159.8, 159.9, 162.1, 162.2, 162.3, 172.4, 172.6; MS m/z 421.4 (M+1).

Example 74

2-[2-(3,5-Difluoro-phenyl)-acetylamino]-pentanoic acid [1-(2-hydroxy-ethyl)-1H-imidazol-4-yl]-amide (4-{2-[2-(3,5-Difluoro-phenyl)-acetylamino]-pentanoylamino}-imidazol-1-yl)-acetic acid methyl ester was reduced using LAH to afford the title compound: C13 NMR (100 MHz, CDCl3) 12.8, 19.0, 34.3, 41.6, 49.8, 53.6, 61.1, 101.6, 101.8, 102.1, 108.4, 111.9, 112.1, 112.1, 134.0, 136.6, 162.0, 164.5, 170.3, 171.4; MS m/z 381.1 (M+1).

Example 75

2-[2-(3,5-Difluoro-phenyl)-acetylamino]-pentanoic acid [1-(2-hydroxy-1,1-dimethyl-ethyl)-1H-imidazol-4-yl]-amide 2-(4-{2-[2-(3,5-Difluoro-phenyl)-acetylamino]-pentanoylamino}-imidazol-1-yl)-2-methyl-propionic acid methyl ester was reduced with LAH to afford the title compound: C13 NMR (100 MHz, CDCl3) 13.9, 18.9, 24.7, 24.8, 35.5, 42.8, 53.2, 59.5, 70.1, 102.5, 102.8, 103.0, 105.6, 112.3, 112.4, 112.5, 112.6, 131.8, 137.1, 138.6, 138.7, 161.8, 161.9, 164.3, 164.4, 169.4, 169.8; MS 409.2 m/z (M+1).

Example 76

2-[2-(3,5-Difluoro-phenyl)-acetylamino]-pentanoic acid [1-(3-hydroxy-1,1-dimethyl-propyl)-1H-imidazol-4-yl]-amide 3-(4-{2-[2-(3,5-Difluoro-phenyl)-acetylamino]-pentanoylamino}-imidazol-1-yl)-3-methyl-butyric acid methyl ester was reduced to afford the title compound: C13 NMR (100 MHz, CDCl3) 14.0, 18.9, 26.2, 28.8, 29.3, 36.1, 43.1, 44.9, 53.1, 57.5, 58.2, 103.1, 105.2, 112.3, 112.6, 131.5, 137.7, 168.9, 169.7; MS 423.2 m/z (M+1).

Example 77

2-[2-(3,5-Difluoro-phenyl)-acetylamino]-pentanoic acid (1-piperidin-4-yl-1H-imidazol-4-yl)-amide 4-(4-{2-[2-(3,5-Difluoro-phenyl)-acetylamino]-pentanoylamino}-imidazol-1-yl)-piperidine-1-carboxylic acid tert-butyl ester (1.1 g, 2.1 mmole) was dissolved in 20 mL of methylene chloride and 1.6 mL of trifluoroacetic acid was added. Reaction stirred overnight, extrated with sodium bicarbonate, and used without further purification to afford the title compound: C13 NMR (100 MHz, CDCl3) 12.8, 18.9, 29.9, 34.1, 41.5, 43.2, 52.4, 53.7, 101.8, 105.6, 111.9, 112.1, 132.0, 137.1, 170.4, 171.5; MS 420.1 m/z (M+1).

Example 78

2-[2-(3,5-Difluoro-phenyl)-acetylamino]-pentanoic acid [1-(1-methyl-piperidin-4-yl)-1H-imidazol-4-yl]-amide 2-[2-(3,5-Difluoro-phenyl)-acetylamino]-pentanoic acid (1-piperidin-4-yl-1H-imidazol-4-yl)-amide (200 mg, 4.8 mmol) was dissolved in 5 mL of THF and 0.5 mL of water and 0.04 mL of 38% formaldehyde and 0.06 mL of formic acid was added. The reaction was heated for 12 h at 80° C. The solution was extracted with methylene chloride and sodium bicarbonate. The resultant organics were concentrated and purified by silica gel chromatography to afford the title compound: C13 NMR (100 MHz, CDCl3) 13.9, 18.9, 33.3, 36.0, 43.1, 46.1, 53.0, 54.7, 55.3, 102.6, 102.9, 103.1, 105.9, 112.3, 112.6, 131.5, 137.7, 138.7, 162.0, 164.5, 169.2; MS 432.2 m/z (M+1).

Example 79

2-[2-(3,5-Difluoro-phenyl)-acetylamino]-pentanoic acid [1-(1-acetyl-piperidin-4-yl)-1H-imidazol-4-yl]-amide 2-[2-(3,5-Difluoro-phenyl)-acetylamino]-pentanoic acid (1-piperidin-4-yl-1H-imidazol-4-yl)-amide (200 mg, 4.8 mmol) was dissolved in 5 mL of methylene chloride, charged with 0.08 mL of triethylamine, and 0.03 mL of acetylchloride at 0° C. The reaction was stirred for 12 h, quenched with sodium bicarbonate, extrated with methylene chloride and concentrated. The compound was purified by silica gel chromatography to afford the title compound: C13 NMR (100 MHz, CDCl3) 13.9, 18.9, 21.6, 32.8, 33.7, 36.0, 40.7, 43.0, 45.4, 53.1, 55.5, 102.6, 102.8, 103.1, 105.6, 105.7, 112.3, 112.4, 112.5, 131.5, 137.8, 169.1, 169.3, 169.5; MS 462.25 m/z (M+1).

Example 80

2-[2-(3,5-Difluoro-phenyl)-acetylamino]-pentanoic acid {1-[1-(3,3-dimethyl-butyryl)-piperidin-4-yl]-1H-imidazol-4-yl}-amide Following the procedure for Example 21; 2-[2-(3,5-Difluoro-phenyl)-acetylamino]-pentanoic acid (1-piperidin-4-yl-1H-imidazol-4-yl)-amide was coupled with t-butylacetylchloride to afford the title compound: C13 NMR (100 MHz, CDCl3) 13.9, 18.9, 30.2, 31.6, 33.0, 33.8, 36.0, 40.6, 43.0, 44.9, 45.7, 53.0, 55.7, 102.6, 102.8, 103.1, 105.8, 112.3, 112.4, 112.5, 112.6, 131.5, 137.8, 138.8, 138.9, 161.8, 162.0, 164.3, 164.5, 169.3, 169.5, 170.6; MS 518.30 m/z (M+1).

Example 81

2-[2-(3,5-Difluoro-phenyl)-acetylamino]-pentanoic acid {1-[1-(3,3-dimethyl-butyl)-piperidin-4-yl]-1H-imidazol-4-yl}-amide 2-[2-(3,5-Difluoro-phenyl)-acetylamino]-pentanoic acid (1-piperidin-4-yl-1H-imidazol-4-yl)-amide (100 mg, 2.4 mmol) was charged with 1 mL of THF, 1 mL of Dichloroethane, 0.06 mL of triethyamine, 0.03 mL of 3,3-dimethylbutyraldehyde, and 63 mg of sodiumtriacetoxyborohydride. The reaction was stirred overnight, quenched with sodiumbicarbonate, extracted with methylene chloride, and the resultant oil purified by silica gel chromatography to afford the title compound: C13 NMR (100 MHz, CDCl3) 13.9, 18.8, 29.7, 29.9, 33.3, 36.0, 40.9, 43.1, 52.9, 53.1, 54.5, 55.9, 102.8, 103.1, 105.9, 112.3, 112.4, 112.5, 112.6, 131.5, 137.6, 169.2; MS 504.3 m/z (M+1)

Example 82

2-[2-(3,5-Difluoro-phenyl)-acetylamino]-pentanoic acid {1-[1-(2,2-dimethyl-propyl)-piperidin-4-yl]-1H-imidazol-4-yl}-amide Following the procedure for Example 81; 2-[2-(3,5-Difluoro-phenyl)-acetylamino]-pentanoic acid (1-piperidin-4-yl-1H-imidazol-4-yl)-amide was reacted with trimethylacetaldehyde to afford the title compound: C13 NMR (100 MHz, CDCl3) 14.0, 18.8, 27.8, 30.5, 33.3, 33.8, 36.0, 43.1, 53.1, 53.3, 55.9, 69.6, 102.6, 102.9, 103.1, 105.8, 112.3, 112.6, 131.5, 137.6, 138.7, 162.0, 164.4, 169.2; MS 490.3 m/z (M+1).

Example 83

2-[6-(4-Fluoro-phenyl)-1,2,3,4-tetrahydro-naphthalen-2-ylamino]-pentanoic acid [1-(1,1-dimethyl-2-pyrrolidin-1-yl-ethyl)-1H-imidazol-4-yl]-amide 2-(6-Bromo-1,2,3,4-tetrahydro-naphthalen-2-ylamino)-pentanoic acid [1-(1,1-dimethyl-2-pyrrolidin-1-yl-ethyl)-1H-imidazol-4-yl]-amide (1 equiv) is dissolved in 3:1 dimethoxyethane:water and Pd(PPh$_3$)$_4$ (0.03 equiv.) and sodium carbonate (3 equiv) is added and the reaction heated at 90° C. overnight. The reaction is cooled, water added, and extracted with methylene chloride. The solvent is dried, concentrated and the residue purified by silica gel chromatography to provide the title compound: MS m/z 532.5 (M+1).

Example 84

2-[(6,8-Difluoro-1,2,3,4-tetrahydro-naphthalen-2-yl)-methyl-amino]-pentanoic acid [1-(1,1-dimethyl-2-pyrrolidin-1-yl-ethyl)-1H-imidazol-4-yl]-amide 2-(6,8-Difluoro-1,2,3,4-tetrahydro-naphthalen-2-ylamino)-pentanoic acid [1-(1,1-dimethyl-2-pyrrolidin-1-yl-ethyl)-1H-imidazol-4-yl]-amide (1 equiv) is dissolved in methanol and to the reaction is added formalin (4 equiv) and sodium cyanoborohydride (2.0 equiv). The reaction is stirred at rt for 3 h, quenched with water, and extracted with methylene chloride. The solvent is dried, concentrated and the residue purified by silica gel chromatography to provide the title compound: Diagnostic C13 NMR (100 MHz, CDCl3) 55.9, 57.0, 57.1, 56.0, 65.1, 67.2, 101.0, 104.5, 110.5, 110.7, 131.1; MS m/z 488.4 (M+1).

Example 85

2-[2-(3,5-Difluoro-phenyl)-acetylamino]-pentanoic acid [7-(2,2-dimethyl-propyl)-5,5-dimethyl-5,6,7,8-tetrahydro-imidazo[1,5-a]pyrazin-1-yl]-amide {1-[1-(1,1-Dimethyl-2-oxo-ethyl)-1H-imidazol-4-ylcarbamoyl]-butyl}-carbamic acid tert-butyl ester (1 equiv) was combined with 2,2-dimethyl propyl amine (2 equiv), 4A molecular sieves, and methylene chloride. To the reaction is added sodium borohyrdride (1 equiv) and the reaction stirred for 3 h, quenched with sodium bicarbonate, and extracted with methylene chloride. The solvent is dried, concentrated and the residue purified by silica gel chromatography to provide the title compound:

To the above amine (1 equiv) in 9:1 THF:water is added formalin (1.1 equiv) and formic acid (2 equiv) and the reaction heated to 80° C. for 5 h. The reaction was quenched with sodium bicarbonate and extracted with methylene chloride. The solvent is dried, concentrated and the residue purified by silica gel chromatography to provide {1-[7-(2,2-dimethyl-propyl)-5,5-dimethyl-5,6,7,8-tetrahydro-imidazo[1,5-a]pyrazin-1-ylcarbamoyl]-butyl}-carbamic acid tert-butyl ester.

Following general procedure D, deprotection afforded 2-Amino-pentanoic acid [7-(2,2-dimethyl-propyl)-5,5-dimethyl-5,6,7,8-tetrahydro-imidazo[1,5-a]pyrazin-1-yl]-amide Following general coupling procedure A, 2-amino-pentanoic acid [7-(2,2-dimethyl-propyl)-5,5-dimethyl-5,6,7,8-tetrahydro-imidazo[1,5-a]pyrazin-1-yl]-amide is coupled with (3,5-difluoro-phenyl)-acetic acid to provide the title compound: Diagnostic C13 NMR (100 MHz, CDCl3) 13.5, 18.9, 27.4, 28.1, 28.6, 33.5, 35.4, 43.1, 52.8, 53.2, 56.2, 65.7, 69.9, 102.9, 112.3, 112.6, 117.4, 129.2, 169.9; MS m/z 490.5 (M+1).

Example 86

2-(6,8-Difluoro-1,2,3,4-tetrahydro-naphthalen-2-ylamino)-pentanoic acid {1-[2-(2,2-dimethyl-propylamino)-1,1-dimethyl-ethyl]-1H-imidazol-4-yl}-amide Combine L-norvaline methyl ester-hydrochloride (1 equiv) with 6,8-difluoro-3,4-dihydro-1H-naphthalen-2-one (1 equiv) in methylene chloride and stir 30 min. and add sodium triacetoxy borohydride (1.1 equiv) and stir at rt overnight. The reaction is quenched with aqueous sodium bicarbonate, extracted with methylene chloride, dried, and concentrated. The resultant material is purified by silica gel chromatography to afford the separated diastereomers of 2-(6,8-Difluoro-1,2,3,4-tetrahydro-naphthalen-2-ylamino)-pentanoic acid methyl ester: Diastereomer 1; 13C NMR (100 MHz, CDCl3) 14.0, 19.4, 27.7, 28.2, 29.5, 29.6, 36.3, 51.1, 58.7, 100.7, 100.9, 101.2, 110.5, 110.7, 110.8, 118.5, 118.6, 141.1, 159.7, 159.8, 162.1, 176.7; MS m/z 298.3 (M+1). Diastereomer 2; Diagnostic $^{13}$C NMR (100 MHz, CDCl3) 14.0, 19.3, 28.3, 28.4, 28.5, 30.3, 36.4, 51.1, 52.0, 58.5, 100.7, 100.9, 101.2, 110.5, 110.7, 176.8; MS m/z 298.3 (M+1).

2-(6,8-Difluoro-1,2,3,4-tetrahydro-naphthalen-2-ylamino)-pentanoic acid methyl ester (1 equiv) is dissolved in THF:water (5:1) and LiOH (1.2 equiv) is added. The reaction is stirred overnight at rt, the solvent is removed, water added, and the pH is adjusted to 7 using 1N hydrochloric acid. The solid is filtered, washed with water and diethyl ether, and dried to afford 2-(6,8-Difluoro-1,2,3,4-tetrahydro-naphthalen-2-ylamino)-pentanoic acid; Acid derived from diastereomer 1: H1 NMR (400 MHz, CD3OD) 0.99 (t, 3H, J=7.5), 1.48 (m, 2H), 1.82 (m, 3H), 2.36 (m, 1H), 2.65 (m, 1H), 2.95 (m, 2H), 3.28 (s, 1H), 3.42 (m, 1H), 3.74 (m, 1H), 6.80 (m, 2H); (MS m/z 284.3 (M+1). Acid derived from diastereomer 2: H1 NMR (400 MHz, CD3OD) 0.94 (t, 3H, J=7.6), 1.42 (m, 2H), 1.56 (m, 3H), 1.96 (m, 1H), 2.25 (m, 1H), 2.85 (m, 3H), 3.15 (m, 1H), 3.25 (m, 1H), 6.64 (m, 2H); MS m/z 284.2 (M+1).

Combine 2-(6,8-Difluoro-1,2,3,4-tetrahydro-naphthalen-2-ylamino)-pentanoic acid (1 equiv) derived from diastereomer #2 above, TPTU (1 equiv), diisopropylethylamine (2 equiv) in DMF followed by 1-[2-(2,2-dimethyl-propylamino)-1,1-dimethyl-ethyl]-1H-imidazol-4-ylamine (2 equiv) in methylene chloride. The reaction is stirred overnight at rt, quenched with aq. sodium bicarbonate, and extracted with methylene chloride. The solvent is dried, concentrated, and purified by silica gel chromatography to afford diastereomer #2 of the title compound: C13 NMR (100 MHz, CDCl3) 14.1, 19.5, 26.4, 27.8, 28.2, 28.9, 29.8, 32.1, 36.6, 38.8, 52.8, 59.1, 60.9, 61.3, 63.0, 100.8, 101.0, 101.3, 104.5, 110.6, 110.8, 110.9, 131.2, 137.6, 139.8, 159.8, 172.4; MS m/z 490.2 (M+1).

Combine 2-(6,8-Difluoro-1,2,3,4-tetrahydro-naphthalen-2-ylamino)-pentanoic acid (1 equiv) derived from diastereomer #1 above, TPTU (1 equiv), diisopropylethylamine (2 equiv) in DMF followed by 1-[2-(2,2-dimethyl-propylamino)-1,1-dimethyl-ethyl]-1H-imidazol-4-ylamine (2 equiv) in methylene chloride. The reaction is stirred overnight at rt, quenched with aq. sodium bicarbonate, and extracted with methylene chloride. The solvent is dried, concentrated, and purified by silica gel chromatography to afford diastereomer #1 of the title compound.

Example 87

2-(6,8-Difluoro-1,2,3,4-tetrahydro-naphthalen-2-ylamino)-pentanoic acid [1-(1,1-dimethyl-2-piperidin-1-yl-ethyl)-1H-imidazol-4-yl]-amide Following the procedure for Example 86, 2-(6,8-Difluoro-1,2,3,4-tetrahydro-naphthalen-2-ylamino)-pentanoic acid (diastereomer 2) was reacted with 1-(1,1-Dimethyl-2-piperidin-1-yl-ethyl)-1H-imidazol-4-ylamine to afford the title compound: C13 NMR (100 MHz, CDCl3) 14.1, 19.5, 24.1, 25.8, 25.9, 26.7, 28.2, 28.9, 29.8, 36.6, 38.8, 52.8, 56.8, 59.1, 60.9, 69.1, 100.8, 101.0, 101.3, 104.6, 110.7, 110.8, 118.2, 131.3, 137.2, 139.9, 172.3; MS m/z 488.3 (M+1).

Example 88

2-(6,8-Difluoro-1,2,3,4-tetrahydro-naphthalen-2-ylamino)-pentanoic acid [1-(2-dimethylamino-1,1-dimethyl-ethyl)-1H-imidazol-4-yl]-amide Following the procedure for Example 86, 2-(6,8-Difluoro-1,2,3,4-tetrahydro-naphthalen-2-ylamino)-pentanoic acid (diastereomer 2) was reacted with 1-(2-Dimethylamino-1,1-dimethyl-ethyl)-1H-imidazol-4-ylamine to afford the title compound: C13 NMR (100 MHz, CDCl3) 14.1, 19.5, 26.2, 28.2, 28.8, 28.9, 29.8, 36.6, 48.0, 52.8, 59.0, 60.9, 70.0, 100.8, 101.1, 101.3, 104.6, 110.7, 110.8, 131.3, 137.4, 172.3; MS m/z 448.3 (M+1).

Example 89

2-(6,8-Difluoro-1,2,3,4-tetrahydro-naphthalen-2-ylamino)-pentanoic acid {1-[1,1-dimethyl-2-(2,2,2-trifluoro-ethylamino)-ethyl]-1H-imidazol-4-yl}-amide Following the procedure for Example 86, 2-(6,8-Difluoro-1,2,3,4-tetrahydro-naphthalen-2-ylamino)-pentanoic acid (diastereomer 2) was reacted with 1-[1,1-Dimethyl-2-(2,2,2-trifluoro-ethylamino)-ethyl]-1H-imidazol-4-ylamine to afford the title compound: C13 MR (100 MHz, CDCl3) 14.1, 19.5, 26.0, 28.2, 28.8, 29.8, 36.6, 38.8, 50.5, 50.8, 51.1, 51.4, 52.7, 58.6, 58.7, 60.8, 100.8, 101.0, 101.3, 104.3, 110.7, 110.8, 110.9, 118.0, 118.1, 124.2, 127.0, 131.2, 138.0, 139.8, 159.9, 172.6; MS m/z 502.2 (M+1).

Example 90

2-(6,8-Difluoro-1,2,3,4-tetrahydro-naphthalen-2-ylamino)-pentanoic acid [1-(1,1-dimethyl-2-pyrrolidin-1-yl-ethyl)-1H-imidazol-4-yl]-amide Following the procedure for Example 86, 2-(6,8-Difluoro-1,2,3,4-tetrahydro-naphthalen-2-ylamino)-pentanoic acid (diastereomer 2) was reacted with 1-(1,1-Dimethyl-2-pyrrolidin-1-yl-ethyl)-4-nitro-1H-imidazole to afford the title compound: C13 NMR (100 MHz, CDCl3) 14.2, 19.5, 24.3, 26.6, 28.2, 28.8, 28.9, 29.8, 36.6, 52.8, 56.0, 59.1, 60.9, 67.3, 100.8, 101.1, 101.3, 104.8, 110.7, 110.9, 112.5, 131.2, 137.3, 172.4; MS m/z 474.3 (M+1).

Example 91

2-(6,8-Difluoro-1,2,3,4-tetrahydro-naphthalen-2-ylamino)-pentanoic acid [1-(1,1-dimethyl-2-pyrrolidin-1-yl-ethyl)-1H-imidazol-4-yl]-amide Following the procedure for Example 86, 2-(6,8-Difluoro-1,2,3,4-tetrahydro-naphthalen-2-ylamino)-pentanoic acid (diastereomer 1) was reacted with 1-(1,1-Dimethyl-2-pyrrolidin-1-yl-ethyl)-4-nitro-1H-imidazole to afford the title compound: C13 NMR (100 MHz, CDCl3) 14.2, 19.6, 24.3, 26.6, 28.2, 28.6, 29.6, 36.6, 51.9, 56.0, 59.3, 60.3, 67.2, 100.8, 101.0, 101.3, 104.9, 110.7, 112.5, 130.8, 172.6; MS m/z 474.3 (M+1).

Example 92

2-(6,8-Difluoro-1,2,3,4-tetrahydro-naphthalen-2-ylamino)-pentanoic acid [1-(3-hydroxy-cyclobutyl)-1H-imidazol-4-yl]-amide Following the procedure for Example 86, 2-(6,8-Difluoro-1,2,3,4-tetrahydro-naphthalen-2-ylamino)-pentanoic acid (diastereomer 2) was reacted with 3-(4-Amino-imidazol-1-yl)-cyclobutanol to afford the title compound: C13 NMR (100 MHz, CDCl3) 14.1, 19.5, 28.2, 28.9, 29.7, 36.5, 40.2, 41.9, 43.4, 48.7, 52.9, 60.5, 60.9, 64.5, 100.8, 101.1, 101.3, 105.1, 105.3, 110.7, 110.9, 131.6, 131.9, 137.7, 139.8, 159.8, 162.3, 172.6; MS m/z 419.2 (M+1).

Example 93

2-(6,8-Difluoro-1,2,3,4-tetrahydro-naphthalen-2-ylamino)-pentanoic acid {1-[2-(2,6-dimethyl-morpholin-4-yl)-1,1-dimethyl-ethyl]-1H-imidazol-4-yl}-amide Following the procedure for Example 86, 2-(6,8-Difluoro-1,2,3,4-tetrahydro-naphthalen-2-ylamino)-pentanoic acid (diastereomer 2) was reacted with 1-[2-(2,6-Dimethyl-morpholin-4-yl)-1,1-dimethyl-ethyl]-1H-imidazol-4-ylamine to afford the title compound: C13 NMR (100 MHz, CDCl3) 14.1, 19.1, 19.5, 25.9, 28.2, 28.9, 29.7, 36.6, 38.8, 53.0, 58.9, 61.0, 61.3, 68.5, 72.1, 74.4, 76.9, 77.3, 77.6, 100.8, 101.1, 101.3, 104.7, 110.7, 110.9, 117.9, 131.2, 137.3, 139.8, 159.8, 162.3, 172.3; MS m/z 518.2 (M+1).

Example 94

2-(6,8-Difluoro-1,2,3,4-tetrahydro-naphthalen-2-ylamino)-pentanoic acid (1-{2-[(2,2-dimethyl-propyl)-methyl-amino]-1,1-dimethyl-ethyl}-1H-imidazol-4-yl)-amide Following the procedure for Example 86, 2-(6,8-Difluoro-1,2,3,4-tetrahydro-naphthalen-2-ylamino)-pentanoic acid (diastereomer 2) was reacted with 1-{2-[(2,2-Dimethyl-propyl)-methyl-amino]-1,1-dimethyl-ethyl}-1H-imidazol-4-ylamine to afford the title compound: C13 NMR (100 MHz, CDCl3) 14.2, 19.5, 26.8, 28.2, 28.8, 28.9, 29.8, 33.4, 36.6, 46.6, 52.8, 59.4, 59.5, 60.9, 72.4, 74.2, 101.1, 104.8, 106.9, 110.7, 110.9, 118.0, 131.1, 137.4, 139.3, 139.8, 162.2, 172.4, 194.6; MS m/z 504.4 (M+1).

Example 95

2-(6,8-Difluoro-1,2,3,4-tetrahydro-naphthalen-2-ylamino)-pentanoic acid {1-[1,1-dimethyl-2-(4-methyl-piperazin-1-yl)-ethyl]-1H-imidazol-4-yl}-amide Following the procedure for Example 86, 2-(6,8-Difluoro-1,2,3,4-tetrahydro-naphthalen-2-ylamino)-pentanoic acid (diastereomer 2) was reacted with 1-[1,1-Dimethyl-2-(4-methyl-piperazin-1-yl)-ethyl]-1H-imidazol-4-ylamine to afford the title compound: C13 NMR (100 MHz, CDCl3) 14.2, 19.5, 25.8, 25.9, 28.2, 28.9, 29.7, 36.5, 46.1, 52.9, 55.0, 55.7, 59.0, 60.9, 68.2, 101.1, 101.3, 104.5, 110.9, 131.3, 137.3, 172.3; MS m/z 503.3 (M+1).

Example 96

2-[2-(3,5-Difluoro-phenyl)-acetylamino]-pentanoic acid [1-(2-morpholin-4-yl-ethyl)-1H-imidazol-4-yl]-amide 2-[2-(3,5-Difluoro-phenyl)-acetylamino]-pentanoic acid [1-(2-hydroxy-ethyl)-1H-imidazol-4-yl]-amide (1 equiv) was dissolved in pyridine and treated with methansulfonyl chloride (2.2 equiv) at 0° C. The reaction was warmed to rt and stirred for 4 h, quenched with sodium bicarbonate, and extracted with methylene chloride. The extracts were dried and concentrated to provide methanesulfonic acid 2-(4-{2-[2-(3,5-difluoro-phenyl)-acetylamino]-pentanoylamino}-imidazol-1-yl)-ethyl ester which was used without further purification.

Methanesulfonic acid 2-(4-{2-[2-(3,5-difluoro-phenyl)-acetylamino]-pentanoylamino}-imidazol-1-yl)-ethyl ester (1 equiv) was dissolved in acetonitrile and treated with potassium carbonate (1.5 equic) and morpholine (3 equiv). The reaction was heated to 65° C. for 18 h and quenched with water, extracted with methylene chloride, dried, and concentrated. The residue was purified by column chromatography to afford the title compound: C13 NMR (100 MHz, CDCl3) 14.0, 18.9, 36.0, 43.1, 45.1, 53.1, 53.9, 58.9, 67.1, 102.6, 102.9, 107.9, 112.3, 112.6, 133.5, 137.6, 139.0, 161.0, 162.0, 169.3, 169.4; MS m/z 450.1 (M+1).

Example 97

2-[2-(3,5-Difluoro-phenyl)-acetylamino]-pentanoic acid {1-[2-(2,2-dimethyl-propylamino)-ethyl]-1H-imidazol-4-yl}-amide The title compound was prepared following the procedure shown for Example 96 using 2,2-dimethyl-propylamine to afford the title compound: C13 NMR (100 MHz, CDCl3) 14.0, 18.8, 27.8, 31.8, 35.9, 43.1, 47.9, 50.9, 53.2, 62.0, 102.9, 107.7, 112.3, 112.6, 133.5, 137.7, 169.3; MS m/z 450.2 (M+1).

Example 98

2-[2-(3,5-Difluoro-phenyl)-acetylamino]-pentanoic acid {1-[2-(4-methyl-piperazin-1-yl)-ethyl]-1H-imidazol-4-yl}-amide The title compound was prepared following the procedure shown for Example 96 using N-methyl piperazine to afford the title compound: C13 NMR (100 MHz, CDCl3) 14.0, 18.9, 36.0, 43.1, 45.4, 46.1, 53.1, 53.4, 55.1, 58.4, 102.8, 107.9, 112.3, 112.6, 133.5, 137.5, 139.0, 162.0, 164.3, 169.3, 169.5; MS m/z 463.3. (M+1).

Example 99

2-[2-(3,5-Difluoro-phenyl)-acetylamino]-pentanoic acid [1-(2-hydroxy-1,12-trimethyl-propyl)-1H-imidazol-4-yl]-amide To a solution of 2-(4-{2-[2-(3,5-difluoro-phenyl)-acetylamino]-pentanoylamino}-imidazol-1-yl)-2-methyl-propionic acid methyl ester (1 equiv) in tetrahydrofuran at −78° C. is added methyllithium-lithium bromide (5 equiv., 1.5 M in ether) dropwise. The reaction is stirred for 30 min., quenched with water, and extracted with methylene chloride. The solvent is dried, concentrated, and purified by silica gel chromatography to afford the title compound: C13 NMR (100 MHz, CDCl3) 14.0, 18.9, 24.3, 25.2, 26.0, 35.9, 42.9, 53.1, 64.7, 74.4, 102.8, 107.2, 112.4, 112.6, 133.3, 136.3, 169.0, 169.2; MS m/z 437.3 (M+1).

Example 100

2-[2-(3,5-Difluoro-phenyl)-acetylamino]-pentanoic acid [1-(3-hydroxy-1,13-trimethyl-butyl)-1H-imidazol-4-yl]-amide Following the procedure of Example 99, 3-(4-{2-[2-(3,5-Difluoro-phenyl)-acetylamino]-pentanoylamino}-imidazol-1-yl)-3-methyl-butyric acid methyl ester was reacted with methyllithium-lithium bromide to afford the title compound: C13 NMR (100 MHz, CDCl3) 14.0, 18.9, 29.9, 30.3, 31.5, 36.0, 43.1, 53.1, 53.7, 58.2, 70.9, 102.9, 105.6, 112.3, 112.6, 131.7, 137.5, 138.5, 164.4, 169.1, 169.3; MS m/z 451.2 (M+1)

Example 101

2-[2-(3,5-Difluoro-phenyl)-acetylamino]-pentanoic acid [1-(2-ethyl-2-hydroxy-1,1-dimethyl-butyl)-1H-imidazol-4-yl]-amide To a solution of 2-(4-{2-[2-(3,5-difluoro-phenyl)-acetylamino]-pentanoylamino}-imidazol-1-yl)-2-methyl-propionic acid methyl ester (1 equiv) in tetrahydrofuran at –0° C. is added ethyl lithium (5 equiv., 0.5 M benzene/cyclohexane) dropwise. The reaction is stirred for 30 min., quenched with water, and extracted with methylene chloride. The solvent is dried, concentrated, and purified by silica gel chromatography to afford the title compound: C13 NMR (100 MHz, CDCl3) 9.0, 9.3, 14.0, 18.9, 24.5, 25.2, 27.3, 27.5, 36.0, 43.0, 53.1, 65.9, 102.5, 102.8, 103.0, 107.2, 112.4, 112.6, 112.7, 133.3, 136.3, 138.6, 164.3, 164.5, 169.0, 169.1; MS m/z 465.3 (M+1).

Example 102

2-[2-(3,5-Difluoro-phenyl)-acetylamino]-pentanoic acid [1-(3-ethyl-3-hydroxy-1,1-dimethyl-pentyl)-1H-imidazol-4-yl]-amide Following the procedure of Example 101, 3-(4-{2-[2-(3,5-Difluoro-phenyl)-acetylamino]-pentanoylamino}-imidazol-1-yl)-3-methyl-butyric acid methyl ester was reacted with ethyl lithium to afford the title compound: C13 NMR (100 MHz, CDCl3) 7.9, 8.2, 14.0, 18.8, 29.9, 30.7, 31.5, 32.2, 36.0, 43.1, 49.2, 53.1, 58.2, 75.1, 102.9, 103.1, 105.5, 112.3, 112.6, 131.8, 137.4, 162.0, 168.9, 169.2; MS m/z 479.3 (M+1).

Example 103

The following compounds are prepared utilizing the procedures described above.
2-[2-(3,5-Difluoro-phenyl)-acetylamino]-pentanoic acid (1-tert-butyl-1H-imidazol-4-yl)-amide;
2-[2-(3,5-Difluoro-phenyl)-2-hydroxy-acetylamino]-pentanoic acid (1-tert-butyl-1H-imidazol-4-yl)-amide;
2-(2-Hydroxy-3,3-dimethyl-butyrylamino)-pentanoic acid (1-tert-butyl-1H-imidazol-4-yl)-amide;
2-(6,8-Difluoro-1,2,3,4-tetrahydro-naphthalen-2-ylamino)-pentanoic acid (1-tert-butyl-1H-imidazol-4-yl)-amide;
2-[2-(3,5-Difluoro-phenyl)-2-hydroxy-acetylamino]-N-(1-isopropyl-1H-imidazol-4-yl)-propionamide;
2-(2-Hydroxy-3,3-dimethyl-butyrylamino)-pentanoic acid (1-isopropyl-1H-imidazol-4-yl)-amide;
2-[2-(3,5-Difluoro-phenyl)-acetylamino]-pentanoic acid {1-[2-(3-hydroxy-pyrrolidin-1-yl)-1,1-dimethyl-ethyl]-1H-imidazol-4-yl}-amide;
2-[2-(3,5-Difluoro-phenyl)-acetylamino]-pentanoic acid {1-[1-(2,2-dimethyl-propyl)-azetidin-3-yl]-1H-imidazol-4-yl}-amide;
2-[2-(3,5-Difluoro-phenyl)-acetylamino]-pentanoic acid {1-[1-(2,2-dimethyl-propionyl)-azetidin-3-yl]-1H-imidazol-4-yl}-amide;
2-[2-(3,5-Difluoro-phenyl)-acetylamino]-pentanoic acid [1-(2-isopropoxy-1,1-dimethyl-ethyl)-1H-imidazol-4-yl]-amide;
2-(6,8-Difluoro-1,2,3,4-tetrahydro-1,4-methano-naphthalen-2-ylamino)-pentanoic acid [1-(1,1-dimethyl-2-morpholin-4-yl-ethyl)-1H-imidazol-4-yl]-amide;
2-(5,7-Difluoro-chroman-3-ylamino)-pentanoic acid [1-(1,1-dimethyl-2-morpholin-4-yl-ethyl)-1H-imidazol-4-yl]-amide;
2-(4,6-Difluoro-tricyclo[6.2.2]dodeca-2(7),3,5-trien-9-ylamino)-pentanoic acid [1-(1,1-dimethyl-2-morpholin-4-yl-ethyl)-1H-imidazol-4-yl]-amide;
2-(Naphthalen-2-ylamino)-pentanoic acid [1-(1,1-dimethyl-2-morpholin-4-yl-ethyl)-1H-imidazol-4-yl]-amide;
2-(Quinolin-3-ylamino)-pentanoic acid [1-(1,1-dimethyl-2-morpholin-4-yl-ethyl)-1H-imidazol-4-yl]-amide;
2-(1-Methyl-1H-indol-3-ylamino)-pentanoic acid [1-(1,1-dimethyl-2-morpholin-4-yl-ethyl)-1H-imidazol-4-yl]-amide;
2-[2-(3,5-Difluoro-phenyl)-acetylamino]-pentanoic acid [1-(1,1-dimethyl-2-pyrrolidin-1-yl-ethyl)-2-trifluoromethyl-1H-imidazol-4-yl]-amide;
2-[2-(3,5-Difluoro-phenyl)-acetylamino]-pentanoic acid [1-(1,1-dimethyl-2-pyrrolidin-1-yl-ethyl)-2-fluoro-1H-imidazol-4-yl]-amide;
2-[2-(3,5-Difluoro-phenyl)-acetylamino]-pentanoic acid [1-(1,1-dimethyl-2-pyrrolidin-1-yl-ethyl)-2-phenyl-1H-imidazol-4-yl]-amide;
2-[2-(3,5-Difluoro-phenyl)-acetylamino]-pentanoic acid [1-(1,1-dimethyl-2-pyrrolidin-1-yl-ethyl)-5-phenyl-1H-imidazol-4-yl]-amide;
2-[2-(3,5-Difluoro-phenyl)-acetylamino]-pentanoic acid [1-(1,1-dimethyl-2-pyrrolidin-1-yl-ethyl)-5-trifluoromethyl-1H-imidazol-4-yl]-amide;
5-{2-[2-(3,5-Difluoro-phenyl)-acetylamino]-pentanoylamino}-3-(1,1-dimethyl-2-pyrrolidin-1-yl-ethyl)-3H-imidazole-4-carboxylic acid methyl ester;
2-[2-(3,5-Difluoro-phenyl)-acetylamino]-pentanoic acid (6,6-dimethyl-5,6,7,8-tetrahydro-imidazo[1,5-a]pyridin-1-yl)-amide;
2-[2-(3,5-Difluoro-phenyl)-acetylamino]-pentanoic acid (6-methyl-5,6,7,8-tetrahydro-imidazo[1,2-a]pyridin-2-yl)-amide;
2-[2-(3,5-Difluoro-phenyl)-acetylamino]-pentanoic acid (3,4-dihydro-2H-imidazo[5,1-b][1,3]oxazin-8-yl)-amide;
2-[2-(3,5-Difluoro-phenyl)-acetylamino]-pentanoic acid (1H-imidazo[1,2-a]pyridin-3-yl)-amide;
2-[2-(3,5-Difluoro-phenyl)-ethylamino]-pentanoic acid [1-(1,1-dimethyl-2-pyrrolidin-1-yl-ethyl)-1H-imidazol-4-yl]-amide;
2-[2-(3,5-Difluoro-phenyl)-2-hydroxy-ethylamino]-pentanoic acid [1-(1,1-dimethyl-2-pyrrolidin-1-yl-ethyl)-1H-imidazol-4-yl]-amide;
2-[2-(3,5-Difluoro-phenyl)-1-methyl-ethylamino]-pentanoic acid [1-(1,1-dimethyl-2-pyrrolidin-1-yl-ethyl)-1H-imidazol-4-yl]-amide;

2-(3,5-Difluoro-benzylamino)-pentanoic acid [1-(1,1-dimethyl-2-pyrrolidin-1-yl-ethyl)-1H-imidazol-4-yl]-amide;

2-(6,8-Difluoro-1,2,3,4-tetrahydro-naphthalen-2-ylamino)-pentanoic acid [1-(1-dimethylaminomethyl-cyclopentyl)-1H-imidazol-4-yl]-amide; and 2-(6,8-Difluoro-1-hydroxy-1,2,3,4-tetrahydro-naphthalen-2-ylamino)-pentanoic acid [1-(1,1-dimethyl-2-pyrrolidin-1-yl-ethyl)-1H-imidazol-4-yl]-amide The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A compound of Formula I,

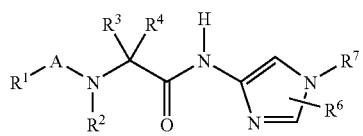

wherein:

A is absent;

$R^1$ is benzo($C_5$-$C_6$ cycloalkyl) optionally substituted with from one to three substituents independently selected from $C_1$-$C_6$ alkyl, halo, and —OH;

$R^2$ is hydrogen or $C_1$-$C_6$ alkyl;

$R^3$ is hydrogen or $C_1$-$C_6$ alkyl;

$R^4$ is hydrogen or $C_1$-$C_6$ alkyl;

$R^6$ is hydrogen or $C_1$-$C_6$ alkyl;

$R^7$ is $C_1$-$C_{10}$ alkyl, wherein $R^7$ is optionally substituted with from one to three substituents independently selected from $C_1$-$C_8$ alkoxy, —OH, —$NR^9R^{10}$, —C(=O)$NR^9R^{10}$, —C(=O)$R^{11}$, and —C(=O)$OR^{11}$; and $R^9$, $R^{10}$, and $R^{11}$ are each independently selected from hydrogen and $C_1$-$C_6$ alkyl, wherein each hydrogen atom of said $C_1$-$C_6$ alkyl is optionally independently replaced with a halo atom; or a pharmaceutically acceptable salt thereof.

2. A compound according to claim 1, wherein $R^1$ is benzo($C_5$-$C_6$ cycloalkyl) optionally substituted with from one to three halo, or a pharmaceutically acceptable salt thereof.

3. A compound according to claim 2, wherein $R^1$ is benzo($C_5$-$C_6$ cycloalkyl) optionally substituted with from one to three fluorine or chlorine, or a pharmaceutically acceptable salt thereof.

4. A compound according to claim 3, wherein $R^1$ is 1,2,3,4-tetrahydronaphthalenyl or indanyl optionally substituted with from one to three halo, or a pharmaceutically acceptable salt thereof.

5. A compound according to claim 4, wherein $R^1$ is 1,2,3,4-tetrahydronaphthalenyl optionally substituted with from one to three halo, or a pharmaceutically acceptable salt thereof.

6. A compound according to claim 3, wherein $R^1$ is benzo($C_5$-$C_6$ cycloalkyl) optionally substituted with from one to three fluorine, or a pharmaceutically acceptable salt thereof.

7. A compound according to claim 6, wherein $R^1$ is 1,2,3,4-tetrahydronaphthalenyl or indanyl optionally substituted with from one to three fluorine, or a pharmaceutically acceptable salt thereof.

8. A compound according to claim 7, wherein $R^1$ is 1,2,3,4-tetrahydronaphthalenyl optionally substituted with from one to three fluorine, or a pharmaceutically acceptable salt thereof.

9. A compound of Formula I,

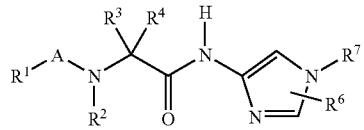

wherein:

A is absent;

$R^1$ is benzo($C_5$-$C_6$ cycloalkyl) optionally substituted with from one to three independently selected halo;

$R^2$ is hydrogen or $C_1$-$C_6$ alkyl;

$R^3$ is hydrogen, —$CH_2CH_2SCH_3$, —O($C_1$-$C_4$)alkyl or $C_1$-$C_6$ alkyl;

$R^4$ is hydrogen or $C_1$-$C_6$ alkyl;

$R^6$ is hydrogen or $C_1$-$C_6$ alkyl;

$R^7$ is $C_1$-$C_{10}$ alkyl, wherein $R^7$ is optionally substituted with from one to three substituents independently selected from $C_1$-$C_8$ alkoxy, —OH, —$NR^9R^{10}$, —C(=O)$NR^9R^{10}$, —C(=O)$R^{11}$, —C(=O)$OR^{11}$, and (4-6 membered) heterocycloalkyl; and $R^9$, $R^{10}$, and $R^{11}$ are each independently selected from hydrogen and $C_1$-$C_6$ alkyl, wherein each hydrogen atom of said $C_1$-$C_6$ alkyl is optionally independently replaced with a halo atom; or a pharmaceutically acceptable salt thereof.

10. A compound according to claim 9, wherein $R^1$ is benzo($C_5$-$C_6$ cycloalkyl) optionally substituted with from one to three fluorine, or a pharmaceutically acceptable salt thereof.

11. A compound according to claim 10, wherein $R^1$ is 1,2,3,4-tetrahydronaphthalenyl or indanyl optionally substituted with from one to three fluorine, or a pharmaceutically acceptable salt thereof.

12. A compound according to claim 11, wherein $R^1$ is 1,2,3,4-tetrahydronaphthalenyl optionally substituted with from one to three fluorine, or a pharmaceutically acceptable salt thereof.

13. A compound according to claim 9, wherein $R^7$ is $C_1$-$C_6$ alkyl optionally substituted with —$NR^9R^{10}$, morpholinyl, pyrrolidinyl, or piperidinyl, or a pharmaceutically acceptable salt thereof.

14. A compound according to claim 12, wherein $R^7$ is $C_1$-$C_6$ alkyl optionally substituted with —$NR^9R^{10}$, morpholinyl, pyrrolidinyl, or piperidinyl, or a pharmaceutically acceptable salt thereof.

15. A compound according to claim 14, wherein $R^7$ is $C_1$-$C_6$ alkyl optionally substituted with —$NR^9R^{10}$, or a pharmaceutically acceptable salt thereof.

16. A compound according to claim 14, wherein $R^7$ is $C_1$-$C_6$ alkyl substituted with —$NR^9R^{10}$, or a pharmaceutically acceptable salt thereof.

17. A compound according to claim 1, wherein the compound of Formula I has the structure

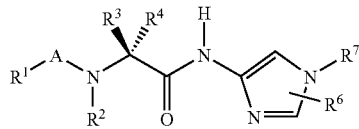

and wherein $R^2$ and $R^4$ are hydrogen, or a pharmaceutically acceptable salt thereof.

18. A compound according to claim 9, wherein the compound of Formula I has the structure

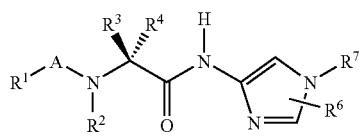

and wherein $R^2$ and $R^4$ are hydrogen, or a pharmaceutically acceptable salt thereof.

19. A pharmaceutical composition, comprising an amount of a compound according to claim 1, or a pharmaceutically acceptable salt thereof, and a pharmaceutically acceptable carrier.

20. A pharmaceutical composition, comprising an amount of a compound according to claim 9, or a pharmaceutically acceptable salt thereof, and a pharmaceutically acceptable carrier.

21. A pharmaceutical composition, comprising an amount of a compound according to claim 17, or a pharmaceutically acceptable salt thereof, and a pharmaceutically acceptable carrier.

22. A pharmaceutical composition, comprising an amount of a compound according to claim 18, or a pharmaceutically acceptable salt thereof, and a pharmaceutically acceptable carrier.

* * * * *